US010557138B2

(12) United States Patent
Gleit-Kielmanowicz et al.

(10) Patent No.: US 10,557,138 B2
(45) Date of Patent: Feb. 11, 2020

(54) **COMPOSITIONS AND METHODS FOR VIRUS CONTROL IN *VARROA* MITE AND BEES**

(71) Applicant: Beeologics, Inc., St. Louis, MO (US)

(72) Inventors: Merav Gleit-Kielmanowicz, Hod Hasharon (IL); Yael Golani, Rehovot (IL)

(73) Assignee: BEEOLOGICS, INC., St. Louis, MO (US)

( * ) Notice: Subject to any disclaimer, the term of this patent is extended or adjusted under 35 U.S.C. 154(b) by 0 days.

(21) Appl. No.: 15/103,685

(22) PCT Filed: Dec. 9, 2014

(86) PCT No.: PCT/US2014/069353
§ 371 (c)(1),
(2) Date: Jun. 10, 2016

(87) PCT Pub. No.: WO2015/089078
PCT Pub. Date: Jun. 18, 2015

(65) Prior Publication Data
US 2017/0037407 A1 Feb. 9, 2017

Related U.S. Application Data

(60) Provisional application No. 62/069,142, filed on Oct. 27, 2014, provisional application No. 61/913,917, filed on Dec. 10, 2013.

(51) Int. Cl.
*C12N 15/113* (2010.01)
*C12N 5/00* (2006.01)

(52) U.S. Cl.
CPC ...... *C12N 15/1131* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |

(Continued)

FOREIGN PATENT DOCUMENTS

| AU | 2008258254 B2 | 7/2014 |
| AU | 2014262189 B2 | 11/2014 |

(Continued)

OTHER PUBLICATIONS

Agricultural Chemical Usage 2006 Vegetables Summary, Agricultural Statistics Board, NASS, USDA, pp. 1-372 (2007).
Agrios, Plant Pathology (Second Edition), 2:466-470 (1978).
Alarcón-Reverte et al., "Resistance to ACCase-inhibiting herbicides in the weed Lolium multiflorum," Comm, Appl. Biol. Sci., 73(4):899-902 (2008).
Al-Kaff et al., "Plants rendered herbicide-susceptible by cauliflower mosaic virus-elicited suppression of a 35S promoter-regulated transgene," Nature Biotechnology, 18:995-999 (2000).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).

(Continued)

Primary Examiner — Sean McGarry
(74) Attorney, Agent, or Firm — Arnold & Porter Kaye Scholer LLP; Amanda Carmany-Rampey; David R. Marsh

(57) ABSTRACT

Compositions and methods for providing viral control in *Varroa* mites and bees using RNA interference technology, and more particularly, prevention and treatment of viral infections in *Varroa* mites and bees by providing trigger polynucleotides targeting viral sequences is disclosed.

8 Claims, 12 Drawing Sheets

Specification includes a Sequence Listing.

(56) References Cited

U.S. PATENT DOCUMENTS

| | | |
|---|---|---|
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,384,253 A | 1/1995 | Krzyzek et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Feigner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Huberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Solt et al. |
| 6,479,291 B2 | 11/2002 | Kumagai et al. |
| 6,506,559 B1 | 1/2003 | Fire et al. |
| 6,642,435 B1 | 11/2003 | Rafatski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |

(56) References Cited

U.S. PATENT DOCUMENTS

| | | |
|---|---|---|
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,226,938 B1 | 7/2012 | Meikle et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,422,557 B2 | 8/2016 | Ader |
| 9,445,603 B2 | 9/2016 | Baum et al. |
| 9,777,288 B2 | 10/2017 | Beattie et al. |
| 9,850,496 B2 | 12/2017 | Beattie et al. |
| 9,856,495 B2 | 1/2018 | Beattie et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0221211 A1 | 11/2003 | Rottmann et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2005/0289664 A1 | 12/2005 | Moshiri et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0203013 A1 | 8/2011 | Peterson et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |

(56) References Cited

U.S. PATENT DOCUMENTS

| | | |
|---|---|---|
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0174262 A1 | 7/2012 | Azhakanandam et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1* | 10/2012 | Sela ............... A61K 31/713 449/2 |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0289097 A1* | 10/2013 | Paldi ............... C12N 15/113 514/44 A |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | |
|---|---|---|
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |
| JP | 2009137851 A | 6/2009 |
| RU | 2 291 613 C1 | 1/2007 |
| RU | 2 337 529 C1 | 11/2008 |
| WO | WO 89/11789 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/14348 A1 | 3/1999 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A2 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |

(56) References Cited

FOREIGN PATENT DOCUMENTS

| | | |
|---|---|---|
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/153607 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/156342 A1 | 11/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |

(56) References Cited

FOREIGN PATENT DOCUMENTS

| | | |
|---|---|---|
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Andersen et al., "Delivery of siRNA from lyophilized polymeric surfaces,"Biomaterials, 29:506-512 (2008).

Andersson et al., "A novel selection system for potato transformation using a mutated AHAS gene," Plant Cell Reports, 22(4):261-267 (2003).

Anonymous, "A handbook for high-level expression and purification of 6xHis-tagged proteins," The QiaExpressionist, (2003).

Anonymous, "Agronomy Facts 37: Adjuvants for enhancing herbicide performance," n.p., 1-8, (Jan. 26, 2000), Web, (Jan. 21, 2014).

Anonymous, "Devgen, The mini-Monsanto," KBC Securities (2006).

Anonymous, "Do Monsanto have the next big thing?," Austalian Herbicide Resistance Initiative (AHRI), (Apr. 23, 2013) Web. (Jan. 19, 2015).

Aoki et al., "In Vivo Transfer Efficiency of Antisense Oligonucleotides into the Myocardium Using HVJ-Liposome Method," Biochem Biophys Res Commun, 231:540-545 (1997).

Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).

Artymovich, "Using RNA interference to increase crop yield and decrease pest damage," MMG 445 Basic Biotech., 5(1):7-12 (2009).

Axtell et al., "A Two-Hit Trigger for siRNA Biogenesis in Plants," Cell, 127:565-577 (2006).

Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).

Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).

Bai et al., "Naturally Occurring Broad-Spectrum Powdery Mildew Resistance in a Central American Tomato Accession Is Caused by Loss of Mlo Function," MPMI, 21(I):30-39 (2008).

Balibrea et al., "Extracellular Invertase is an Essential Component of Cytokinin-Mediated Delay of Senescence," The Plant Cell, 16(5):1276-1287 (2004).

Bannerjee et al., "Efficient production of transgenic potato (*S. tuberosum* L. ssp. *andigena*) plants via Agrobacterium tumefaciens-mediated transformation," Plant Sci., 170:732 738 (2006).

Bart et al., "A novel system for gene silencing using siRNAs in rice leaf and stem-derived protoplasts," Plant Methods, 2(13):1-9 (2006).

Basu et al., "Weed genomics: new tools to understand weed biology," Trends in Plant Science, 9(8):391-398 (2004).

Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).

Bayer et al., "Programmable ligand-controlled riboregulators of eukaryotic gene expression," Nature Biotechnol., 23(3):337-343 (2005).

Beal, et al., "Second Structural Motif for Recognition of DNA by Oligonucleotide-Directed Triple-Helix Formation," Science, 251:1360-1363 (1992).

Becker et al., "Fertile transgenic wheat from microprojectile bombardment of scutellar tissue," The Plant Journal, 5(2):299-307 (1994).

Bhargava et al., "Long double-stranded RNA-mediated RNA interference as a tool to achieve site-specific silencing of hypothalamic neuropeptides," Brain Research Protocols, 13:115-125 (2004).

Boletta et al., "High Efficient Non-Viral Gene Delivery to the Rat Kidney by Novel Polycationic Vectors," J. Am Soc. Nephrol., 7:1728 (1996).

Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).

Bolter et al., "A chloroplastic inner envelope membrane protease is essential for plant development," FEBS Letters, 580:789-794 (2006).

Bourgeois et al., "Field and producer survey of ACCase resistant wild oat in Manitoba," Canadian Journal of Plant Science, 709-715 (1997).

Breaker et al., "A DNA enzyme with Mg2+-dependent RNA phosphoesterase activity," Chemistry and Biology, 2:655-660 (1995).

Brodersen et al., "The diversity of RNA silencing pathways in plants," Trends in Genetics, 22(5):268-280 (2006).

Brugiere et al., "Glutamine Synthetase in the Phloem Plays a Major Role in Controlling Proline Production," The Plant Cell, 11:1995-2011 (1999).

Busch et al., "RNAi for discovery of novel crop protection products," Pflanzenschutz-Nachrichten Bayer, 58(1):34-50 (2005).

Busi et al., "Gene flow increases the initial frequency of herbicide resistance alleles in unselectedpopulations," Agriculture, Ecosystems and Environments, Elsevier, Amsterdam, NL, 142(3):403-409 (2011).

Butler et al., "Priming and re-drying improve the survival of mature seeds of Digitalis purpurea during storage," Annals of Botany, 103:1261-1270 (2009).

Bytebier et al., "T-DNA organization in tumor cultures and transgenic plants of the monocotyledon *Asparagus officinalis*," Proc. Natl. Acad. Sci. U.S.A., 84:5345-5349 (1987).

Campbell et al., "Gene-knockdown in the honey bee mite *Varroa destructor* by a non-invasive approach: studies on a glutathione S-transferase," Parasites & Vectors, 3(1):73, pp. 1-10 (2010).

Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).

Chabbouh et al., "Cucumber mosaic virus in artichoke," FAO Plant Protection Bulletin, 38:52-53 (1990).

Chakravarty et al., "Genetic Transformation in Potato: Approaches and Strategies," Amer J Potato Res, 84:301 311 (2007).

Chang et al., "Cellular Internalization of Fluorescent Proteins via Arginine-rich Intracellular Delivery Peptide in Plant Cells," Plant Cell Physiol., 46(3):482-488 (2005).

Chee et al., "Transformation of Soybean (*Glycine max*) by Infecting Germinating Seeds with Agrobacterium tumefaciens," Plant Physiol., 91:1212-1218 (1989).

Chen et al., "In Vivo Analysis of the Role of atTic20 in Protein Import into Chloroplasts," The Plant Cell, 14:641-654 (2002).

Chen et al., "Transfection and Expression of Plasmid DNA in Plant Cells by an Arginine-Rich Intracellular Delivery Peptide without Protoplast Preparation," FEBS Letters 581, pp. 1891-1897 (2007).

Cheng et al., "Production of fertile transgenic peanut (*Arachis hypogaea* L.) plants using Agrobacterium tumefaciens," Plant Cell Reports, 15:653-657 (1996).

Chi et al., "The Function of RH22, a DEAD RNA Helicase, in the Biogenesis of the 50S Ribosomal Subunits of *Arabidopsis* Chloroplasts," Plant Physiology, 158:693-707 (2012).

Chupp et al., "Chapter 8: White Rust," Vegetable Diseases and Their Control, The Ronald Press Company, New York, pp. 267-269 (1960).

Clough et al., "Floral dip: a simplified method for Agrobacterium-mediated transformation of *Arabidopsis thaliana*," The Plant Journal, 16(6):735-743 (1998).

CN101914540 Patent Diclosure, "Introduction of RNA into plant by interference," (2010).

Colboume et al., "The Ecoresponsive Genome of Daphnia pulex," Science, 331(6017):555-561 (2011).

(56) References Cited

OTHER PUBLICATIONS

Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Concise Descriptions of Relevance filed by a third party on Nov. 29, 2012, in U.S. Appl. No. 13/042,856.
Cooney et al., "Site-Specific Oligonucleotide Binding Represses Transcription of the Human c-myc Gene in Vitro," Science, 241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," Breast Cancer Res. Treat, 115:545-560 (2009).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* Is Required for Posttranscriptional Gene Silencing Mediated by a Transgene but Not by a Virus," Cell, 101:543-553 (2000).
Davidson et al., "Engineering regulatory RNAs," Trends in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," The EMBO Journal, 7(5):1299-1305 (1988).
Desai et al., "Reduction in deformed wing virus infection in larval and adult honey bees (*Apis mellifera* L.) by double-stranded RNA ingestion," Insect Molecular Biology, 21(4):446-455 (2012).
Diallo et al., "Long Endogenous dsRNAs Can Induce Complete Gene Silencing in Mammalian Cells and Primary Cultures," Oligonucleotides, 13:381-392 (2003).
Dietemann et al., "Varroa destructor: research avenues towards sustainable control," Journal of Apicultural Research, 51(1):125-132 (2012).
Du et al., "A systematic analysis of the silencing effects of an active siRNA at all single-nucleotide mismatched target sites," Nucleic Acids Research, 33(5):1671-1677 (2005).
Dunoyer et al., "Small RNA Duplexes Function as Mobile Silencing Signals Between Plant Cells," Science, 328:912-916 (2010).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
European Cooperation in the field of Scientific and Technical Research—Memorandum of Understanding for COST Action FA0806 (2008).
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated Oct. 8, 2013, in European Patent Application No. 11753916.3.
Extended European Search Report dated Sep. 29, 2016, in European Patent Application No. 14778840.0.
Farooq et al., "Rice seed priming," IPRN, 30(2):45-48 (2005).
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Fukuhara et al., "Enigmatic Double-Stranded RNA in Japonica Rice," Plant Molecular Biology, 21:1121-1130 (1993).

(56) References Cited

OTHER PUBLICATIONS

Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral RNA silencing pathways in plants," The EMBO Journal, 28(5):545-555 (2009).
Further Examination Report dated May 16, 2014, in New Zealand Patent Application No. 601784.
Gaines et al., "Gene amplification confers glyphosate resistance in Amaranthus palmeri," Proc. Natl. Acad. Sci. USA, 107(3):1029-1034 (2010).
Gan et al., "Bacterially expressed dsRNA protects maize against SCMV infection," Plant Cell Rep, 11:1261-1268 (2010).
Gan et al., "Inhibition of Leaf Senescence by Autoregulated Production of Cytokinin," Science, 270:1986-1988 (1995).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1-9:e1003035 (2012).
Ge et al., "Rapid vacuolar sequestration: the horseweed glyphosate resistance mechanism," Pest Management Sci., 66:345-348 (2010).
GenBank Accession No. AY545657.1 (2004).
GenBank Accession No. CB377464, "CmaEl_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cant aining IPRO11005:Dihydropteroate synthase-like, MRNA sequence" (2006).
GenBank Accession No. EU024568, "Amaranthus hypochondriacus acetolactate synthase (Als) gene" (2007).
GenBank Accession No. EW765249, "ST020010B10C12 Normalized and subtracted western corn rootworm female head cDNA library Diabrotica virgifera virgifera cDNA clone STO20010B10C 12 5-, mRNA sequence," (2007).
GenBank Accession No. EW771198, "ST0200101310C12 Normalized and subtracted western corn rootworm female head cDNA library Diabrotica virgifera virgifera cDNA clone ST020010BIOC12 5-, mRNA sequence," (2007).
GenBank Accession No. FE348695, "CBIB7954.fwd CBIB_Daphnia_pulex_Chosen_One_Library_2 Daphnia pulex cDNA clone CB1B7954 5', mRNA sequence" (2011).
GenBank Accession No. F.1972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_B1PLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
GenEmbl Accession No. FJ861243 (2010).
Gong et al., "Silencing of Rieske iron-sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," Pest Manag Sci, 65(7):723-731 (2009).
Gudkov, "Minireview: The L7/L12 ribosomal domain of the ribosome: structural and functional studies," FEBS Letters, 407:253-256 (1997).
Gutensohn et al., "Functional analysis of the two *Arabidopsis* homologues of Toc34, a component of the chloroplast protein import apparatus," The Plant Journal, 23(6):771-783 (2000).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," Journal of Experimental Botany, 51:439-445 (2000).
Hamilton et al., "Guidelines for the Identification and Characterization of Plant Viruses," J. gen. Virol., 54:223-241 (1981).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature,481:244-251 (2002).
Hardegree, "Drying and storage effects on germination of primed grass seeds," Journal of Range Management, 47(3):196-199 (1994).
Harrison et al., "Does Lowering Glutamine Synthetase Activity in Nodules Modigy Nitrogen Metabolism and Growth of Lotus japonicus?," Plant Physiology, 133:253-262 (2003).
Heffer et al., "Rapid isolation of gene homologs across taxa: Efficient identification and isolation of gene orthologs from non-model organism genomes, a technical report," EvoDevo Journal, 2(7):1-5 (2011).
Herman et al., "A three-component dicamba O-demethylase from Pseudomonas maltophilia, strain DI-6: gene isolation, characterization, and heterologous expression," J. Biol, Chem., 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Himber et al., "Transitivity-dependant and -independent cell-to-cell movement of RNA silencing," The EMBO Journal, 22(17):4523-4533 (2003).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," Plant Physiol., 107(2):469-477 (1995).
Holtra et al., "Assessment of the Physiological Condition of *Salvinia natans* L. Exposed to Copper(II) Ions," Environ. Protect. Eng., 41:147-158 (2015).
Hsieh et al., "A library of siRNA duplexes targeting the phosphoinositide 3-kinase pathway: determinants of gene silencing for use in cell-based screens," Nucleic Acids Res., 32(3):893-901 (2004).
Huesken et al., "Design of a genome-wide siRNA library using an artificial neural network," Nature Biotechnology, 23(8): 995-1001 (2005).
Hunter et al., "RNA Interference Strategy to suppress Psyllids & Leafhoppers," International Plant and Animal Genome XIX, 15-19 (2011).

(56) References Cited

OTHER PUBLICATIONS

Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No, PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al "Engineered riboregulators enable post-transcriptional control of gene expression," Nature Biotechnology, 22(7):841-847 (2004).
Ji et al., "Regulation of small RNA stability: methylation and beyond," Cell Research, 22:624-636 (2012).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Jones-Rhoades et al., "MicroRNAs and Their Regulatory Roles in Plants," Annu. Rev. Plant Biol., 57:19-53 (2006).
Josse et al., "A DELLA in Disguise: SPATULA Restrains the Growth of the Developing *Arabidopsis* Seedling," Plant Cell, 23:1337-1351 (2011).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kam et al., "Nanotube Molecular Transporters: Internalization of Carbon Nanotube—Protein Conjugates into Mammalian Cells," J. Am. Chem. Soc., 126(22):6850-6851 (2004).
Kambiranda et al., "Relationship Between Acid Invertase Activity and Sugar Content in Grape Species," Journal of Food Biochemistry, 35:1646-1652 (2011).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," J. Amer. Soc. Hort. Sci., 117(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kim et al., "Optimization of Conditions for Transient Agrobacterium-Mediated Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Kirkwood, "Herbicides and Plants," Botanical Journal of Scotland, 46(3):447-462 (1993).
Kirkwood, "Use and Mode of Action of Adjuvants for Herbicides: A Review of some Current Work," Pestic Sci., 38:93-102 (1993).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Knudsen, "Promoter2.0: for the recognition of PolI promoter sequences," Bioinformatics, 15(5):356-361 (1999).
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Kusaba et al., "Low glutelin content1: A Dominant Mutation That Suppresses the Glutelin Multigene Family via RNA Silencing ni Rice," The Plant Cell, 15(6):1455-1467 (2003).
Kusaba, "RNA interference in crop plants," Curr Opin Biotechnol, 15(2):139-143 (2004).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Lein et al., "Target-based discovery of novel herbicides," Current Opinion in Plant Biology, 7:219-225 (2004).
Leopold et al., "Chapter 4: Moisture as a Regulator of Physiological Reaction in Seeds," Seed Moisture, CSSA Special Publication No. 14, pp. 51-69 (1989).

(56) References Cited

OTHER PUBLICATIONS

Lermontova et al., "Reduced activity of plastid protoporphyrinogen oxidase causes attenuated photodynamic damage during high-light compared to low-light exposure," The Plant Journal, 48(4):499-510 (2006).

Lesnik et al., "Prediction of rho-independent transcriptional terminators in Escherichia coli," Nucleic Acids Research, 29(17):3583-3594 (2001).

Li et al., "Establishment of a highly efficient transformation system for pepper (Capsicum annuum L.)," Plant Cell Reports, 21: 785-788 (2003).

Li et al., "The FAST technique: a simplified Agrobacterium-based transformation method for transient gene expression analysis in seedlings of Arabidopsis and other plant species," Plant Methods, 5(6):1-15 (2009).

Liu et al., "Carbon Nanotubes as Molecular Transporters for Walled Plant Cells," Nano Letters, 9(3):1007-1010 (2009).

Liu et at., "Comparative study on the interaction of DNA with three different kinds of surfactants and the formation of multilayer films," Bioelectrochemistry, 70:301-307 (2007).

Liu et al., "DNAzyme-mediated recovery of small recombinant RNAs from a 5S rRNA-derived chimera expressed in Escherichia coli," BMC Biotechnology, 10:85 (2010).

Liu et al., "Identification and Application of a Rice Senescence-Associated Promoter," Plant Physiology, 153:1239-1249 (2010).

Liu, "Influence of Sugars on the Foliar Uptake of Bentazone and Glyphosate," New Zealand Plant Protection, 55:159-162 (2002).

Llave et al., "Endogenous and Silencing-Associated Small RNAs in Plants," The Plant Cell, 14:1605-1619 (2002).

Lu et al., "Oligo Walk: an online siRNA design tool utilizing hybridization thermodynamics," Nucleic Acids Research, 36:W104-W108 (2008).

Lu et al., "RNA silencing in plants by the expression of siRNA duplexes," Nucleic Acids Res., 32(21):e171 (2004).

Luft, "Making sense out of antisense oligodeoxynucleotide delivery: getting there is half the fun," J Mol Med, 76:75-76 (1998).

Luque et al., "Water Permeability of Isolated Cuticular Membranes: A Structural Analysis," Archives of Biochemistry and Biophysics, 317(2):417-422 (1995).

Maas et al., "Mechanism and optimized conditions for PEG mediated DNA transfection into plant protoplasts," Plant Cell Reports, 8:148-149 (1989).

MacKenzie et al., "Transgenic Nicotiana debneyii expressing viral coat protein are resistant to potato virus S infection," Journal of General Virology, 71:2167-2170 (1990).

Maher III et al., "Inhibition of DNA binding proteins by oligonucleotide-directed triple helix formation," Science, 245(4919):725-730 (1989).

Makkouk et al., "Virus Diseases of Peas, Beans, and Faba Bean in the Mediterranean region," Adv Virus Res, 84:367-402 (2012).

Mandal et al., "Adenine riboswitches and gene activation by disruption of a transcription terminator," Nature Struct. Mol. Biol., 11(1):29-35 (2004).

Mandal et al., "Gene Regulation by Riboswitches," Nature Reviews | Molecular Cell Biology, 5:451-463 (2004).

Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).

Maori et al., "IAPV, a bee-affecting virus associated with Colony Collapse Disorder can be silenced by dsRNA ingestion," Insect Molecular Biology, 18(1):55-60 (2009).

Masoud et al., "Constitutive expression of an inducible β-I,3-glucanase in alfalfa reduces disease severity caused by the oomycete pathogen Phytophthora megasperma f. sp medicaginis, but does not reduce disease severity of chitincontaining fungi," Transge.

Matveeva et al., "Prediction of antisense oligonucleotide efficacy by in vitro methods," Nature Biotechnology, 16:1374-1375 (1998).

Meinke, et al., "Identifying essential genes in Arabidopsis thaliana," Trends Plant Sci., 13(9):483-491 (2008).

Meins et al., "RNA Silencing Systems and Their Relevance to Plant Development," Annu, Rev. Cell Dev. Biol., 21:297-318 (2005).

Melnyk et al., "Intercellular and systemic movement of RNA silencing signals," The EMBO Journal, 30:3553-3563 (2011).

Migge et al., "Greenhouse-grown conditionally lethal tobacco plants obtained by expression of plastidic glutamine synthetase antisense RNA may contribute to biological safety," Plant Science 153:107-112 (2000).

Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (19.

Misawa et al., "Functional expression of the Erwinia uredovora carotenoid biosynthesis gene crtI in transgenic plants showing an increase of (β-carotene biosynthesis activity and resistance to the bleaching herbicide norflurazon," The Plant Journal, 4(5):8.

Miura et al., "The Balance between Protein Synthesis and Degradation in Chloroplasts Determines Leaf Variegation in Arabidopsis yellow variegated Mutants," The Plant Cell, 19:1313-1328 (2007).

Molina et al., "Inhibition of protoporphyrinogen oxidase expression in Arabidopsis causes a lesion-mimic phenotype that induces systemic acquired resistance," The Plant Journal, 17(6):667-678 (1999).

Molnar et al., "Plant Virus-Derived Small Interfering RNAs Originate redominantly from Highly Structured Single-Stranded Viral RNAs," Journal of Virology, 79(12):7812-7818 (2005).

Molnar et al., "Small Silencing RNAs in Plants Are Mobile and Direct Epigenetic Modification in Recipient Cells," Science, 328:872-875 (2010).

Mora et al., "How Many Species Are There on Earth and in the Ocean?," PLOS Biol., 9(8):e100127, p. 1-8 (2011).

Moriyama et al., "Double-stranded RNA in rice: a novel RNA replicon in plants," Molecular & General Genetics, 248(3):364-369 (1995).

Moriyama et al., "Stringently and developmentally regulated levels of a cytoplasmic double-stranded RNA and its high-efficiency transmission via egg and pollen in rice," Plant Molecular Biology, 31:713-719 (1996).

Morrissey et al., "Potent and persistent in vivo anti-HBV activity of chemically modified siRNAs," Nat Biotechnol. 23(8):1002-1007 (2005).

Moser et al., "Sequence-Specific Cleavage of Double Helical DNA by Triple Helix Formation," Science, 238:645-646 (1987).

Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).

Non-Final Office Action dated Apr. 11, 2013, in U.S. Appl. No. 13/042,856.

Non-Final Office Action dated Apr. 29, 2016, in U.S. Appl. No. 13/583,302.

Non-Final Office Action dated Aug. 10, 2016, in U.S. Appl. No. 13/612,995.

Non-Final Office Action dated Aug. 12, 2015, in U.S. Appl. No. 13/612,936.

Non-Final Office Action dated Aug. 13, 2015, in U.S. Appl. No. 13/612,929.

Non-Final Office Action dated Aug. 19, 2016, in U.S. Appl. No. 13/612,925.

Non-Final Office Action dated Aug. 19, 2016, in U.S. Appl. No. 13/612,929.

Non-Final Office Action dated Aug. 3, 2016, in U.S. Appl. No. 14/015,715.

Non-Final Office Action dated Aug. 5, 2016, in U.S. Appl. No. 14/015,785.

Non-Final Office Action dated Aug. 8, 2016, in U.S. Appl. No. 13/612,936.

Non-Final Office Action dated Dec. 17, 2015, in U.S. Appl. No. 14/532,596.

Non-Final Office Action dated Feb. 10, 2016, in U.S. Appl. No. 13/901,326.

Non-Final Office Action dated Feb. 23, 2016, in U.S. Appl. No. 14/603,347.

(56) References Cited

OTHER PUBLICATIONS

Non-Final Office Action dated Feb. 23, 2016, in U.S. Appl. No. 14/608,951.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. I, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
Nowak et al., "A new and efficient method for inhibition of RNA viruses by DNA interference," The FEBS Journal, 276:4372-4380 (2009).
Office Action dated Apr. 13, 2016, in Chinese Patent Application No. 201280053985.3.
Office Action dated Aug. 25, 2016, in Eurasian Patent Application No. 201201264.
Office Action dated Aug. 28, 2013, in Chinese Patent Application No. 201180012795.2.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Feb. 17, 2014, in Mexican Patent Application No. MX/a/2012/010479.
Office Action dated Feb. 24, 2014, in Eurasian Patent Application No. 201201264.
Office Action dated Jul. 18, 2016, in Indonesian Patent Application No. W00201203610.
Office Action dated Jul. 23, 2015, in Ukrainian Patent Application No. 201211548.
Office Action dated Jun. 20, 2016, in Chinese Patent Application No. 201280054819.5.
Office Action dated Jun. 24, 2016, in Chinese Patent Application No. 201280053984.9.
Office Action dated Nov. 15, 2016, in Mexican Patent Application. No. MX/a/2014/003068.
Office Action dated Sep. 5, 2016, in Ukrainian Patent Application No. a 2014 03846.
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of Brassica Napus Have Divergent Patterns of Expression," The Plant Journal, Blackwell Scientific Publications, Oxford, GB, 2(3):321-330 (1992).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc, Hort. Sci., 119(3):629-635 (1994).
Partial Supplementary European Search Report dated Mar. 2, 2015, in European Patent Application No. 12 831 494.5.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by Arabidopsis induces changes in the expression of CLE peptides which control root morphology," Plant Signaling & Behavior, 5(9):1112-1114 (2010).
Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Pornprom et al., "Glutamine synthetase mutation conferring target-site-based resistance to glufosinate in soybean cell selections," Pest Manag Sci, 2009; 65(2):216-222 (2009).
Pratt et al., "Amaranthus rudis and *A. tuberculatus*, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).

(56) References Cited

OTHER PUBLICATIONS

Promoter Prediction for SEQ ID No. 8 from 13/612,925/MK/, Promoter 2.0 Prediction Results, pp. 1-6 (2016).
Qiwei,"Advance in DNA interference," Progress in Veterinary Medicine, 30(1):71-75 (2009).
Rajur et al., "Covalent Protein—Oligonucleotide Conjugates for Efficient Delivery of Antisense Molecules," Bioconjug Chem., 8:935-940 (1997).
Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Reither et al., "Specificity of DNA triple helix formation analyzed by a FRET assay," BMC Biochemistry, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 13, 2016, in U.S. Appl. No. 14/206,707.
Restriction Requirement dated Oct. 2, 2012, in U.S. Appl. No. 13/042,856.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Ruan et al., "Suppression of Sucrose Synthase Gene Expression Represses Cotton Fiber Cell Initiation, Elongation, and Seed Development," The Plant Cell; 15:952-964 (2003).
Ryabov et al., "Cell-to-Cell, but Not Long-Distance, Spread of RNA Silencing That Is Induced in Individual Epidermal Cells," Journal of Virology, 78(6):3149-3154 (2004).
Ryan, "Human endogenous retroviruses in health and disease: a symbiotic perspective," Journal of the Royal Society of Medicine, 97:560-565 (2004).
Salanenka et al., "Seedcoat Permeability: Uptake and Post-germination Transport of Applied Model Tracer Compounds," HortScience, 46(4):622-626 (2011).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. *columbia*," Nucleic Acids Research, 18(8):2188-2193 (1990).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Schwember et al., "Drying Rates following Priming Affect Temperature Sensitivity of Germination and Longevity of Lettuce Seeds," HortScience, 40(3):778-781 (2005).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. *Aggregatum*) and carrot (*Daucus carota*)," Journal of Agricultural Technology, 7(3):857-867 (2011).
Senthil-Kumar et al., "A systematic study to determine the extent of gene silencing in Nicotiana benthamiana and other *Solanaceae* species when heterologous gene sequences are used for virus-induced gene silencing," New Phytologist, 176:782-791 (2007).
Shaoquan, "The action target of herbicide and the innovation of a new variety," Chemical Industry Press, pp. 23-24 (2001).
Sharma et al., "A simple and efficient Agrobacterium-mediated procedure for transformation of tomato," J. Biosci., 34(3):423 433 (2009).
Shintani et al., "Antisense Expression and Overexpression of Biotin Carboxylase in Tobacco Leaves," Plant Physiol 114:881-886 (1997).
Showalter, "Structure and Function of Plant Cell Wall Proteins," The Plant Cell, 5:9-23 (1993).
Sijen et al., "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," Weed Biology and Management, 8:104-111 (2008).
Snead et al., "Molecular basis for improved gene silencing by Dicer substrate interfering RNA compared with other siRNA variants," Nucleic Acids Research, 41(12):6209-6221 (2013).
Song et al., "Herbicide," New Heterocyclic Pesticide, Chemical Industry Press, 354-356 (2011).

(56) References Cited

OTHER PUBLICATIONS

Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—Silwet® Organosilicone Surfactants Have Physical and Physiological Properties Which Enhance the Performance of Sprays," Proceedings of the 9th Australian Weeds Conference, pp. 327-331 (1990).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street, "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Sun et al., "A Highly efficient Transformation Protocol for Micro-Tom, a Model Cultivar for Tomato Functional Genomics," Plant Cell Physiol., 47(3):426-431 (2006).
Sun et al., "Antisense oligodeoxynucleotide inhibition as a potent strategy in plant biology: identification of SUSIBA2 as a transcriptional activator in plant sugar signalling," The Plant Journal, 44:128-138 (2005).
Sun et al., "Sweet delivery—sugar translocators as ports of entry for antisense oligodeoxynucleotides in plant cells," The Plant Journal, 52:1192-1198 (2007).
Sutton et al., "Activity of mesotrione on resistant weeds in maize," Pest Manag. Sci., 58:981-984 (2002).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Temple et al., "Down-regulation of specific members of the glutamine synthetase gene family in Alfalfa by antisense RNA technology," Plant Molecular Biology, 37:535-547 (1998).
Templeton et al., "Improved DNA: liposome complexes for increased systemic delivery and gene expression," Nature Biotechnology, 15:647-652 (1997).
Tenllado et al., "Crude extracts of bacterially expressed dsRNA can be used to protect plants against virus infection," BMC Biotechnology, 3(3):1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.

Thomas et al., "Size constraints for targeting post-transcriptional gene silencing and for RNA-directed methylation in Nicotiana benthamiana using a potato virus X vector," The Plant Journal, 25(4):417-425 (2001).
Thompson, et al., "Clustal W: improving the sensitivity of progressive multiple sequence alignment through sequence weighting, position-specific gap penalties and weight matrix choice," Nucl. Acids Res., 22(22):4673-4680 (1994).
Timmons et al., "Specific interference by ingested dsRNA," Nature, 395:854 (1998).
Tomari et al., "Perspective: machines for RNAi," Genes & Dev., 19:517-529 (2005).
Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany.
Töpfer et al., "Uptake and Transient Expression of Chimeric Genes in Seed-Derived Embryos," Plant Cell, 1:133-139 (1989).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Urayama et al., "Knock-down of OsDCL2 in Rice Negatively Affects Maintenance of the Endogenous dsRNA Virus, *Oryza sativa* Endornavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA," Cell, 95:177-187 (1998).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).

(56) References Cited

OTHER PUBLICATIONS

Wang et al., "Foliar uptake of pesticides-Present status and future challenge," ScienceDirect, 87:1-8 (2007).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Welch et al., "Expression of ribozymes in gene transfer systems to modulate target RNA levels," Curr Opin Biotechnol. 9(5):486-496 (1998).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot, Noxious Weed Control Board (NWCB) of Washington State (2010) <www.nwcb.wa.gov/detail.asp?weed=46>.
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Written Opinion dated Apr. 7, 2016, in Singapore Patent Application No. 201206152-9.
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Sinding Domain of Rac1 GTPase, Plos One, 7(8)1-12:e42975 (2012).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "A novel rice gene, NRR responds to macronutrient deficiency and regulates root growth," Mol Plant, 5(1):63-72 (2012).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).
Zhang et al., "Chapter 10: New Characteristics of Pesticide Research & Development," New Progress of the world agriculture chemicals, p. 209 (2010).
Zhang et al., "DEG: a database of essential genes," Nucleic Acids Res., 32:D271-D272 (2004).
Zhang et al., "Development arid Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).
Zhang et al., "Transgenic rice plants produced by electroporation-mediated plasmid uptake into protoplasts," The Plant Cell Rep., 7:379-384 (1988).
Zhao et al., "Phyllotreta striolata (Coleoptera: Chrysomelidae):Arginine kinase cloning and RNAi-based pest control," European Journal of Entomology, 105(5):815-822 (2008).
Zhu et al., "Ingested RNA interference for managing the populations of the Colorado potato beetle, *Leptinotarsa decemlineata*," Pest Manag Sci, 67:175-182 (2010).
Ascencio-Ibanez et al., "DNA abrasion onto plants is an effective method for geminivirus infection and virus-induced gene silencing," Journal of Virological Methods, 142:198-203 (2007).
Bedell et al., "Sorghum Genome Sequencing by Methylation Filtration," PLOS Biology, 3(1):E13/104-115 (2005).
Burgos et al., "Review: Confirmation of Resistance to Herbicides and Evaluation of Resistance Levels," Weed Science, 61 (1):4-20 (2013).
Chen et al., "Exploring MicroRNA-Like Small RNAs in the Filamentous Fungus Fusarium oxysporum," PLOS One, 9(8):e104956:1-10 (2014).
Constan et al.,"An outer envelope membrane component of the plastid protein import apparatus plays an essential role in *Arabidopsis*," The Plant Journal, 38:93-106 (2004).
Di Stilio et al., "Virus-Induced Gene Silencing as a Tool for Comparative Functional Studies in Thalictrum," PLoS One, 5(8):e12064 (2010).
Eamens et al., "RNA Silencing in Plants: Yesterday, Today, and Tomorrow," Plant Physiology, 147(2):456-468 (2008).
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Friedberg, "Automated protein function prediction—the genomic challenge," Briefings in Bioinformatics, 7(3):225-242 (2006).
Funke et al., "Molecular basis for herbicide resistance in Roundup Ready crops," PNAS, 103:13010-13015 (2006).
Gallie et al., "Identification of the motifs within the tobacco mosaic virus 5'-leader responsible for enhancing translation," Nucleic Acids Res., 20(17):4631-4638 (1992).
Gan et al., "Bacterially expressed dsRNA protects maize against SCMV infection," Plant Cell Rep, 29(11):1261-1268 (2010).
Gaskin et al., "Novel organosillicone adjuvants to reduce agrochemical spray volumes on row crops," New Zealand Plant Protection, 53:350-354 (2000).
GenBank Accession No. EF143582 (2007).
Hagio, "Chapter 25: Direct Gene Transfer into Plant Mature Seeds via Electroporation After Vacuum Treatment," Electroporation and Sonoporation in Developmental Biology, p. 285-293 (2009).
Hess, "Surfactants and Additives," 1999 Proceedings of the California Weed Science Society, 51:156-172 (1999).
Huang et al., "In Vivo Analyses of the Roles of Essential Omp85-Related Proteins in the Chloroplast Outer Envelope Membrane," Plant Physiol., 157:147-159 (2011).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Kikkert et al., "Stable Transformation of Plant Cells by Particle Bombardment/Biolistics," Methods in Molecular Biology, 286:61-78 (2005).
Kumar et al., "Sequencing, De Novo Assembly and Annotation of the Colorado Potato Beetle, *Leptinotarsa decemlineata*, Transcriptome," PLoS One, 9(1):e86012 (2014).
Li et al., "A Simplified Seed Transformation Method for Obtaining Transgenic *Brassica napus* Plants," Agricultural Sciences in China, 8(6):658-663 (2009).
Liu et al, "The Helicase and RNasellla Domains of *Arabidopsis* Dicer-Like1 Modulate Catalytic Parameters during MicroRNA Biogenesis," Plant Physiology, 159:748-758 (2012).
McGinnis, "RNAi for functional genomics in plants," Brief Funct Genomics, 9(2):111-7 (2010).

(56) References Cited

OTHER PUBLICATIONS

Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 6, 2017, in Mexican Patent Application No. MX/a/2015/013103 (with English translation).
Office Action dated Mar. 16, 2017, in Chinese Patent Application No. 201280054819.5.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 6, 2017, in Chinese Patent Application No. 2014800154012 (with English translation).
Paddison et al., "Stable suppression of gene expression by RNAi in mammalian cells," Proc. Natl Acad. Sci. USA, 99(3):1443-1448 (2002).
Patent Examination Report No. 1 dated Jun. 8, 2017, in Australian Patent Application No. 2012308686.
Powles et al., "Evolution in Action: Plants Resistant to Herbicides," Annual Review of Plant Biology, 61(1):317-347 (2010).
Rakoczy-Trojanowska, "Alternative Methods of Plant Transformation—a short review," Cellular & Molecular Biology Letters, 7:849-858 (2002).
Regalado, "The Next Great GMO Debate," MIT Technology Review,pp. 1-19 (2015) <https://www.technologyreview.com/s/540136/the-next-great-gmo-debate/>.
Richardson et al., "Targeting and assembly of components of the TOC protein import complex at the chloroplast outer envelope membrane," Frontiers in Plant Science, 5:1-14 (2014).
Search Report dated Jul. 24, 2017, in Chinese Patent Application No. 201480014392.5 (with English translation).
Small, "RNAi for revealing and engineering plant gene functions," Current Opinion in Biotechnology, 18:148-153 (2007).
Statement of Grounds and Particulars dated Sep. 1, 2017, in Australian Patent No. 2014262189.
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," New Zealand Journal of Forestry Science, 24:27-34 (1994).
Summons to Attend Oral Proceedings Pursuant to Rule 115(1) EPC, dated Aug. 7, 2017, in European Patent Application No. 12832160.1.
Toriyama et al., "Transgenic Rice Plants After Direct Gene Transfer Into Protoplasts," Bio/Technology, 6:1072-1074 (1988).
Trucco et al.," Amaranthus hybridus can be pollinated frequently by A. tuberculatus under filed conditions," Heredity, 94:64-70 (2005).
Voinnet, "Origin, Biogenesis, and Activity of Plant MicroRNAs," Cell, 136:669-687 (2009).
Wool et al., "Structure and evolution of mammalian ribosomal proteins," Biochem. Cell Biol., 73:933-947 (1995).
Written Opinion dated Mar. 6, 2017, in Singaporean Patent Application No. 2012061529.
Xu et al., "Characterization and Functional Analysis of the Calmodulin-Binding Domain of Rac1 GTPase," PLoS One, 7(8):e42975 (2012).
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Yue et al., "Vertical-transmission routes for deformed wing virus of honeybees (*Apis mellifera*)," Journal of General Virology, 88:2329-2336 (2007).
Anonymous, "Resistant Weeds Spur Research Into New Technologies," Grains Research & Development Corporation, 2013.
Asad et al., "Silicon Carbide Whisker-mediated Plant Transformation," Properties and Applications of Silicon Carbide, pp. 345-358 (2011).
Baker, "Chlorophyll Fluorescence: A Probe of Photosynthesis In Vivo," Annu. Rev. Plant Biol., 59:89-113 (2008).
Bauer et al., "The major protein import receptor of plastids is essential for chloroplast biogenesis," Nature, 403:203-207 (2000).
Baulcombe, "RNA silencing in plants," Nature, 431:356-363 (2004).
Baum et al., "Progress Towards RNAi-Mediated Insect Pest Management," Advances in Insect Physiology, 47:249-295 (2014).
Belhadj et al., "Methyl Jasmonate Induces Defense Responses in Grapevine and Triggers Protection against Erysiphe necator," J. Agric Food Chem., 54:9119-9125 (2006).
Burleigh, "Relative quantitative RT-PCR to study the expression of plant nutrient transporters in arbuscular mycorrhizas," Plant Science, 160:899-904 (2001).
Chang et al., "Dual-target gene silencing by using long, sythetic siRNA duplexes without triggering antiviral responses," Molecules and Cells, 27(6)689-695 (2009).
Cheng et al., "Transient Expression of Minimum Linear Gene Cassettes in Onion Epidermal Cells Via Direct Transformation," Appl Biochem Biotechnol, 159:739-749 (2009).
Christiaens et al., "The challenge of RNAi-mediated control of hemipterans," Current Opinion in Insect Science, 6:15-21 (2014).
Communication Pursuant to Article 94(3) EPC dated Sep. 5, 2018, in European Patent Application No. 17152830.0.
Cong et al., "Multiplex Genome Engineering Using CRISPR/Cas Systems," Science, 339:819-823 (2013).
Danka et al., "Field Test of Resistance to Acarapis woodi (Acari: Tarsonemidae) and of Colony Production by Four Stocks of Honey Bees (*Hymenoptera apidae*)" Journal of Economic Entomology, 88(3):584-591 (1995).
Database EMBL XP-002781749(BG442539) dated Mar. 20, 2001.
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Delye et al., "PCR-based detection of resistance to acetyl-CoA carboxylase-inhibiting herbicides in black-grass (*Alopecurus myosuroides* Huds) and ryegrass (*Lolium rigidum* Gaud)," Pest Management Science, 58:474-478 (2002).
Delye et al., "Variation in the gene encoding acetolactate-synthase in *Lolium* species and proactive detection of mutant, herbicide-resistant alleles," Weed Research, 49:326-336 (2009).
Desveaux et al., "PBF-2 Is a Novel Single-Stranded DNA Binding Factor Implicated in PR-10a Gene Activation in Potato," The Plant Cell, 12:1477-1489 (2000).

(56) References Cited

OTHER PUBLICATIONS

Dietzgen et al., "Transgenic gene silencing strategies for virus control," Australasian Plant Pathology, 35:605-618 (2006).
Dilpreet et al., "Glyphosate Rsistance in a Johnsongrass (*Sorghum halepense*) Biotype from Arkansas," Weed Science, 59(3):299-304 (2011).
Downey et al., "Single and dual parasitic mite infestations on the honey bee, *Apis mellifera* L.," Insectes Sociaux, 47(2):171-176 (2000).
Drobyazko R.V., "Reliable and environmentally friendly insecticide," Protection and quarantine of plants, 2012 (pp. 52, 53) (in Russian).
Duhoux et al., "Reference Genes to Study Herbicide Stress Response in *Lolium* sp.: Up-Regulation of P3450 Genes in Plants Resistant to Acetolactate-Synthase Inhibitors," Plos One, 8(5):e63576 (2013).
Egli et al., "A Maize Acetyl-Coenzyme A Carboxylase cDNA Sequence," Plant Physiol., 108: 1299-1300 (1995).
Eudes et al., "Cell-penetrating peptides," Plant Signaling & Behavior, 3(8):549-5550 (2008).
European Search Report dated Sep. 7, 2017, in European Patent Application No. 17152830.0.
Examination Report dated Mar. 1, 2018, in Australian Patent Application No. 2013264742.
Extended European Search Report dated Dec. 19, 2018, in European Patent Application No. 16804395.8.
Extended European Search Report dated Nov. 16, 2018, in European Patent Application No. 18182238.8.
Extended European Search Report dated Nov. 21, 2018, in European Patent Application No. 18175809.5.
Extended European Search Report dated Nov. 7, 2017, in European Patent Application No. 15811092.4.
Extended European Search Report dated Nov. 8, 2017, in European Patent Application No. 15737282.2.
Extended European Search Report dated Sep. 28, 2018, in European Patent Application No. 16740770.9.
Extended European Search Report dated Apr. 13, 2018, in European Patent Application No. 15812530.0.
Extended European Search Report dated Mar. 15, 2018, in European Patent Application No. 17181861.0.
Gao et al., "DNA-guided genome editing using the Natronobacterium gregoryi Argonaute," Nature Biotechnology, 34(7):768-773 (2016).
Gasser et al., "Structure, Expression, and Evolution of the 5-Enolpyruvylshikimate-3-phosphate Synthase Genes of Petunia and Tomato," J. Biol. Chem., 263: 4280-4287 (1988).
Gilmer et al., "Latent Viruses of Apple I. Detection with Woody Indicators," Plant Pathology, 1(10):1-9 (1971).
Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).
Guttieri et al., "DNA Sequence Variation in Domain A of the Acetolactate Synthase Genes of Herbicide-Resistant and -Susceptible Weed Biotypes," Weed Science, 40:670-679 (1992).
Hörmann et al., "Tic32, as Essential Component in Chloroplast Biogenesis," The Journal of Biological Chemistry, 279(33):34756-34762 (2004).
Horsch et al., "Inheritance of Functional Foreign Genes in Plants," Science, 223:496-498 (1984).
Hsu et al., "DNA targeting specificity of RNA-guided Cas9 nucleases," Nature Biotechnology, 31:827-832 (2013).
Hu et al., "High efficiency transport of quantum dots into plant roots with the aid of silwet L-77," Plant Physiology and Biochemistry, 48:703-709 (2010).
Huggett et al., "Real-time RT-PCR normalisation; strategies and considerations," Genes and Immunity, 6:279-284 (2005).
Inaba et al., "Arabidopsis Tic110 Is Essential for the Assembly and Function of the Protein Import Machinery of Plastids," The Plant Cell, 17:1482-1496 (2005).
International Search Report dated Oct. 13, 2016, in International Patent Application No. PCT/US2016/35500.
Jarvis et al, "An arabidopsis mutant defective in the plastid general protein import apparatus," Science, 282:100-103 (1998).
Jiang et al., Chapter III Seeds and Seedlings, Botany, Northwest A&F University Press, pp. 87-92 (2009).
Khanbekova et al., The defeat of the honey bee *Apis melifera caucasica* Gorb. By viruses and parasites, and condition of bee colonies in different ecogeographical conditions of Greater Caucasus, Agricultural Biology. 2013 (p. 43) (in Russian).
Kim et al., "Synthesis and characterization of mannosylated pegylated polyethylenimine as a carrier for siRNA," International Journal of Pharmaceutics, 427:123-133 (2012).
Kirkwood, "Recent developments in our understanding of the plant cuticle as a barrier to the foliar uptake of pesticides," Pestic Sci, 55:69-77 (1999).
Kovacheva et al., "Further in vivo studies on the role of the molecular chaperone, Hsp93, in plastid protein import," The Plant Journal, 50:364-379 (2007).
Kovacheva et al., "In vivo studies on the roles of Tic100, Tic40 and Hsp93 during chloroplast protein import," The Plant Journal, 41:412-428 (2005).
Li et at., "Long dsRNA but not siRNA initiates RNAi in western corn rootworm larvae and adults," Journal of Applied Entomology, 139(6):432-445 (2015).
Liu, "Calmodulin and Cell Cycle," Foreign Medical Sciences Section of Pathophysiology and Clinical Medicine, 18(4):322-324 (1998).
Liu, "Confocal laser scanning microscopy—an attractive tool for studying the uptake of xenobiotics into plant foliage," Journal of Microscopy, 213(Pt 2):87-93 (2004).
Liu, "The Transformation of Nucleic Acid Degradants in Plants," China Organic Fertilizers, Agriculture Press, ISBN: 7-1091634 (1991) (with English translation).
Lodish et al., Molecular Cell Biology, Fourth Edition, p. 210 (2000).
Lucas et al., "Plasmodesmata—bridging the gap between neighboring plant cells," Trends in Cell Biology, 19:495-503 (2009).
Masoud, "Constitutive expression of an inducible β-1,3-glucanase in alfalfa reduces disease severity caused by the oomycete pathogen *Phytophthora megasperma* f. sp *medicaginis* . . . ," Trans Res, 5:313-323 (1996).
Misawa, "Expression of an Erwinia phytoene desaturase gene not only confers multiple resistance to herbicides interfering with carotenoid biosynthesis but also alters xanthophyll metabolism . . . ," The Plant Jrnl, 6(4):481-489 (1994).
Misawa, "Functional expression of the Erwinia uredovora carotenoid biosynthesis gene crtI in transgenic plants showing an increase of β-carotene biosynthesis activity and resistance . . . ," The Plant Jrnl, 4(5):833-840 (1993).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Nemeth, "Virus, mycoplasma and rickettsia diseases of fruit trees," Martinus Nijhoff Publishers, 197-204 (1986).
Non-Final Office Action dated Mar. 21, 2018, in U.S. Appl. No. 13/619,980.
N-TER Nanoparticle siRNA, Sigma Aldrich TM website, Web. Nov. 20, 2014 <https://www.sigmaaldrich.com/life-science/custom-oligos/sirna-oligos/n-ter-nanoparticle.html>.
Office Action dated Aug. 9, 2018, in Canadian Patent Application No. 2,848,371.
Office Action dated Dec. 5, 2017, in Japanese Patent Application No. 2016-502033.
Office Action dated Feb. 21, 2018, in Mexican Patent Application No. MX/a/2015/012632 (with English translation).
Office Action dated Jul. 30, 2018, in Canadian Patent Application No. 2,848,576.
Office Action dated Mar. 8, 2018 (with English translation), in Chilean Patent Application No. 201403192.
Office Action dated Sep. 20, 2018, in Chilean Patent Application No. 201601440 (with English translation).
Partial European Search Report dated Jun. 29, 2018, in European Patent Application No. 18157745.3.

(56) References Cited

OTHER PUBLICATIONS

Partial European Search Report dated Dec. 6, 2017, in European Patent Application No. 17181861.0.
Partial Supplementary European Search Report dated Jan. 11, 2018, in European Patent Application No. 15812530.2.
Partial Supplementary European Search Report dated Jan. 11, 2018, in European Patent Application No. 15812530.0.
Pratt et al., "Sorghum Expressed Sequence Tags Identify Signature Genes for Drought, Pathogenesis, and Skotomorphogenesis from a Milestone Set of 16,801 Unique Transcripts," Plant Physiology, 139:869-884 (2005).
Qi et al., "RNA processing enables predictable programming of gene expression," Nature Biotechnology, 30:1002-1007 (2012).
Reverdatto et al., "A Multisubunit Acetyl Coenzyme A Carboxylase from Soybean," Plant Physiol., 119: 961-978 (1999).
Riar et al., "Glyphosate Resistance in a Johnsongrass (*Sorghum halepense*) Biotype from Arkansas," Weed Science, 59:299-304 (2011).
Sammataro et al., "Some Volatile Plant Oils as Potential Control Agents for Varroa Mites (*Acari varroidae*) in Honey Bee Colonies (*Hymenoptera apidae*)," American Bee Journal, 138(9):681-685 (1998).
Schönherr et al., "Size selectivity of aqueous pores in astomatous cuticular membranes isolated from *Populus canescens* (Aiton) Sm. Leaves," Planta, 219:405-411 (2004).
Search Report dated Oct. 20, 2017, in Chinese Patent Application No. 201380039346.6.
Simeoni et al., "Insight into the mechanism of the peptide-based gene delivery system MPG: implications for delivery of siRNA into mammalian cells," Nucleic Acids Research, 31(11):2717-2724 (2003).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Swans et al., "Argonaute of the archaeon *Pyrococcus furiosus* is a DNA-guided nuclease that targets cognate DNA," Nucleic Acid Res., 43(10):5120-5129 (2015).
Swans et al., "DNA-guided DNA interference by a prokaryotic Argonaute," Nature, 507(7491):258-61 (2014).
Teng et al., "Tic21 Is an Essential Translocon Component for Protein Translocation across the Chloroplast Inner Envelope Membrane," The Plant Cell, 18:2247-2257 (2006).
Tenllado et al., "Crude extracts of bacterially expressed dsRNA can be used to protect plants against virus infections," BMC Biotechnology, 3:1-11 (2003).
Tice, "Selecting the right compounds for screening: does Lipinski's Rule of 5 for pharmaceuticals apply to agrochemicals?" Pest Management Science, 57(1):3-16 (2001).
Tomlinson, "Evidence that the hexose-to-sucrose ratio does not control the switch to storage product accumulation in oilseeds: analysis of tobacco seed development and effects . . . ," Jrnl of Exper Bot, 55(406):2291-2303 (2004).
Townsend et al., "High frequency modification of plant genes using engineered zinc finger nucleases," Nature, 459:442-445 (2009).
TransIT-TKO® Transfection Reagent, Frequently Asked Questions, Web. 2019 <https://www.mirusbio.com/tech-resources/faqs/transit-tko-faqs>.
Ulrich et al., "Large scale RNAi screen in Tribolium reveals novel target genes for pest control and the proteasome as prime target," BMC genomics, 16(1):671 (2015).
Van der Meer et al., "Promoted analysis of the chalcone synthase (chs A) gene of Petunia hybrid: a 67 bp promoter region directs flower-specific expression," Plant Mol. Biol., 15:95-109 (1990).
Vila-Aiub et al., "Glyphosate resistance in perennial *Sorghum halepense* (Johnsongrass), endowed by reduced glyphosate translocation and leaf uptake," Pest Manag Sci, 68:430-436 (2012).
Wang et al., "Principle and technology of genetic engineering in plants," in Plant genetic engineering principles and techniques, Beijing: Science Press, pp. 313-315 (1998).
Watson et al., "RNA silencing platforms in plants," FEBS Letters, 579:5982-5987 (2005).
Yan et al., Seed Science, China Agriculture Press, pp. 101-103, Tables 2-37 (2001).
Yu et al., "Diversity of Acetyl-Coenzyme A Carboxylase Mutations in Resistant Lolium Populations: Evaluation Using Clethodim," Plant Physiology, 145:547-558 (2007).
Yu et al., "Glyphosate, paraquat and ACCase multiple herbicide resistance evolved in a Lolium rigidum biotype," Planta, 225:499-513 (2007).
Zabkiewicz, "Adjuvants and herbicidal efficacy—present status and future prospects," Weed Research, 40:139-149 (2000).
Zhang et al., "Progress in research of honey bee mite *Varro destructor*," Journal of Environmental Entomology, 34(3):345-353 (2012).
Zhao et al., "PsOr1, a potential target for RNA interference-based pest management," Insect Molecular Biology, 20(1):97-104 (2011).
Zhao et al., "Vegetable Statdardized Production Technology," Hangzhou: Zhejiang Science and Technology Press, p. 19 (2008).
Zhong et al., "A pea antisense gene for the chloroplast stromal processing peptidase yields seedling lethals in *Arabidopsis*: survivors show defective GFP import in vivo," The Plant Journal, 34:802-812 (2003).
Zidack et al., "Promotion of Bacterial Infection of Leaves by an Organosilicone Surfactant: Implications for Biological Weed Control," Biological Control, 2:111-117 (1992).
Zipperian et al., "Silicon Carbide Abrasive Grinding," Quality Matters Newsletter, PACE Technologies 1(2):1-3 (2002).
Zotti et al., "RNAi technology for insect management and protection of beneficial insects from diseases: lessons, challenges and risk assessments," Neotropical Entomology, 44(3):197-213 (2015).

\* cited by examiner

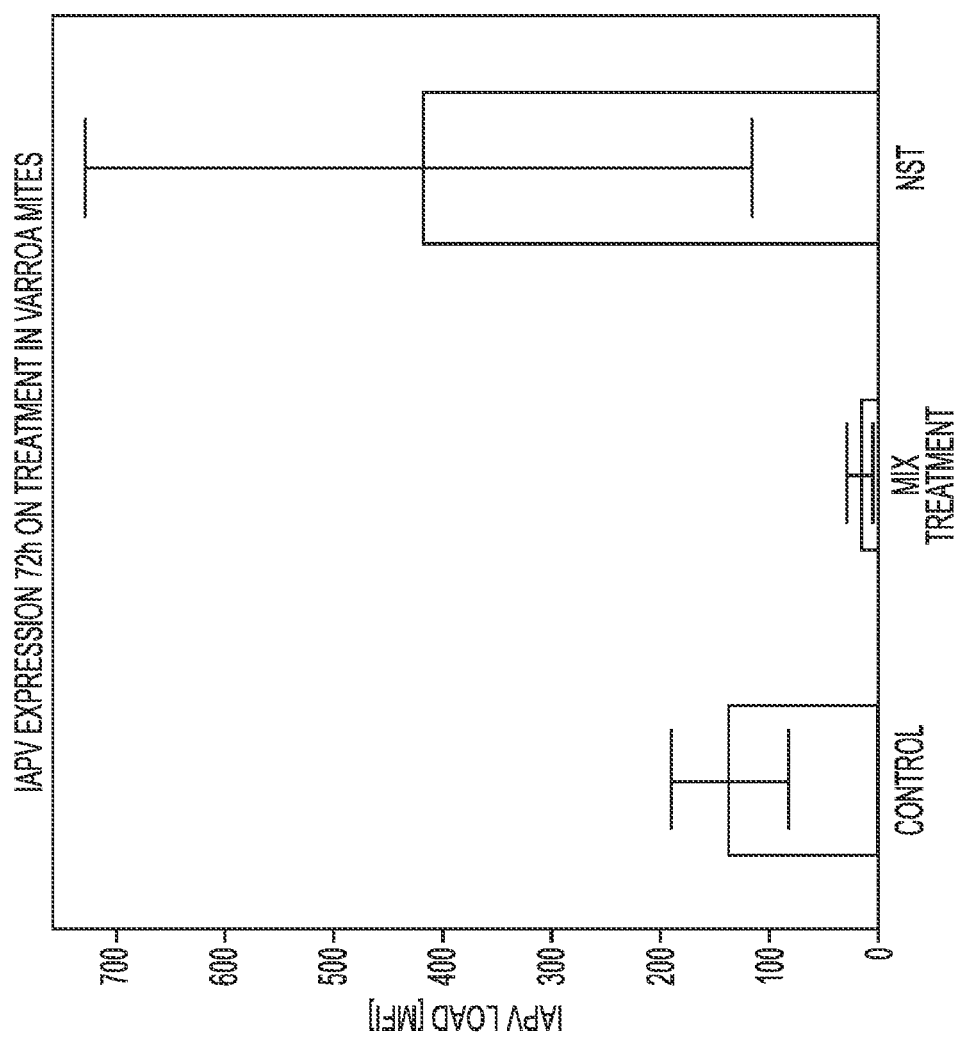

SEQUENCE LISTING

```
<160> NUMBER OF SEQ ID NOS: 24

<210> SEQ ID NO 1
<211> LENGTH: 293
<212> TYPE: RNA
<213> ORGANISM: Israeli acute paralysis virus

<400> SEQUENCE: 1
gauacauuga aagaugagcg ucgacccauu gaaaaaguua aucaauugaa aacacgagua     60
uucucaaaug gaccaaugga uuucucuaua gcuuuucgaa uguauuauuu gggcuuuaua    120
gcucauuuga uggaaaaucg aauuacuaau gaggugucca uuggaacgaa uguguauucu    180
caagacugga guaaaacugu ucguaaguug acuaaauuug gaaauaaagu uauugcaggu    240
gauuuuucaa cuuuugaugg aucacugaau guauguauua uggaaaaauu ugc           293

<210> SEQ ID NO 2
<211> LENGTH: 68
<212> TYPE: RNA
<213> ORGANISM: Israeli acute paralysis virus

<400> SEQUENCE: 2
gaaacuccaa auaggaucga uacccccaug gcucaggaua cuucaucggc uaggaacaug     60
gaugauac                                                               68

<210> SEQ ID NO 3
<211> LENGTH: 208
<212> TYPE: RNA
<213> ORGANISM: Israeli acute paralysis virus
```

<400> SEQUENCE: 3

```
gacggaccuu cacauauaac auaccccgua aucaauccug ugcaugaagu agaaguucca      60
uucuauucuc aguauaggaa aauaccuauc gcuucaacau cggauaaagg uuaugauucc     120
ucucuaaugu auuuucaaa uacagcaaca acucaaauug uugccagagc aggaaacgau      180
gacuuuaccu uugguuggau gauagguc                                        208
```

<210> SEQ ID NO 4
<211> LENGTH: 97
<212> TYPE: RNA
<213> ORGANISM: Israeli acute paralysis virus

<400> SEQUENCE: 4

```
gcccccuaga ugugcacugg gagacagaca aaucucccua guauggcua uagucuaaau      60 uuuucacaaa auuucaguuu agaccgaaaa ccgacac                              97
```

<210> SEQ ID NO 5
<211> LENGTH: 61
<212> TYPE: RNA
<213> ORGANISM: Deformed wing virus

<400> SEQUENCE: 5

```
gaagaaauau auagcuacgu gguguaguaa gcgucgugaa cauacugcug acuuugaucu      60
u                                                                     61
```

<210> SEQ ID NO 6
<211> LENGTH: 287
<212> TYPE: RNA
<213> ORGANISM: Deformed wing virus

<400> SEQUENCE: 6

```
gcucccaaug cugaagcgga ggaggcaagu gcuuggguau ccauuauuua uaauggugug      60
uguaauaugc uuaaugugc ugcucaaaaa ccgaaacaau uuaaagauug gguaaaauua     120
gcuacuguag auuuuaguaa uaauugaga gguaguaauc agguauuugu auuuucaag      180 aauacauuug aaguguugaa gaaaaugugg gguuauguau uuugucagag uaauccugca     240
gcgcguuugu ugaaagcugu gaaugacgag ccugagauuu ugaaagc                   287
```

<210> SEQ ID NO 7
<211> LENGTH: 53
<212> TYPE: RNA
<213> ORGANISM: Deformed wing virus

<400> SEQUENCE: 7

```
gaaagcugug aaugacgagc cugagauuuu gaaagcaugg gugaaggaau guc            53
```

<210> SEQ ID NO 8
<211> LENGTH: 129
<212> TYPE: DNA
<213> ORGANISM: Deformed wing virus

<400> SEQUENCE: 8

```
ggtacagttt accataccgt ttcgacagta ttacttagac tttatggcat cctatcgagc      60
tgcacgactt aatgctgagc atggtattgg tattgatgtt aacagcttag agtggacaaa     120
tttggcaac                                                             129
```

<210> SEQ ID NO 9
<211> LENGTH: 204

-continued

<212> TYPE: RNA
<213> ORGANISM: Deformed wing virus

<400> SEQUENCE: 9
gaauggauaa cuccugugua uauggcuaac cgucguaagg cgaaugaauc guuuaagaug 60
cguguagaug aaaugcaaau guuacguaug gaugaaccau uggaaggaga uaauauucuc 120
aauaaguaug uugaaguuaa ucagcgcuua guggaggaaa ugaaggcauu uaaggagcgu 180
acacuauggu cagauuuaca ucgc 204

<210> SEQ ID NO 10
<211> LENGTH: 110
<212> TYPE: RNA
<213> ORGANISM: Israeli acute paralysis virus

<400> SEQUENCE: 10
gaaacacaaa aucacaacgc uuuaaugaaa ggaugugguga aguuuauugu aaacuugcga 60
acucuucuca gaaccuuuag aacaauaaca gauaauugga uauuacaagc 110

<210> SEQ ID NO 11
<211> LENGTH: 277
<212> TYPE: RNA
<213> ORGANISM: Lake sinai virus

<400> SEQUENCE: 11
gcuuacaaua acuucguuca cagacaccgc guugcugccu augcugcugg cgugcguauc 60
caccguuacc gcacgccgug guauugcgcc gcgucacggu cuguuccggu cguccauccu 120
cuuaacuggu ugaugaccca guacgaucuu acuacuggcc auguucguga auuacuggau 180
cgacuggagg uugucaaugu uacccuucgu gauggccucc gcacuguugc ugacacugcg 240
uuuacagcuu auauguacua ucagauaaug uggugcu 277

<210> SEQ ID NO 12
<211> LENGTH: 253
<212> TYPE: RNA
<213> ORGANISM: Lake sinai virus

<400> SEQUENCE: 12
gagcaguauc uccucaauuu aaaauauguc cccucuacuu accgcuaucu caagcgcgau 60
cucgacauug acggugucca uaccgcguug uugggugagu uuaggucugu ucuuuacgcg 120
uaauuaauag aaauuaucac gaugaaucca ccaacuacga cuacgacuac gacgcgcacc 180
auccgcgccc caaaaguuca acugacgccc aauucugcua cucggcgucg gcguaaucgu 240
cggcgccguc gac 253

<210> SEQ ID NO 13
<211> LENGTH: 255
<212> TYPE: RNA
<213> ORGANISM: Lake sinai virus

<400> SEQUENCE: 13
gccugacuau uaugagauug auuacucccg auucgacuug ucuauuagug cugaaguuau 60
uucacaguac gagcaugccu gggucucucu uguuuauccu ccucucaauu acccuggcuu 120
cuggcagacu cucguuucga cacucauuac cucgggcuuu agugaguacg guauuacuua 180
cucuuugccu gggucacguu guagcgguga cccacauacg uccguuggua augguuugcu 240
gaacggguuc uuaac 255

<210> SEQ ID NO 14
<211> LENGTH: 262
<212> TYPE: RNA
<213> ORGANISM: Lake sinai virus

<400> SEQUENCE: 14

| gccucgugcg | gaccucauuu | cuucauguca | gugugugagc | augaugaguc | aauaccuacg | 60 |
| guguuccaug | cacacucggu | gggaggucaa | gauuaucccc | acgacauuga | uucagguuug | 120 |
| ggagcaauua | uaucaaaacg | cuuuagugcu | ucgcagcuac | gccuccuuag | cuggucuauc | 180 |
| gacggaauac | ucaacacuuu | aucucgcgcc | gccaccucau | cguuugucga | aucgucgcug | 240 |
| uuguccuugu | uacgauuuau | gc | | | | 262 |

<210> SEQ ID NO 15
<211> LENGTH: 257
<212> TYPE: RNA
<213> ORGANISM: Lake sinai virus

<400> SEQUENCE: 15

| gauuauaccg | gacuugggcu | ucaugcucaa | gaucgaucac | uaugagcaug | ucgacgauug | 60 |
| uucguuuugc | gguauguacu | ugcuggauga | ucguggaucg | cuccgcaugu | acucugaccc | 120 |
| ggugcgcaca | cugucauga | uacauguguc | cugcgccgau | ggucuacccca | acaauuugau | 180 |
| cguggccaag | gcucugagcc | uucucaaucu | gaauccaugu | accccaucg | ucacagccuu | 240 |
| uugucgucac | auauugc | | | | | 257 |

<210> SEQ ID NO 16
<211> LENGTH: 258
<212> TYPE: RNA
<213> ORGANISM: Lake sinai virus

<400> SEQUENCE: 16

| gagcauaaug | ccgcuggguu | acccuucuua | auuaagggau | gugacauggc | ggcucgugcc | 60 |
| gccaagaugc | gugaccuccu | ggguuggccu | cacuauuacg | agaucgacua | cucucguuuu | 120 |
| gauuugucga | uaagugcuga | ggucauaucu | caguuugagc | augcuuggau | ucucguugguc | 180 |
| uacgcccccg | acaugcaccc | gcuguucugg | cagacgcugg | ucgccacguu | ggucacuuca | 240 |
| ggguuuagug | aguauggc | | | | | 258 |

<210> SEQ ID NO 17
<211> LENGTH: 248
<212> TYPE: RNA
<213> ORGANISM: Lake sinai virus

<400> SEQUENCE: 17

| gagcaguauc | ugcucucauu | auuguuuguu | ccgucgcguu | augccuuacu | uaaacgagac | 60 |
| auugagcucg | acggccuaca | gaccacccuu | cuuggcgacu | ucaggucugu | ucuuuacgcg | 120 |
| ugaacauuau | aaauuuacua | ucaugaauca | acaacaaaug | aaccccgcgc | agcgaucguu | 180 |
| gcgccccgc | gcucaaucua | cucccucucg | guccgcucga | cgacgacgca | aucguaggcg | 240 |
| ccguaacc | | | | | | 248 |

<210> SEQ ID NO 18
<211> LENGTH: 255
<212> TYPE: RNA
<213> ORGANISM: Lake sinai virus

<400> SEQUENCE: 18

```
gccuggcuuc ggcaguauuu gaacccuaug ggcccuucua cauccagugu gaguggcuuu      60
ccugaugggu cugcuguuac cacaugcauu gccgauuaca ccaacacauu caauaucucu     120
uucccuccuc gugaggcgau uuauuguacc gguucuaauu cugaugagaa accguuaug     180 cuggacgccg ccaccuaugc uaagaucgac gcguggacua agucggauau caccugugc     240 auacucgccu ugccc                                                     255
```

```
<210> SEQ ID NO 19
<211> LENGTH: 257
<212> TYPE: RNA
<213> ORGANISM: Lake sinai virus

<400> SEQUENCE: 19
guccuauguu uacuugccga acguugacaa gcaccuuucu gcugcccggg gauaccgcuu      60
acugucccgc ggcaucacug guaucuuuag ugcuccugcu cuugagacuc agggauucgu     120
cacagcuugc caguauuugg cugagggguc uauacaaucu cagccauua agucugacgc     180 uguucgaucc gucacuguua acagugaugg uacuguuaag aacguugagu cuagcucaca     240
aacaguuucg ucuaugc                                                    257
```

```
<210> SEQ ID NO 20
<211> LENGTH: 255
<212> TYPE: RNA
<213> ORGANISM: Lake sinai virus

<400> SEQUENCE: 20
gagggcaucu caccuaaauu uucucucaaa cuuaagacuc gaacuguauu gcaauauauu      60
cccaccuccg gcucugucuu ggcuaacuuc accagacacg agccuacuua cgaucagaua     120
gcgcucgaug cugcugaucg ucugcguaac cugaugcccuc acgcuuaccc ugccgcauac     180
aacgauuggg gauggcuugg ugaucugcuc gauucugcca ucccaugcuu gccgggugua     240
gguacugugu auaac                                                      255
```

```
<210> SEQ ID NO 21
<211> LENGTH: 104
<212> TYPE: DNA
<213> ORGANISM: Deformed wing virus

<400> SEQUENCE: 21
gaaaatctgg ggttatgtat tttctcagag taatcctgca gcgcgtttgt tgaaagctgt      60
gaatgacgag cctgagattt tgaaagcaag ggtcaaggaa tgtc                      104
```

```
<210> SEQ ID NO 22
<211> LENGTH: 207
<212> TYPE: RNA
<213> ORGANISM: Solanum lycopersicum

<400> SEQUENCE: 22
gggagcaauu gaaaagugu ugaacucuau uaaacagauu aacccgaaga uuguuacucu       60
uguugagcaa gaagcgaauc auaacgcagg gguuuuauu gauagauuua acgaagcuuu     120
gcauuauuac ucaaccaugu uugauucguu agaaagcucu gggucuucgu cuucagcuuc     180 accaacugggg auucuuccuc aaccucc                                        207
```

```
<210> SEQ ID NO 23
<211> LENGTH: 310
<212> TYPE: DNA
```

-continued

```
<213> ORGANISM: Solanum lycopersicum

<400> SEQUENCE: 23
ggtgaacaat caagatttgg tgatgtcgga ggtttattta gggagacaga tttgtaacgt      60
ggtggcttgt gaaggttcag atcgagttga acgacatgaa acactgaatc aatggagggt     120
taggatgaac tcatctgggt tcgatccggt tcatctgggt tcaaatgcgt tcaaacaagc     180
ttccatgctt ttagctctgt tcgccggcgg cgatggttac agggtggaag aaaacgatgg     240
gtgtcttatg ttggggtggc atacacggcc acttatagct acctccgcct ggaagctatt     300
gccggactcc                                                            310

<210> SEQ ID NO 24
<211> LENGTH: 274
<212> TYPE: RNA
<213> ORGANISM: Unknown
<220> FEATURE:
<223> OTHER INFORMATION: Description of Unknown: Polynucleotide
      sequence

<400> SEQUENCE: 24
auacuuacug gugcuaauuu uuaucgagga ugcccaacuc cccccacuuu aaaacugcga      60
ucauacuaac gaacucccga aggagugaaa ggugucuaug uugagcuuaa uaaccuaccu     120
ugcgagcaaa gaaggacuag uugacccugg gcacccuaua uuguuauguu guuucgaacu     180
gaguuggcac ccaugcugca caugcaacaa acaugucggc cuucgugucu auccuagaaa     240
aguaccugug aacuuggcug ucuacaucau cauc                                 274
```

COMPOSITIONS AND METHODS FOR VIRUS CONTROL IN *VARROA* MITE AND BEES

CROSS-REFERENCE TO RELATED APPLICATIONS

This application is a U.S. National Stage Application of PCT/US2014/069353, filed on Dec. 9, 2014, which claims the benefit of U.S. Provisional Application No. 62/069,142, filed on Oct. 27, 2014, and also claims the benefit of U.S. Provisional Application No. 61/913,917, filed on Dec. 10, 2013, which are incorporated by reference in their entirety herein.

INCORPORATION OF SEQUENCE LISTING

A computer readable form of a sequence listing is filed with this application by electronic submission and is incorporated into this application by reference in its entirety. The sequence listing is contained in the file named P34159US02_SEQ.txt, which is 9,785 bytes in size (measured in operating system MS windows) and was created on Jun. 10, 2016.

FIELD

The present embodiments relate generally to compositions and methods for reducing the susceptibility of bees to infectious disease using RNA interference technology, and more particularly, to the use of RNA interference technology for reducing viral load and suppressing viral replication in the *Varroa* mite vector and in the bees.

BACKGROUND

Honeybees, *Apis mellifera*, are required for the effective pollination of crops and are therefore critical to world agriculture. Honeybees also produce economically important products, including honey and bees wax. The health and vigor of honeybee colonies are threatened by numerous parasites and pathogens, including viruses, bacteria, protozoa, and mites, each with characteristic modes of transmission.

In general, transmission of viruses can occur via two pathways: horizontal and vertical transmission. In horizontal transmission, viruses are transmitted among individuals of the same generation, while vertical transmission occurs from adults to their offspring. Transmission can occur through multiple routes in social organisms (for a detailed review see Chen Y P, et al (2006) Appl Environ Microbiol. 72(1):606-11). Recently, horizontal transmission of honeybee viruses has been documented in bee colonies, for example, transmission of deformed wing virus (DWV) and Kashmir Bee Virus (KBV) by the parasitic mite *Varroa destructor*, as well as some evidence of virus in honeybee eggs and young larvae, life stages not parasitized by *Varroa* mites.

*Varroa* (*Varroa destructor*) mites are the number one parasite of managed honey bees (*Apis mellifera*) and the biggest global threat to commercial beekeeping (Rosenkranz et al. 2010). *Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. Some bee viruses are known to replicate in the mite, thus dramatically increasing the viral load. If left untreated *Varroa* infestations typically result in colony-level mortality.

Currently, beekeepers use a plethora of methods to control *Varroa* levels that include various chemical miticides, most of which have lost efficacy and are toxic and/or leave residues in wax and honey. Other methods include application of oxalic or formic acid, monoterpenes (thymol) and a variety of other management practices, with highly variable outcomes, including toxicity to the treated colonies. Breeding of bees for resistance to *Varroa*, such as selection for Hygienic behavior which results in the removal of infested brood, has provided a limited practical success.

Current methods of treating *Varroa* infestations are proving to be ineffective as the mites develop resistance to existing miticides. In addition, the use of such miticides may introduce injurious chemicals into honey that is intended for human consumption.

SUMMARY

The present embodiments relate to compositions and methods for controlling viral load and/or viral replication in *Varroa* mites and honeybees.

The present disclosure provides a method for reducing viral load or suppressing viral replication in a *Varroa destructor* mite or in a bee colony, the method comprising providing to the *Varroa destructor* mite or the bee colony a composition comprising an effective amount of at least one trigger polynucleotide comprising a nucleic acid sequence that is essentially identical or essentially complementary to a sequence of at least 21 contiguous nucleotides of a bee viral gene, thereby reducing viral load or suppressing viral replication in the *Varroa destructor* mite or in the bee colony. In some embodiments, the virus is selected from the group consisting of: Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), Kakugo Virus (KV), and Laker Sinai Virus (LSV).

The present disclosure also provides a composition for providing to a *Varroa destructor* mite, a bee, or a bee colony, comprising an effective amount of a trigger polynucleotide comprising a nucleic acid sequence that is essentially identical or essentially complementary to a sequence of at least 21 contiguous nucleotides of a bee viral gene. In some embodiments, the composition reduces viral load or suppresses viral replication in the *Varroa destructor* mite, the bee, or the bee colony. In some embodiments, the composition increases the tolerance of a bee or a bee colony to a disease caused by the bee virus.

In some embodiments, the trigger polynucleotide is single-stranded DNA (ssDNA), single-stranded RNA (ssRNA), double-stranded RNA (dsRNA), double-stranded DNA (dsDNA), or double stranded DNA-RNA hybrid.

In some embodiments, the trigger polynucleotide down-regulates the viral gene. In some embodiments, the viral gene encodes a coat protein, RdRp, VP1, VP2, or helicase. In some embodiments, the trigger polynucleotide comprises a nucleic acid sequence having at least about 80%, 85%, 88%, 90%, 92%, 95%, 96%, 97%, 98%, or 99% sequence identity or complementarity, or having 100% sequence identity or complementarity to a sequence selected from the group consisting of SEQ ID NOs:1-21, or a fragment thereof. In some embodiments, the trigger polynucleotide comprises a mixture of 2, 3, 4, 5, 6, 7, 8, 9, or 10 different trigger polynucleotides, which target different viruses, or target different genes of the same virus, or target different fragments of a viral gene.

The present disclosure also provides a method for reducing viral load in a bee colony, the method comprising reducing viral load in a parasite of the bee colony by providing to the parasite a composition comprising an effective amount of a trigger polynucleotide comprising a nucleic acid sequence that is essentially identical or essentially complementary to a sequence of at least 21 contiguous nucleotides of a bee viral gene, thereby suppressing viral replication in the parasite and reducing the viral load in the bee colony. In some embodiments, the parasite is a *Varroa destructor* mite.

The present disclosure further provides a method for reducing the susceptibility of a bee to a disease caused by a bee virus, the method comprising providing to a parasite of the bee a composition comprising an effective amount of a trigger polynucleotide comprising a nucleic acid sequence that is essentially identical or essentially complementary to a sequence of at least 21 contiguous nucleotides of a bee viral gene, thereby suppressing viral replication in the parasite and reducing the susceptibility of the bee to a disease caused by the bee virus. In some embodiments, the disease is Colony Collapse Disorder (CCD). In some embodiments, the parasite is a *Varroa destructor* mite.

In some embodiments, the composition comprising an effective amount of the trigger polynucleotide is provided by spraying the *Varroa* mite, by directly feeding the *Varroa* mite, by directly feeding the bees in a bee colony, or any combination thereof.

In some embodiments, a method for reducing viral load in *Varroa* mites is provided. In some embodiments the bee virus is selected from the group consisting of: Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), and Kakugo Virus (KV). According to some embodiments, a trigger polynucleotide comprising a nucleic acid sequence having essential identity or essential complementary to a sequence of at least 21 contiguous nucleotides of a bee viral gene is provided. According to some embodiments, there is provided a method for down-regulating expression of a viral gene in *Varroa* mites.

According to some embodiments, methods and compositions for preventing the spread of bee diseases, such as Colony Collapse Disorder through the application of RNA interference technology to *Varroa* mites directed to bee infectious organisms and agents, such as DWV, IAPV, Acute Bee Paralysis Virus and Kashmir Bee Paralysis Virus are provided.

According to some embodiments of the present invention there is provided a method for increasing the tolerance of a bee to a disease caused by a bee virus comprising providing an effective amount of a trigger polynucleotide comprising a nucleic acid sequence that is essentially identical or essentially complementary to a bee viral gene to a *Varroa* mite, thereby reducing the viral load in the *Varroa* mite and increasing the tolerance of the bee to the disease caused by the bee virus. In some embodiments, the nucleic acid is essentially identical or essentially complementary to a sequence of at least 21 contiguous nucleotides of the bee viral gene.

According to some embodiments of the present invention there is provided a method for increasing the tolerance of a bee colony to a disease caused by a bee virus comprising providing an effective amount of a trigger polynucleotide comprising a nucleic acid sequence that is essentially identical or essentially complementary to a bee viral gene to a *Varroa* mite, thereby reducing the viral load in the *Varroa* mite and increasing the tolerance of the bee colony to the disease caused by the bee virus. In some embodiments, the nucleic acid is essentially identical or essentially complementary to a sequence of at least 21 contiguous nucleotides of the bee viral gene.

In one aspect, the present disclosure provides a method for reducing viral load in a *Varroa destructor* mite, the method comprising providing or administering to the *Varroa destructor* mite a composition comprising an effective amount of a trigger polynucleotide comprising a nucleic acid sequence that is essentially identical or essentially complementary to a bee viral sequence, thereby suppressing viral replication in the *Varroa destructor* mite. In some embodiments, the bee viral sequence is a sequence of at least 21 contiguous nucleotides of a bee viral gene.

In one aspect, the present disclosure provides method of reducing viral load in a bee colony, the method comprising reducing viral load in a parasite of the bee colony by providing to the parasite a composition comprising an effective amount of a trigger polynucleotide comprising a nucleic acid sequence that is essentially identical or essentially complementary to a viral sequence, thereby suppressing viral replication in the parasite and reducing the viral load in the bee colony. In some embodiments, the parasite is *Varroa destructor*. In some embodiments, the bee viral sequence is a sequence of at least 21 contiguous nucleotides of a bee viral gene.

In one aspect, the present disclosure provides a method for reducing viral replication in a *Varroa destructor* mite, the method comprising administering to the *Varroa destructor* mite a composition comprising an effective amount of at least one trigger polynucleotide which comprises a nucleic acid sequence that downregulates expression of a bee viral gene in the *Varroa destructor* mite, thereby reducing viral replication in the *Varroa destructor* mite. In some embodiments, the nucleic acid sequence is a trigger polynucleotide that is essentially identical or essentially complementary to the viral gene or a fragment thereof. In some embodiments, the nucleic acid is essentially identical or essentially complementary to a sequence of at least 21 contiguous nucleotides of the bee viral gene.

In one aspect, the present disclosure provides for reducing viral replication in a bee colony, the method comprising reducing viral replication in a parasite of the bee colony by providing to the parasite a composition comprising an effective amount of a trigger polynucleotide comprising a nucleic acid sequence that is essentially identical or essentially complementary to a bee viral sequence, thereby suppressing viral replication in the parasite and reducing viral expression in the bee colony. In some embodiments, the parasite is *Varroa destructor*. In some embodiments, the bee viral sequence is a sequence of at least 21 contiguous nucleotides of a bee viral gene.

In one aspect, the present disclosure provides a method for reducing the susceptibility of a bee to a disease caused by a bee virus, the method comprising providing to a parasite of the bee a composition comprising an effective amount of a trigger polynucleotide comprising a nucleic acid sequence that is essentially identical or essentially complementary to a bee viral sequence, thereby suppressing viral replication in the parasite and reducing the susceptibility of the bee to a disease caused by the bee virus. In some embodiments, the parasite is *Varroa destructor*. In some embodiments, the disease is Colony Collapse Disorder (CCD). In some embodiments, the bee viral sequence is a sequence of at least 21 contiguous nucleotides of a bee viral gene.

According to some embodiments of the invention the bee is a honeybee.

According to some embodiments of the invention the honeybee is a forager.

According to some embodiments of the invention the honeybee is a hive bee.

Several embodiments relate to a composition comprising an effective amount of one or more trigger polynucleotides comprising a nucleic acid sequence that is essentially identical or essentially complementary to a sequence of at least 21 contiguous nucleotides of a bee viral gene. In some embodiments, the virus is selected from the group consisting of: Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), Kakugo Virus (KV), and Lake Sinai Virus (LSV). In some embodiments, the virus is IAPV. In some embodiments, the virus is DWV. In some embodiments, the viral gene encodes a coat protein, RdRp, VP1, VP2, or helicase. In some embodiments, the trigger polynucleotide comprises a nucleic acid sequence having at least about 80%, 85%, 88%, 90%, 92%, 95%, 96%, 97%, 98%, or 99% sequence identity or complementarity, or having 100% sequence identity or complementarity to a sequence selected from the group consisting of SEQ ID NOs:1-21, or a fragment thereof. In some embodiments, the trigger polynucleotide comprises a mixture of 2, 3, 4, 5, 6, 7, 8, 9, or 10 different trigger polynucleotides, which target different viruses, or target different genes of the same virus, or target different fragments of a viral gene. In some embodiments, the composition comprises one or more trigger polynucleotides comprising a nucleic acid sequence having at least about 80%, 85%, 88%, 90%, 92%, 95%, 96%, 97%, 98%, or 99% sequence identity or complementarity, or having 100% sequence identity or complementarity to a DWV sequence and one or more trigger polynucleotides comprising a nucleic acid sequence having at least about 80%, 85%, 88%, 90%, 92%, 95%, 96%, 97%, 98%, or 99% sequence identity or complementarity, or having 100% sequence identity or complementarity to a IAPV sequence. Several embodiments relate to a composition comprising an effective amount of one or more trigger polynucleotides comprising a nucleic acid having at least about 80%, 85%, 88%, 90%, 92%, 95%, 96%, 97%, 98%, or 99% sequence identity or complementarity, or having 100% sequence identity or complementarity to a nucleic acid sequence selected from the group consisting of SEQ ID NOs:11, 13, 14, 17, and 18. Several embodiments relate to a composition comprising an effective amount of one or more trigger polynucleotides comprising a nucleic acid having at least about 80%, 85%, 88%, 90%, 92%, 95%, 96%, 97%, 98%, or 99% sequence identity or complementarity, or having 100% sequence identity or complementarity to a nucleic acid sequence selected from the group consisting of SEQ ID NOs:12, 15, 16, 19, and 20. In some embodiments, the trigger polynucleotide is single-stranded DNA (ssDNA), single-stranded RNA (ssRNA), double-stranded RNA (dsRNA), double-stranded DNA (dsDNA), or double stranded DNA-RNA hybrid. In some embodiments, the composition comprises one or more trigger polynucleotides and one or more excipients. In some embodiments, the excipient comprises one or more substance selected from: a sugar, a solvent, a protein, a bee food, and any combination thereof. In some embodiments, the sugar is selected from: fructose, glucose, sucrose, trehalose, lactose, galactose, ribose and any combination thereof. In some embodiments, the bee food is selected from: honey, pollen, Wheast, soybean flour, yeast, yeast product, and any combination thereof. In some embodiments, the composition is a bee-ingestible composition selected from the group consisting of a liquid bee-ingestible composition and a solid bee-ingestible composition. In some embodiments, the liquid bee-ingestible composition is a sugar syrup. In some embodiments, the solid bee-ingestible composition is a cake or dry mix.

BRIEF DESCRIPTION OF THE DRAWINGS

FIG. 5B depicts a graph showing IAPV levels in *Varroa* 72 h following treatment in a *Varroa* direct feeding experiment, measured by QuantiGene®.

DETAILED DESCRIPTION

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

As used herein, the term "about" refers to ±10%.

As used herein, the singular form "a", "an" and "the" include plural references unless the context clearly dictates otherwise. For example, the term "a compound" or "at least one compound" may include a plurality of compounds, including mixtures thereof.

Unless otherwise stated, nucleic acid sequences in the text of this specification are given, when read from left to right, in the 5' to 3' direction. It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. Further, disclosure of a nucleic acid sequence discloses the sequence of its reverse complement, as one necessarily defines the other, as is known by one of ordinary skill in the art. Where a term is provided in the singular, the inventors also contemplate aspects of the invention described by the plural of that term.

Figure 1:
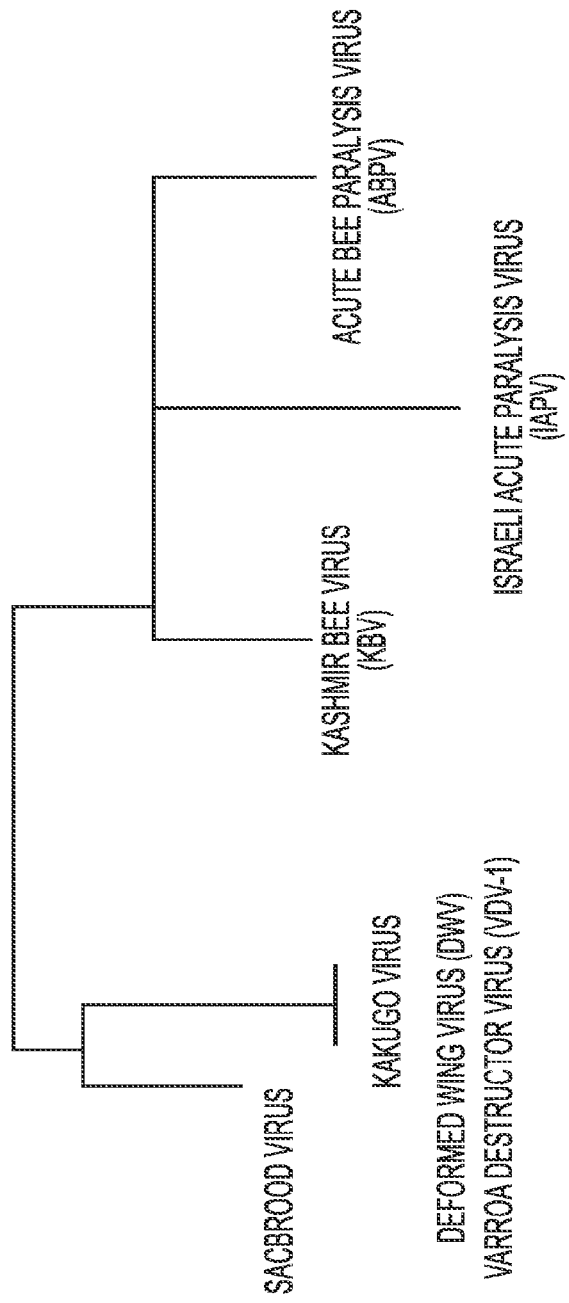
FIG. 1 depicts a phylogenetic tree of some bee viruses.
Figure 2A:
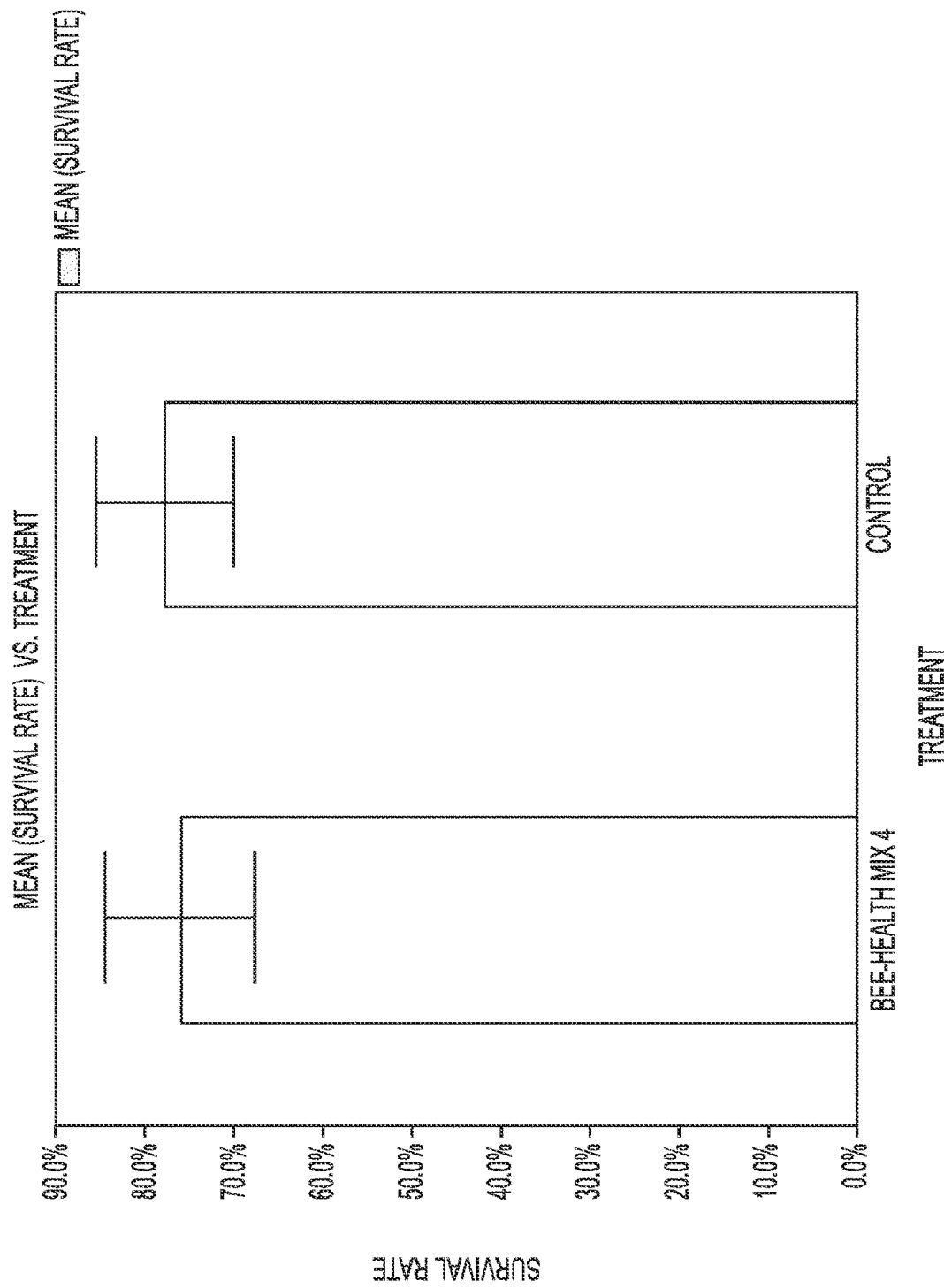
FIG. 2A depicts a graph showing the survival rate of *Varroa* mites after treatment with bee viruses trigger mix.
Figure 2B:
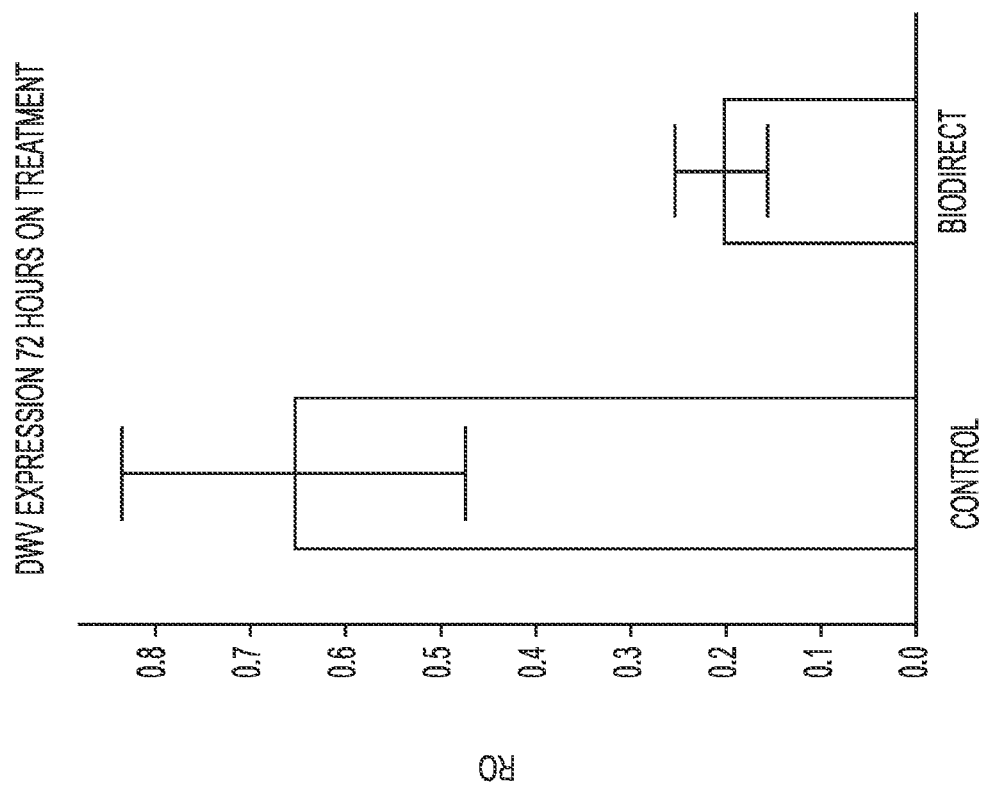
FIG. 2B depicts a graph showing DWV levels in *Varroa* 72 h following treatment in a *Varroa* direct feeding experiment, measured by Q-PCR.
Figure 3:
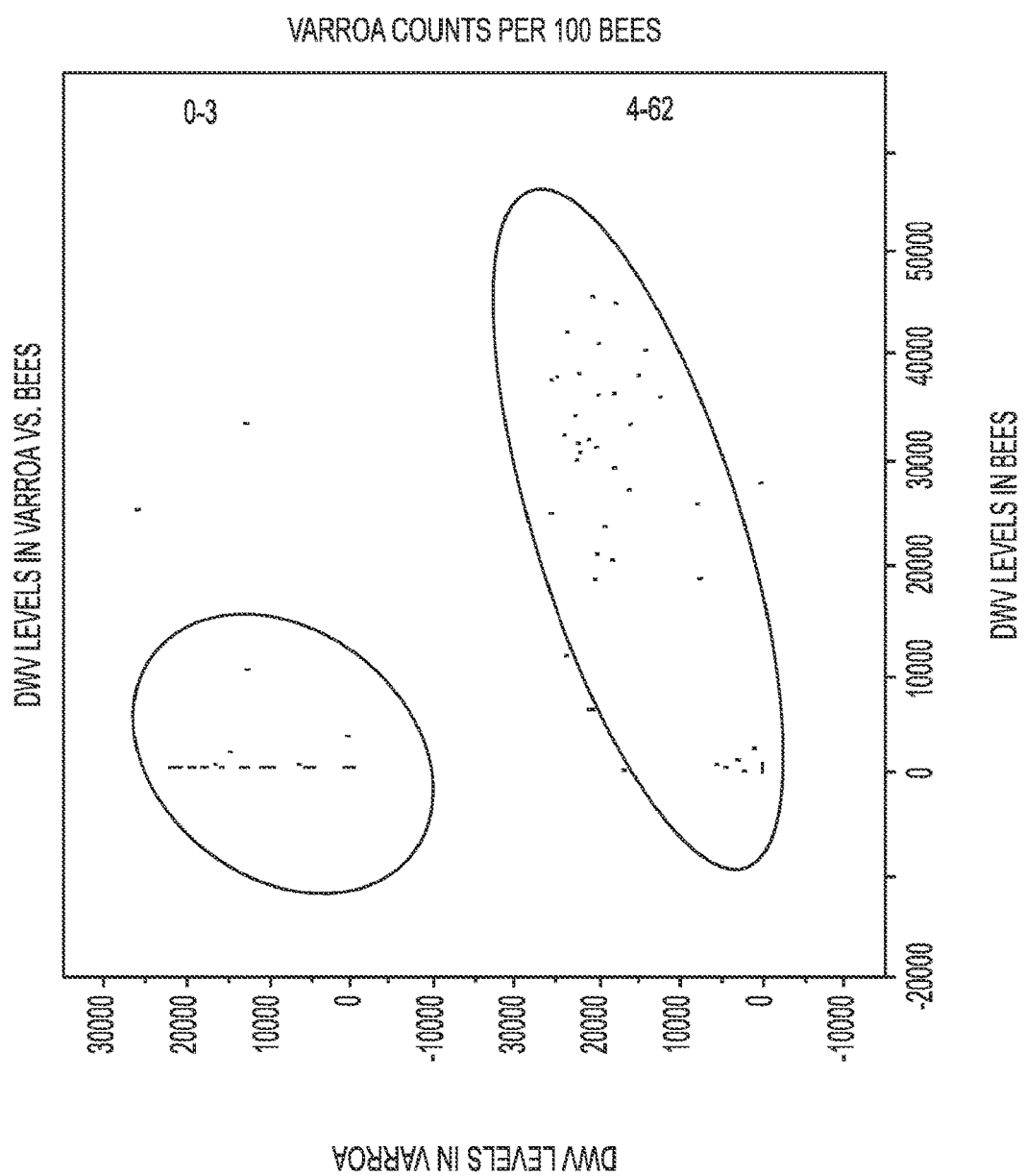
FIG. 3 depicts a graph showing DWV levels in bees versus DWV levels in *Varroa*, at different (0-3 or 4-62) *Varroa* counts per 100 bees.

Bees are susceptible to a myriad of viral infections. To date, 24 bee viruses have been identified. Most are positive strand RNA viruses, which contain RNA-dependant RNA polymerase (RdRp). Two phylogenetic families of bee viruses with two main structural formats have been identified. See FIG. 1. Field samples of bees in the U.S. screened for 9 different bee viruses using QuantiGene® analysis showed a high prevalence of Deformed Wing Virus (DWV), *Varroa Destructor* Virus (VDV-1), Israeli Acute Paralysis Virus (IAPV), Acute Bee Paralysis Virus (ABPV) and Kashmir Bee Virus (KBV). Lake Sinai Virus (LSV), including Lake Sinai Virus-1 (LSV-1) and Lake Sinai Virus-2 (LSV-2) is another virus found in bee hives. Treatment of viral infections by down-regulation of a particular viral gene product has shown to be successful in eliminating virally induced infections in the bee (see U.S. Patent Publication 2009/0118214). The present inventors now disclose methods and compositions for the treatment of viral infection in *Varroa* mites and in bees. The present inventors further disclose treatment of viral infection in bees by reducing the viral load of parasitic *Varroa* mites.

According to some embodiments, RNA interference technology is used to reduce the viral load in *Varroa destructor* mites and in bees. *Varroa* mites parasitize pupae and adult bees and reproduce in the pupal brood cells. The mites use their mouths to puncture the exoskeleton and feed on the bee's hemolymph. Polynucleotide agents administered to the bees to treat *Varroa* mite infestations presented in the bee's hemolymph thereby becoming available to the mite (see U.S. Patent Publication 2012/0258646).

In several embodiments of the present disclosure, RNA interference technology is used to reduce viral replication in *Varroa destructor* mites and in bees. In several embodiments of the present disclosure, RNA interference technology is used to reduce or prevent transmission of bee viruses from a bee or bee larvae to a *Varroa destructor* mite which feeds on the bee or bee larvae. In several embodiments of the present disclosure, RNA interference technology is used to reduce or prevent transmission of bee viruses from a *Varroa destructor* mite to a bee or bee larvae that the mite parasitizes.

In some embodiments of the present disclosure, RNA interference technology is used to reduce viral load in a bee.

In some embodiments, RNA interference technology is used to reduce viral load in a bee colony.

In some embodiments of the present disclosure, RNA interference technology is used to reduce viral replication in a bee. In some embodiments, RNA interference technology is used to reduce viral replication in a bee colony.

RNA interference refers to the process of sequence-specific post-transcriptional gene silencing in animals mediated by small RNAs. The corresponding process in plants is commonly referred to as post-transcriptional gene silencing or RNA silencing and is also referred to as quelling in fungi. While not being limited to any particular theory, the process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. In aspects according to the present disclosure, a nucleic acid composition results in RNA interference in a target organism. In certain aspects the nucleic acid composition results in RNA interference in *Varroa destructor* when present on the host organism, the bee or bee larvae.

The phrase "*Varroa destructor* mite" refers to the external parasitic mite that attacks honey bees *Apis cerana* and *Apis mellifera*. The mite can be at an adult stage, feeding off the bee, or at a larval stage, inside the honey bee brood cell.

In some embodiments of the present disclosure, a bee virus is selected from the group consisting of: Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), Kakugo Virus (KV), and Lake Sinai Virus (LSV).

In some embodiments of the present disclosure, the bee virus is a positive strand RNA virus. In some embodiments, the bee virus is a negative strand RNA virus. In some embodiments, the bee virus is DWV. In some embodiments, the bee virus is IAPV. In some embodiments, the bee virus is LSV.

As used herein, a measurement of "viral load," "viral levels," and "viral expression" refers to the detection of the sense strand of a bee virus sequence, and they are used interchangeably in the present disclosure. A number of detection methods are known in the art, including but not limited to, quantitative PCR (Q-PCR) and the QuantiGene® assay. In some embodiments, viral load or viral expression is measured as median fluorescence intensity (MFI) and normalized with MFI of housekeeping genes to represent the presence of the virus in a bee, a bee colony, or *Varroa* mites. In some embodiments, viral load is a measure of the severity of an active viral infection.

As used herein, a measurement of "viral replication" refers to the detection of the negative strand of a bee virus sequence. In some embodiments, viral replication is measured as median fluorescence intensity (MFI) and normalized with MFI of housekeeping genes to represent the replication of the virus in a bee, a bee colony, or *Varroa* mites. In some embodiments, viral replication is a measure of the severity of an active viral infection.

As used herein, the term "viral titer" refers to the concentration of viruses in a sample. In some embodiments, the viral load is measured by the viral titer. A number of methods are known in the art for calculating the viral titer, and they are emcompassed by this application.

As used herein, the term "host" or "host organism" refers to an organism that harbors a parasite and provides nourishment to the parasite. A "parasite" is an organism that has a non-mutual symbiotic relationship with a host organism and benefits at the expense of the host organism. In some embodiments, the host organism is a bee. In some embodiments, the parasite is a *Varroa* mite.

As used herein, the term "bee" refers to both an adult bee and pupal cells thereof. According to one aspect, the bee is in a hive. An adult bee is defined as any of several winged, hairy-bodied, usually stinging insects of the superfamily Apoidea in the order Hymenoptera, including both solitary and social species and characterized by sucking and chewing mouthparts for gathering nectar and pollen. Examples of bee species include, but are not limited to, *Apis, Bombus, Trigona, Osmia* and the like. In one aspect, bees include, but are not limited to bumblebees (*Bombus terrestris*), honeybees (*Apis mellifera*) (including foragers and hive bees) and *Apis cerana*. The present disclosure provides for, and includes, methods and compositions for treating insects as either a host or as a parasite.

According to one aspect, a bee is part of a colony. The term "colony" refers to a population of bees comprising dozens to typically several tens of thousands of bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage. The present disclosure provides for, and includes, methods and compositions for treating insects colonies.

As used herein, the term "parasite" refers to both adult and immature forms of organisms that directly benefit at the expense of another, host, organism, for example by feeding on the blood or fluids of the host, living intracellularly in a host organism cell, or living within a body of a host organism. The present disclosure provides for, and includes, methods and compositions for treating parasites. In an aspect, the parasite is *Varroa destructor*.

As used herein, the phrase "RNA silencing" refers to a group of regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding viral gene. RNA silencing has been observed in many types of organisms, including plants, animals, and fungi. In aspects according the present disclosure, nucleic acid compositions provide for RNA silencing. In certain aspects, the nucleic acid compositions provide for silencing of viral genes in a bee parasite.

The present disclosure provides a method for reducing viral load or suppressing viral replication in a *Varroa destructor* mite or in a bee colony, the method comprising providing to the *Varroa destructor* mite or the bee colony a composition comprising an effective amount of at least one trigger polynucleotide comprising a nucleic acid sequence that is essentially identical or essentially complementary to a sequence of at least 21 contiguous nucleotides of a bee viral gene, thereby reducing viral load or suppressing viral replication in the *Varroa destructor* mite or in the bee colony. In some embodiments, the virus is selected from the group consisting of: Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), Kakugo Virus (KV), and Laker Sinai Virus (LSV).

The present disclosure also provides a composition for providing to a *Varroa destructor* mite, a bee, or a bee colony, comprising an effective amount of a trigger polynucleotide comprising a nucleic acid sequence that is essentially identical or essentially complementary to a sequence of at least 21 contiguous nucleotides of a bee viral gene. In some embodiments, the composition reduces viral load or suppresses viral replication in the *Varroa destructor* mite, the bee, or the bee colony. In some embodiments, the composition increases the tolerance of a bee or a bee colony to a disease caused by the bee virus.

In some embodiments, the trigger polynucleotide is single-stranded DNA (ssDNA), single-stranded RNA (ssRNA), double-stranded RNA (dsRNA), double-stranded DNA (dsDNA), or double stranded DNA-RNA hybrid.

In some embodiments, the trigger polynucleotide downregulates the viral gene. In some embodiments, the viral gene encodes a coat protein, RdRp, VP1, VP2, or helicase. In some embodiments, the trigger polynucleotide comprises a nucleic acid sequence having at least about 80%, 85%, 88%, 90%, 92%, 95%, 96%, 97%, 98%, or 99% sequence identity or complementarity, or having 100% sequence identity or complementarity to a sequence selected from the group consisting of SEQ ID NOs:1-21, or a fragment thereof. In some embodiments, the trigger polynucleotide comprises a mixture of 2, 3, 4, 5, 6, 7, 8, 9, or 10 different trigger polynucleotides, which target different viruses, or target different genes of the same virus, or target different fragments of a viral gene.

The present disclosure also provides a method for reducing viral load in a bee colony, the method comprising reducing viral load in a parasite of the bee colony by providing to the parasite a composition comprising an effective amount of a trigger polynucleotide comprising a nucleic acid sequence that is essentially identical or essentially complementary to a sequence of at least 21 contiguous nucleotides of a bee viral gene, thereby suppressing viral replication in the parasite and reducing the viral load in the bee colony. In some embodiments, the parasite is a *Varroa destructor* mite.

The present disclosure further provides a method for reducing the susceptibility of a bee to a disease caused by a bee virus, the method comprising providing to a parasite of the bee a composition comprising an effective amount of a trigger polynucleotide comprising a nucleic acid sequence that is essentially identical or essentially complementary to a sequence of at least 21 contiguous nucleotides of a bee viral gene, thereby suppressing viral replication in the parasite and reducing the susceptibility of the bee to a disease caused by the bee virus. In some embodiments, the disease is Colony Collapse Disorder (CCD). In some embodiments, the parasite is a *Varroa destructor* mite.

In some embodiments, the composition comprising an effective amount of the trigger polynucleotide is provided by spraying the *Varroa* mite, by directly feeding the *Varroa* mite, by directly feeding the bees in a bee colony, or any combination thereof.

In one aspect, the present disclosure provides a method for reducing viral load or suppressing viral replication in a *Varroa destructor* mite, the method comprising providing to the *Varroa destructor* mite a composition comprising an effective amount of a trigger polynucleotide comprising a nucleic acid sequence that is essentially identical or essentially complementary to a viral sequence, thereby suppressing viral replication or reducing viral load in the *Varroa destructor* mite.

In one aspect, the present disclosure provides a method for reducing viral load or suppressing viral replication in a bee or a bee colony, the method comprising providing to the bee or bee colony a composition comprising an effective amount of a trigger polynucleotide comprising a nucleic acid sequence that is essentially identical or essentially complementary to a viral sequence, thereby suppressing viral replication or reducing viral load in the bee or bee colony.

In one aspect, the present disclosure provides a method of reducing viral load or suppressing viral replication in a bee or a bee colony, the method comprising reducing viral load or suppressing viral replication in a parasite of the bee or bee colony by providing to the parasite a composition comprising an effective amount of a trigger polynucleotide comprising a nucleic acid sequence that is essentially identical or essentially complementary to a viral sequence, thereby suppressing viral replication in the parasite and reducing the viral load in the bee colony. In some embodiments, the parasite is *Varroa destructor*.

In one aspect, the present disclosure provides a method for reducing viral load or suppressing viral replication in a *Varroa destructor* mite, the method comprising administering to the *Varroa destructor* mite a composition comprising an effective amount of at least one trigger polynucleotide which comprises a nucleic acid sequence that downregulates expression of a viral gene in the *Varroa destructor* mite, thereby reducing viral load or suppressing viral replication in the *Varroa destructor* mite. In some embodiments, the nucleic acid sequence is a trigger polynucleotide that is essentially identical or essentially complementary to the viral gene or a fragment thereof.

In one aspect, the present disclosure provides for reducing viral load or suppressing viral replication in a bee colony, the method comprising reducing viral load or suppressing viral replication in a parasite of the bee colony by providing to the parasite a composition comprising an effective amount of a trigger polynucleotide comprising a nucleic acid sequence that is essentially identical or essentially complementary to a viral sequence, thereby suppressing viral replication in the parasite and reducing viral expression in the bee colony. In some embodiments, the parasite is *Varroa destructor*.

In one aspect, the present disclosure provides a method for reducing the susceptibility of a bee to a disease caused by a bee virus, the method comprising providing to a parasite of the bee a composition comprising an effective amount of a trigger polynucleotide comprising a nucleic acid sequence that is essentially identical or essentially complementary to a viral sequence, thereby suppressing viral replication in the parasite and reducing the susceptibility of the bee to a disease caused by the bee virus. In some embodiments, the parasite is *Varroa destructor*. In some embodiments, the disease is Colony Collapse Disorder (CCD).

As used herein, the term "trigger" or "trigger polynucleotide" refers to a bioactive polynucleotide molecule that is substantially homologous or complementary to a polynucleotide sequence of a target gene or an RNA expressed from the target gene or a fragment thereof and functions to suppress the expression of the target gene or produce a knock-down phenotype. Trigger polynucleotides are capable of inhibiting or "silencing" the expression of a target gene. Trigger polynucleotides are generally described in relation to their "target sequence." Trigger polynucleotides may be single-stranded DNA (ssDNA), single-stranded RNA (ssRNA), double-stranded RNA (dsRNA), double-stranded DNA (dsDNA), or double-stranded DNA/RNA hybrids. Trigger polynucleotides may comprise naturally-occurring nucleotides, modified nucleotides, nucleotide analogues or any combination thereof. In some embodiments, a trigger polynucleotide may be incorporated within a larger polynucleotide, for example in a pri-miRNA molecule. In some embodiments, a trigger polynucleotide may be processed into a small interfering RNA (siRNA). In an aspect, the trigger polynucleotide is capable of inhibiting the expression of a viral gene. In another aspect, the trigger polynucleotide is capable of being used in methods to inhibit the expression of a viral gene and thereby reduce the viral load of a host organism. In certain aspects, the viral gene is a DWV, VDV-1, IAPV, ABPV, KBV, or LSV gene and the host organism is *Varroa destructor*.

As used herein, the term "target sequence" or "target gene" refers to a nucleotide sequence that occurs in a gene or gene product against which a trigger polynucleotide is directed. In this context, the term "gene" means a locatable region of genomic sequence, corresponding to a unit of inheritance, which includes regulatory regions, such as promoters, enhancers, 5' untranslated regions, intron regions, 3' untranslated regions, transcribed regions, and other functional sequence regions that may exist as native genes or transgenes in a plant genome.

Depending upon the circumstances, the term target sequence or target gene can refer to the full-length nucleotide sequence of the gene or gene product targeted for suppression or the nucleotide sequence of a portion of the gene or gene product targeted for suppression.

As used herein, the term "derived from" refers to a specified nucleotide sequence that may be obtained from a particular specified source or species, albeit not necessarily directly from that specified source or species.

As used herein, the terms "sequence", "nucleotide sequence" or "polynucleotide sequence" refer to the nucleotide sequence of a DNA molecule, an RNA molecule or a portion thereof.

The term "polynucleotide" refers to any polymer of mononucleotides that are linked by internucleotide bonds. Polynucleotides may be composed of naturally-occurring ribonucleotides, naturally-occurring deoxyribonucleotides, analogs of naturally-occurring nucleotides (e.g., enantiomeric forms of naturally-occurring nucleotides), or any combination thereof. Where a polynucleotide is single-stranded, its length can be described in terms of the number of nucleotides. Where a polynucleotide is double-stranded, its length can be described in terms of the number of base pairs.

As used herein, the term "non-transcribable polynucleotide" refers to a polynucleotide that does not comprise a complete polymerase II transcription unit.

The term "gene expression" refers to the process of converting genetic information encoded in genomic DNA into RNA (e.g., mRNA, rRNA, tRNA, or snRNA) through transcription of the gene via the enzymatic action of an RNA polymerase, and into protein, through translation of mRNA. Gene expression can be regulated at many stages in the process.

In the embodiments described herein, viral sequences are selected as targets for trigger polynucleotides. In some embodiments, target sequences are selected for including low G/C content as these have proven to be more effective in mediating gene silencing as compared to those with G/C content higher than 55%. In some embodiments, several target sites are selected along the length of the target gene.

In some embodiments, the trigger polynucleotide comprises a nucleotide sequence that is essentially complementary or essentially identical to a viral gene or a fragment thereof. In some embodiments, the trigger polynucleotide comprises a nucleic acid that is essentially complementary or essentially identical to a sequence of at least 21 contiguous nucleotides of a bee viral gene. In some embodiments, the trigger polynucleotide comprises a nucleic acid that is essentially complementary or essentially identical to a sequence of at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 contiguous nucleotides of a bee viral gene. In some embodiments, the viral gene encodes a coat protein, RdRp, Viral Protein 1 (VP1), VP2, or Helicase. In some embodiments, the trigger polynucleotide comprises a nucleotide sequence that is essentially complementary or essentially identical to a DWV or a IAPV gene, or a fragment thereof. In some embodiments, the trigger polynucleotide comprises a nucleotide sequence that is essentially complementary or essentially identical to a LSV gene or a fragment thereof. In some embodiments, the trigger polynucleotide comprises a nucleotide sequence that is essentially complementary or essentially identical to an Acute Bee Paralysis gene or a fragment thereof. In some embodiments, the trigger polynucleotide comprises a nucleotide sequence that is essentially complementary or essentially identical to a Kashmir Bee Virus gene or a fragment thereof. In some embodiments, the trigger polynucleotide comprises a nucleotide sequence that is essentially complementary or essentially identical to a Black Queen Cell Virus gene or a fragment thereof. In some embodiments, the trigger polynucleotide comprises a nucleotide sequence that is essentially complementary or essentially identical to a Chronic Paralysis Virus gene or a fragment thereof. In some embodiments, the trigger polynucleotide comprises a nucleotide sequence that is essentially complementary or essentially identical to a Cloudy Wing Virus gene or a fragment thereof.

Multiple bee-pathogen sequences can be designed to include sequences suitable for producing trigger polynucleotides effective against more than one bee virus. Such multiple bee-pathogen dsRNA can be of the long or short variety, and may include sequences corresponding to homologous sequences within a class of bee viruses. Further, multiple sequences can be designed to include two or more dsRNA sequences of the same bee-pathogen.

By "essentially identical" or "essentially complementary," it is meant that the bioactive polynucleotide trigger (or at least one strand of a double-stranded polynucleotide or portion thereof, or a portion of a single strand polynucleotide) hybridizes under physiological conditions to the endogenous gene, an RNA transcribed there from, or a fragment thereof, to effect regulation or suppression of the endogenous gene. For example, in some embodiments, a bioactive polynucleotide trigger has 100 percent sequence identity or at least about 80, 81, 82, 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive polynucleotide trigger has 100 percent sequence complementarity or at least about 80, 81, 82, 83, 84, 85, 86, 87, 88, 89, 90, 91, 92, 93, 94, 95, 96, 97, 98, or 99 percent sequence complementarity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive polynucleotide trigger has 100 percent sequence identity with or complementarity to one allele or one family member of a given target gene (coding or non-coding sequence of a gene). In some embodiments, a bioactive polynucleotide trigger has at least about 80, 81, 82, 83, 84, 85, 86, 87, 88, 89, 90, 91, 92, 93, 94, 95, 96, 97, 98, or 99 percent sequence identity with or complementarity to multiple alleles or family members of a given target gene. In some embodiments, a bioactive polynucleotide trigger has 100 percent sequence identity with or complementarity to multiple alleles or family members of a given target gene.

As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is completely complementary to a reference nucleotide sequence will exhibit a sequence identical to the reverse complement sequence of the reference nucleotide sequence.

It will be appreciated that a trigger polynucleotide, for example dsRNA, of the present disclosure need not be limited to those molecules containing only natural nucleotides, but further encompasses chemically-modified nucleotides and non-nucleotides. Trigger polynucleotide agents of the present disclosure may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 613, and those disclosed by Sanghvi, Y. S., Chapter 15, Antisense Research and Applications, pages 289-2, Crooke, S. T. and Lebleu, B., ed., CRC Press, 1993. Such bases are particularly useful for increasing the binding affinity of the oligomeric compounds of the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi Y S et al. (1993) Antisense Research and Applications, CRC Press, Boca Raton 276-278) and are presently preferred base substitutions, even more particularly when combined with 2'-O-methoxyethyl sugar modifications.

Following synthesis, the trigger polynucleotides of the present disclosure may optionally be purified. For example, polynucleotides can be purified from a mixture by extraction with a solvent or resin, precipitation, electrophoresis, chromatography, or a combination thereof. Alternatively, trigger polynucleotides may be used with no, or a minimum of, purification to avoid losses due to sample processing. The trigger polynucleotides may be dried for storage or dissolved in an aqueous solution. The solution may contain buffers or salts to promote annealing, and/or stabilization of the duplex strands.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein, a "control organism" means an organism that does not contain the trigger polynucleotide, or other nucleic acid that provides for control of a viral infection or viral replication. Control organisms are generally from same species and of the same developmental stage which is grown under the same growth conditions as the treated organism. Similarly, a "control colony" means a colony of organisms that do not contain the trigger polynucleotide or other nucleic acid that provides for control of viral infection or viral replication. Control colonies of organisms are generally from same species and of the same developmental stage which are grown under the same growth conditions as the treated colony of organisms.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. In an aspect according to the present disclosure, a composition may be used to treat an organism or colony of organisms for viral infection. In an aspect, a dsRNA composition may be used to treat a host organism or a parasite for viral infection. In an aspect, the host organism is a bee and the parasite is the mite, *Varroa destructor*. In an aspect, the present disclosure provides a method for treating Colony Collapse Disorder (CCD).

As used herein, the terms "improving," "improved," "increasing," and "increased" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase in an organism or colony population, in increased productivity of an organism or colony (e.g., increased honey productions), increase growth rate of an organism or colony, or increased reproductive rate as compared to a control organism or colony. The present disclosure provides for methods of improving the health of an organism or colony by providing an antiviral composition.

As used herein, "viral load", also known as "viral burden," "viral titer", "viral level" or "viral expression" in some embodiments, is a measure of the severity of a viral infection, and can be calculated by estimating the amount of virus in an infected organism, an involved body fluid, or an affected colony. It can also be calculated by estimating or measuring the amount of the sense strand of a bee virus sequence in an infected organism, an involved body fluid, or an affected colony.

As used herein, "a reduction" of the level of an agent such as a protein or mRNA means that the level is reduced relative to an organism or colony lacking a trigger polynucleotide, for example a dsRNA molecule, capable of reducing the agent. Also as used herein, "a reduction" in reference to viral load, means that the viral load is reduced relative to an organism or colony lacking a nucleic acid or other dsRNA molecule capable of reducing the viral load. The present disclosure provides for, and includes, methods and compositions for reducing the level of a viral protein or viral gene expression and reducing the viral load. The present disclosure also provides for methods and compositions for reducing the level of a viral replication in a *Varroa* mite or in a bee.

As used herein, the term "at least a partial reduction" of the level of an agent such as a protein or mRNA means that the level is reduced at least 25% relative to an organism or colony lacking a trigger polynucleotide, for example a dsRNA molecule, capable of reducing the agent. Also as used herein, "at least a partial reduction" in reference to viral load, means that the level is reduced at least 25% relative to an organism or colony lacking a nucleic acid or other dsRNA molecule capable of reducing the viral load. The present disclosure provides for, and includes, methods and compositions for at least partially reducing the level of a viral protein or viral gene expression and at least partially reducing the viral load.

As used herein, "a substantial reduction" of the level of an agent such as a protein or mRNA means that the level is reduced relative to an organism or colony lacking a trigger polynucleotide, for example a dsRNA molecule, capable of reducing the agent, where the reduction of the level of the agent is at least 75%. Also as used herein, "a substantial reduction" in reference to viral load, means that the viral load is reduced at least 75% relative to an organism or colony lacking a nucleic acid or other dsRNA molecule capable of reducing the viral load. The present disclosure provides for, and includes, methods and compositions for substantially reducing the level of a viral protein or viral gene expression and substantially reducing the viral load.

As used herein, "an effective elimination" of an agent such as a protein or mRNA is relative to an organism or colony lacking trigger polynucleotide, for example a dsRNA molecule, capable of reducing the agent, where the reduction of the level of the agent is greater than 95%. A trigger polynucleotide, preferably a dsRNA molecule, is preferably capable of providing at least a partial reduction, more preferably a substantial reduction, or most preferably effective elimination of another agent such as a viral protein or viral gene expression, or a virus, wherein the agent leaves the level of expression of a host gene, essentially unaffected, substantially unaffected, or partially unaffected. Also as used herein, "an effective elimination" in reference to viral load, means that the viral load is reduced at least 95% relative to an organism or colony lacking a nucleic acid or other dsRNA molecule capable of reducing the viral protein, viral gene expression or viral load. The present disclosure provides for, and includes, methods and compositions for the effective elimination of a viral protein or viral gene expression and effectively eliminating viral infection.

As used herein, the terms "suppress," "repress," and "downregulate" when referring to the expression or activity of a nucleic acid molecule in an organism are used equivalently herein and mean that the level of expression or activity of the nucleic acid molecule in a cell of an organism or a colony after applying a method of the present disclosure is lower than its expression or activity in the cell of an organism or a colony before applying the method, or compared to a control organism or colony lacking a nucleic acid molecule of the disclosure. The present disclosure provides for, and includes, methods and compositions for suppressing, repressing and down-regulating the level of a viral protein or viral gene expression and suppressing, repressing and down-regulating the level viral infection in an organism or colony. The present disclosure also provides for methods and compositions for suppressing, repressing and down-regulating the level of a viral replication in an organism or colony. In some embodiments, the organism is a *Varroa* mite. In some embodiments, the organism is a bee. In some embodiments, the colony is a bee colony.

The terms "suppressed," "repressed" and "downregulated" as used herein are synonymous and mean herein lower, preferably significantly lower, expression or activity of the targeted nucleic acid molecule. Also as used herein, "suppressed," "repressed" and "downregulated" in reference to viral infection or viral load, means that the level of infection or viral load is lower, preferably significantly lower relative to an organism or colony lacking a nucleic acid or other dsRNA molecule capable of reducing viral gene expression. The present disclosure provides for, and includes, methods and compositions for suppressing, repressing and down-regulating the expression or activity of a viral protein or viral gene and suppressing, repressing and down-regulating the infectivity of viruses.

In some embodiments, the trigger polynucleotide is single-stranded DNA (ssDNA), single-stranded RNA (ssRNA), double-stranded RNA (dsRNA), double-stranded DNA (dsDNA), or double-stranded DNA/RNA hybrid. In some embodiments, the trigger polynucleotide is dsRNA.

In some embodiments, the trigger polynucleotide comprises a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% sequence identity, or having 100% sequence identity to a sequence selected from the group consisting of SEQ ID NOs: 1-21, or a fragment thereof. In some embodiments, the trigger polynucleotide comprises a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% sequence complementarity, or having 100% sequence complementarity to a sequence selected from the group consisting of SEQ ID NOs: 1-21, or a fragment thereof. In some embodiments, the trigger polynucleotide composition comprises a nucleic acid sequence having essential identity or essential complementarity to a sequence consisting of at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 contiguous nucleotides from a sequence selected from SEQ ID NOs: 1-21.

In certain aspects, the present disclosure provides a dsRNA composition comprising a nucleotide sequence having at least about 80%, 81%, 82%, 83%, 84%, 85%, 86%, 87%, 88%, 89%, 90%, 91%, 92%, 93%, 94%, 95%, 96%, 97%, 98%, or 99% sequence identity or complementarity to a sequence selected from the group consisting of SEQ ID NOs: 1 to 21, or a fragment thereof. In certain aspects, the dsRNA composition comprises a nucleotide sequence having 100% identity or complementarity to a sequence selected from SED ID NOs: 1-21, or a fragment thereof. In another aspect, the present disclosure provides a DNA encoding at least one dsRNA precursor comprising a nucleotide sequence having 100% identity or complementarity to a sequence selected from the group consisting of SEQ ID NOs: 1 to 21, or a fragment thereof, or having at least about 80%, 81%, 82%, 83%, 84%, 85%, 86%, 87%, 88%, 89%, 90%, 91%, 92%, 93%, 94%, 95%, 96%, 97%, 98%, or 99% sequence identity or complementarity to a sequence selected from SEQ ID NOs: 1 to 21, or a fragment thereof. In yet another aspect, the present disclosure provides a recombinant DNA encoding at least one dsRNA precursor comprising a nucleotide sequence selected from the group consisting of SEQ ID NOs: 1 to 21, or a fragment thereof, a heterologous promoter and a transcription terminator sequence are provided. In another aspect, the present disclosure provides a recombinant DNA encoding at least one dsRNA precursor comprising a nucleotide sequence having at least about 80%, 81%, 82%, 83%, 84%, 85%, 86%, 87%, 88%, 89%, 90%, 91%, 92%, 93%, 94%, 95%, 96%, 97%, 98%, or 99% sequence identity or complementarity to a sequence selected from the group consisting of SEQ ID NOs: 1 to 21, or a fragment thereof, and further comprising a heterologous promoter and a transcription terminator.

In several embodiments, the present disclosure provides a composition comprising at least one trigger polynucleotide. In some embodiments, the composition comprises a mixture of at least 2, 3, 4, 5, 6, 7, 8, 9, or 10 different trigger polynucleotides. In some embodiments, the composition comprises a mixture of 2, 3, 4, 5, 6, 7, 8, 9, or 10 different trigger polynucleotides. In some embodiments, the trigger polynucleotides can target different viruses. In some embodiments, the trigger polynucleotides can target different genes of the same virus. In some embodiments, the trigger polynucleotides can target different fragments of a viral sequence or a viral gene.

It will be appreciated that the trigger polynucleotides, for example dsRNA, can be delivered to the pest or parasite in a great variety of ways. According to one aspect, the trigger polynucleotides are delivered directly to the parasite (e.g. by spraying a mite infested hive). The trigger polynucleotides, or constructs encoding same may enter the mites' bodies by diffusion. In another aspect, the trigger polynucleotides are indirectly delivered via a host organism (e.g., by providing a bee food comprising the trigger polynucleotide to a bee). In an aspect, the parasite is *Varroa destructor*. In one aspect, the host organism is a bee.

It will be appreciated that since many parasites use their mouths to puncture the host arthropod exoskeleton and feed on the arthropod's hemolymph, the present disclosure contemplates delivering the trigger polynucleotides, for example dsRNA, of the present disclosure to the host arthropod, whereby they become presented in the host arthropod hemolymph thereby becoming available to the parasite. Thus, according to another aspect, the nucleic acid agents are delivered indirectly to the parasite (for example to a mite via a host bee). In certain aspects, the pest or parasite is *Varroa destructor* and the host arthropod is a bee.

According to one aspect, the trigger polynucleotides, for example dsRNA, are delivered to the infested hosts by spraying. The trigger polynucleotides, for example dsRNA, or constructs encoding same may enter the host's bodies by diffusion. In certain aspects, the pest or parasite is *Varroa destructor* and the host arthropod is a bee.

According to another aspect, the trigger polynucleotides, for example dsRNA, are delivered to the host via its food. The present inventors consider that following ingestion of the trigger polynucleotides of the present disclosure, the trigger polynucleotides can be presented, for example, in a host arthropod in the host's hemolymph, whereby it becomes available to the parasite, for example a *Varroa* mite.

In one aspect, the polynucleotides of the present disclosure can be synthesized in vitro and added to the food. For example double stranded RNA can be synthesized by adding two opposing promoters (e.g. T7 promoters) to the ends of the gene segments, wherein the promoter is placed immediately 5' to the gene and the promoter is placed immediately 3' to the gene segment in the opposite orientation. The dsRNA can then be transcribed in vitro with the T7 RNA polymerase.

Non-limiting examples of sequences for synthesizing dsRNA according to aspects of the present disclosure are provided in SEQ ID NOs: 1-21. Full length or a fragment of these sequences can be used as the template.

This application provides and discloses compositions comprising a trigger polynucleotide and an excipient substance. In an aspect, the excipient can be a combination of one or more inactive components. In some aspects, the excipient comprises a sugar. Examples of sugars include hexoses, disaccharides, trisaccharides and higher sugars. Excipient sugars include, for example, fructose, glucose, sucrose, trehalose, lactose, galactose, ribose. In other aspects the excipient comprises a sugar and a solvent. In other aspects, the excipient comprises a protein. In an aspect, the protein is a soy protein. In other aspects the excipient is pollen. In aspects according to the present disclosure, the excipient is a bee food.

In some embodiments, the excipient comprises one or more substance selected from: a sugar, a solvent, a protein, a bee food, and any combination thereof. In some embodiments, the sugar is selected from: fructose, glucose, sucrose, trehalose, lactose, galactose, ribose and any combination thereof. In some embodiments, the bee food is selected from: honey, pollen, Wheast, soybean flour, yeast, yeast product, and any combination thereof.

Bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to percent pollen improves the quality and quantity of essential nutrients that are required by bees for vital activity. Cane or beet sugar, isomerized corn syrup, and type-50 sugar syrup are satisfactory substitutes for honey in the natural diet of honey bees. The last two can be supplied only as a liquid to bees. Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one aspect, pan or trays in which floating supports—such as wood chips, cork, or plastic sponge—are present are envisaged. Detailed descriptions of supplemental feeds for bees can be found in, for example, USDA publication by Standifer, et al. 1977, entitled "Supplemental Feeding of Honey Bee Colonies" (USDA, Agriculture Information Bulletin No. 413).

In some embodiments, bee feeding comprises providing a bee-ingestible composition selected from the group consisting of a liquid bee-ingestible composition and a solid bee-ingestible composition to the host bee.

In aspects according to the present disclosure a trigger polynucleotide, for example a dsRNA, is combined with an excipient. In an aspect, the trigger polynucleotide, for example dsRNA, can be provided as a ratio of trigger polynucleotide to excipient. In an aspect, the ratio is one part trigger polynucleotide to 4 parts excipient. In an aspect the ratio of trigger polynucleotide to excipient is 1:1, 1:2, 1:5, or 1:10. In other aspects, the ratio of trigger polynucleotide to excipient is 1:20, 1:25, 1:30, 1:40, or more. In an aspect, ratio of trigger polynucleotide to excipient is 1:50. In aspects according to the present disclosure, the ratio can be determined as a volume to volume (v/v) ratio, a weight:weight (w/w) ratio, or a weight:volume (w/v) ratio. In certain aspects, the ratio is expressed as a volume to volume (v/v) ratio, a weight:weight (w/w) ratio, or a weight:volume (w/v) ratio.

In aspects according to the present disclosure, the composition can comprise a weight of trigger polynucleotide, for example dsRNA, combined with an excipient. In an aspect, the trigger polynucleotide comprises a percentage of the total weight of the composition. In an aspect, the trigger polynucleotide comprises about 0.1% by weight of the composition. In an aspect, the trigger polynucleotide comprises about 0.2% by weight of the composition. In an aspect, the trigger polynucleotide comprises about 0.3% by weight of the composition. In another aspect, the trigger polynucleotide comprises about 0.4% by weight of the composition. In an aspect, the trigger polynucleotide comprises up to 0.5% by weight of the composition. In an aspect, the trigger polynucleotide comprises up to 0.6% by weight of the composition. In an aspect, the trigger polynucleotide comprises up to 0.7% by weight of the composition. In an aspect, the trigger polynucleotide comprises up to 0.8% by weight of the composition. In another aspect, the trigger polynucleotide comprises up to 1.0% by weight of the composition. In other aspects, the trigger polynucleotide comprises up to 1.5% by weight of the composition. In yet other aspects, the trigger polynucleotide comprises up to 2.0% by weight, or 2.5% by weight of the composition.

The present disclosure provides for, and includes, compositions having from 0.1% to 5% by weight trigger polynucleotide. In other aspects, a composition comprises from 0.1 to 4%, 0.1 to 3%, 0.1 to 2%, 0.1 to 1%, 0.1 to 2%, 0.1 to 3%, or 0.1 to 4% by weight trigger polynucleotide. In an aspect, a composition comprises from 0.2% to 5% by weight trigger polynucleotide. In other aspects, a composition comprises from 0.2 to 4%, 0.2 to 3%, 0.2 to 2%, 0.2 to 1%, 0.2 to 2%, 0.2 to 3%, or 0.2 to 4% by weight trigger polynucleotide. In other aspects, a composition comprises up to 1%, up to 2%, up to 3%, up to 4%, or up to 5% trigger polynucleotide. In other aspects, a composition comprises up to 7.5%, up to 10%, or up to 15% trigger polynucleotide.

The present disclosure provides for, and includes, compositions having from 0.01 to 20 mg/ml trigger polynucleotide. In some aspects, a composition comprises from 0.01 to 0.1 mg/ml, 0.01 to 1.0 mg/ml, 0.01 to 2.0 mg/ml, 0.01 to 2.5 mg/ml, 0.01 to 5 mg/ml, 0.01 to 10 mg/ml, 0.01 to 15 mg/ml, or 0.01 to 20 mg/ml trigger polynucleotide. In other aspects, a composition comprises from 0.1 to 1.0 mg/ml, 0.1 to 2.0 mg/ml, 0.1 to 2.5 mg/ml, 0.1 to 5 mg/ml, 0.1 to 10 mg/ml, 0.1 to 15 mg/ml, or 0.1 to 20 mg/ml trigger polynucleotide. In certain aspects, a composition comprises at least 0.01 µg/ml trigger polynucleotide. In certain aspects, a composition comprises at least 0.1 µg/ml trigger polynucleotide. In certain other aspects, a composition comprises at least 1.0 µg/ml trigger polynucleotide. In yet other aspects, a composition comprises at least 10 µg/ml trigger polynucleotide. In yet other aspects, a composition comprises at least 15 µg/ml trigger polynucleotide. In yet other aspects, a composition comprises at least 20 µg/ml trigger polynucleotide. In an aspect, a composition comprises from 0.01 to 0.5 mg/ml trigger polynucleotide. In an aspect, a composition comprises from 0.5 to 10 mg/ml trigger polynucleotide. In other aspects, a composition comprises from 0.5 to 1.0 mg/ml, 0.5 to 2.0 mg/ml, 0.5 to 2.5 mg/ml, 0.5 to 5 mg/ml, 0.5 to 10 mg/ml, 0.5 to 15 mg/ml, or 0.5 to 20 mg/ml trigger polynucleotide. In an aspect, a composition comprises from 1.0 to 10 mg/ml trigger polynucleotide. In other aspects, In other aspects, a composition comprises from 0.01 to 0.02 mg/ml, 0.02 to 0.03 mg/ml, 0.03 to 0.04 mg/ml, 0.04 to 0.05 mg/ml, 0.05 to 0.06 mg/ml, 0.06 to 0.07 mg/ml, 0.07 to 0.08 mg/ml, 0.08 to 0.09 mg/ml, 0.09 to 0.1 mg/ml, 0.1 to 0.2 mg/ml, 0.2 to 0.3 mg/ml, 0.3 to 0.4 mg/ml, 0.4 to 0.5 mg/ml, 0.5 to 0.6 mg/ml, 0.6 to 0.7 mg/ml, 0.7 to 0.8 mg/ml, 0.8 to 0.9 mg/ml, 0.9 to 1.0 mg/ml, 1.0 to 2.0 mg/ml, 1.0 to 2.5 mg/ml, 2.0 to 3.0 mg/ml, 3.0 to 4.0 mg/ml, 4.0 to 5.0 mg/ml, 5.0 to 6.0 mg/ml, 6.0 to 7.0 mg/ml, 7.0 to 8.0 mg/ml, 8.0 to 9.0 mg/ml, 9.0 to 10.0 mg/ml, 10.0 to 12.0 mg/ml, 12.0 to 13.0 mg/ml, 13.0 to 14.0 mg/ml, 14.0 to 15.0 mg/ml, 15.0 to 16.0 mg/ml, 16.0 to 17.0 mg/ml, 17.0 to 18.0 mg/ml, 18.0 to 19.0 mg/ml, 19.0 to 20.0 mg/ml, 1.0 to 5 mg/ml, 1.0 to 10 mg/ml, 1.0 to 15 mg/ml, or 1.0 to 20 mg/ml trigger polynucleotide. In some aspects, a composition comprises about 0.1 µg/ml, about 0.2 µg/ml, about 0.5 µg/ml, about 1.0 µg/ml, about 2.0 µg/ml, about 5.0 µg/ml, about 10 µg/ml, about 0.02 mg/ml, about 0.05 mg/ml, about 0.1 mg/ml, about 0.125 mg/ml, about 0.2 mg/ml, about 0.25 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.5 mg/ml, about 2.0 mg/ml, about 2.5 mg/ml, about 3.0 mg/ml, about 3.5 mg/ml, about 4.0 mg/ml, about 4.5 mg/ml, about 5.0 mg/ml, about 5.5 mg/ml, about 6.0 mg/ml, about 6.5 mg/ml, about 7.0 mg/ml, about 7.5 mg/ml, about 8.0 mg/ml, about 8.5 mg/ml, about 9.0 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, or about 20 mg/ml trigger polynucleotide.

In some aspects, a composition comprises from about 1 mg to about 2000 mg trigger polynucleotide per bee colony. In certain aspects, a composition comprises from about 1 mg to about 100 mg, from about 1 mg to about 200 mg, from about 1 mg to about 300 mg, from about 1 mg to about 400 mg, from about 1 mg to about 500 mg, from about 1 mg to about 600 mg, from about 1 mg to about 700 mg, from about 1 mg to about 800 mg, from about 1 mg to about 900 mg, from about 1 mg to about 1000 mg, from about 1 mg to about 1200 mg, from about 1 mg to about 1500 mg, from about 1 mg to about 1800 mg, from about 10 mg to about 100 mg, from about 10 mg to about 200 mg, from about 10 mg to about 300 mg, from about 10 mg to about 400 mg, from about 10 mg to about 500 mg, from about 10 mg to about 600 mg, from about 10 mg to about 700 mg, from about 10 mg to about 800 mg, from about 10 mg to about 900 mg, from about 10 mg to about 1000 mg, from about 10 mg to about 1200 mg, from about 10 mg to about 1500 mg, from about 10 mg to about 1800 mg, or from about 10 mg to about 2000 mg trigger polynucleotide per bee colony. In other aspects, a composition comprises about 1 mg, about 5 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg trigger polynucleotide per bee colony.

The present disclosure provides for, and includes, methods for reducing the viral load of an organism. In some embodiments, the organism is a parasite. In an aspect, the viral load refers to the number of viruses per individual host. In an aspect, the viral load refers to the average number of viruses per 100 host organisms. In an aspect, the viral load refers to the number of viruses per colony of parasite hosts. In another aspect, the viral load is determined by measuring the viral expression in a host, such as a bee or a *Varroa* mite. In aspects according to the present disclosure the parasite is *Varroa destructor* and the host is the honey bee, *Apis mellifera*.

In one aspect, the methods of reducing viral infection comprises providing an effective amount of a trigger, for example dsRNA, composition to a host organism on which a parasite feeds. In another aspect, the methods of reducing viral infection comprises providing an effective amount of a trigger, for example dsRNA, composition directly to a parasitic organism. In aspects according to the present disclosure the parasite is *Varroa destructor* and the host is the honey bee, *Apis mellifera*. An effective amount of a composition of the present disclosure results in a decrease in viral infection in the host and/or parasite over a period of time. In an aspect, a decrease in viral infection can be measured within one day or within two days of providing an effective amount of a trigger, for example dsRNA, composition. In an aspect, viral infection can be measured after two days. In an aspect, viral infection can be measured after 3 days. In other aspects, viral infection can be measured after 4 days, after 5 days, after 6 days, after 7 days, after 1 week, after two weeks, after 3 weeks, or after a month. In another aspect, viral infection can be measured more than one time, for example, every day, every 2 days, every 3 days, every 4 days, every 5 days, every 6 days, every 7 days, every week, every two weeks, every three weeks, once a week, twice a week, three times a week, once a month, twice a month, or three times a month. In certain aspects, according to the present disclosure, a decrease in viral infection can be measured and compared to an untreated control host organism, parasite, or colony. In aspects according to the present disclosure the parasite is *Varroa destructor* and the host is the honey bee, *Apis mellifera*.

In one aspect, the methods of reducing viral replication comprises providing an effective amount of a trigger, for example dsRNA, composition to a host organism on which a parasite feeds. In another aspect, the methods of reducing viral replication comprises providing an effective amount of a trigger, for example dsRNA, composition directly to a parasitic organism. In aspects according to the present disclosure the parasite is *Varroa destructor* and the host is the honey bee, *Apis mellifera*. An effective amount of a composition of the present disclosure results in a decrease in viral gene expression in the host and/or parasite over a period of time. In an aspect, a decrease in viral gene expression can be measured within one day or within two days of providing an effective amount of a trigger, for example dsRNA, composition. In an aspect, viral replication can be measured after two days. In an aspect, viral replication may be measured after 3 days. In other aspects, viral replication can be measured after 4 days, after 5 days, after 6 days, after 7 days, or after 1 week, after two weeks, after 3 weeks, or after a month. In another aspect, viral replication can be measured more than one time, for example, every day, every 2 days, every 3 days, every 4 days, every 5 days, every 6 days, every 7 days, every week, every two weeks, every three weeks, once a week, twice a week, three times a week, once a month, twice a month, or three times a month. In certain aspects, according to the present disclosure, a decrease in viral replication can be measured and compared to an untreated control host organism, parasite, or colony. In aspects according to the present disclosure the parasite is *Varroa destructor* and the host is the honey bee, *Apis mellifera*.

In one aspect, the methods of reducing a viral load comprises providing an effective amount of a trigger, for example dsRNA, composition to a host organism on which a parasite feeds. In another aspect, the methods of reducing a viral load comprises providing an effective amount of a trigger, for example dsRNA, composition directly to a parasitic organism. In aspects according to the present disclosure the parasite is *Varroa destructor* and the host is the honey bee, *Apis mellifera*. An effective amount of a composition of the present disclosure results in a decrease in the viral load in the host and/or parasite over a period of time. In an aspect, a decrease in viral load is measured within one day or within two days of providing an effective amount of a trigger, for example dsRNA, composition. In an aspect, the viral load can be measured after two days. In an aspect, the viral load can be measured after 3 days. In other aspects, the viral load can be measured after 4 days, after 5 days, after 6 days, after 7 days, after 1 week, after two weeks, after three weeks, or after a month. In another aspect, the viral load can be measured more than one time, for example, every day, every 2 days, every 3 days, every 4 days, every 5 days, every 6 days, every 7 days, every week, every two weeks, every three weeks, once a month, twice a month, or three times a month. In certain aspects, according to the present disclosure, a decrease in the viral load can be measured and compared to an untreated control host organism, parasite, or colony. In aspects according to the present disclosure the parasite is *Varroa destructor* and the host is the honey bee, *Apis mellifera*.

In some aspects according to the present disclosure, a reduction in viral load or a reduction in viral infection after a period of time means a decrease in viral titer. In an aspect, viral titer is decreased by about 10%, 20%, 30% or more between measurements. In another aspect, viral titer is decreased by about 40% or more between measurements. In another aspect, viral titer is decreased by about 50% or more between measurements. In another aspect, viral titer is decreased by about 60% or more between measurements. In another aspect, viral titer is decreased by about 70% or more between measurements. In another aspect, viral titer is decreased by about 80% or more between measurements. In another aspect, viral titer is decreased by about 90% or more between measurements. In some embodiments, the viral titer in a host organism or a parasite provided with an effective amount of a trigger polynucleotide is decreased by at least about 10%, 20%, 30%, 40%, 50%, 60%, 70%, 80%, or 90% compared with the viral titer in a host organism or a parasite that is not provided with the trigger polynucleotide. In some embodiments, the viral titer is measured within 1 day, within 2 days, after 2 days, after 3 days, after 4 days, after 5 days, after 6 days, after 7 days, or after 1 week, after 2 weeks, after 3 weeks, or after a month of providing the trigger polynucleotide. In some embodiments, the viral titer is measured more than once. In some embodiments, the viral titer is measured every day, every 2 days, every 3 days, every 4 days, every 5 days, every 6 days, every 7 days, every week, every two weeks, every three weeks, once a month, twice a month, or three times a month. In one aspect, the host organism is a bee. In one aspect, the parasite is *Varroa destructor*.

In some aspects according to the present disclosure, a reduction in viral load or a reduction in viral infection after a period of time means a decrease in viral expression. In an aspect, viral expression is decreased by about 10%, 20%, 30% or more between measurements. In another aspect, viral expression is decreased by about 40% or more between measurements. In another aspect, viral expression is decreased by about 50% or more between measurements. In another aspect, viral expression is decreased by about 60% or more between measurements. In another aspect, viral expression is decreased by about 70% or more between measurements. In another aspect, viral expression is decreased by about 80% or more between measurements. In another aspect, viral expression is decreased by about 90% or more between measurements. In some embodiments, the viral expression in a host organism or a parasite provided with an effective amount of a trigger polynucleotide is decreased by at least about 10%, 20%, 30%, 40%, 50%, 60%, 70%, 80%, or 90% compared with the viral expression in a host organism or a parasite that is not provided with the trigger polynucleotide. In some embodiments, the viral expression is measured within 1 day, within 2 days, after 2 days, after 3 days, after 4 days, after 5 days, after 6 days, after 7 days, or after 1 week, after 2 weeks, after 3 weeks, or after a month of providing the trigger polynucleotide. In some embodiments, the viral expression is measured more than once. In some embodiments, the viral expression is measured every day, every 2 days, every 3 days, every 4 days, every 5 days, every 6 days, every 7 days, every week, every two weeks, every three weeks, once a month, twice a month, or three times a month. In one aspect, the host organism is a bee. In one aspect, the parasite is *Varroa destructor*.

In some aspects according to the present disclosure, a reduction in viral load or a reduction in viral infection after a period of time means a decrease in viral replication. In an aspect, viral replication is decreased by about 10%, 20%, 30% or more between measurements. In another aspect, viral replication is decreased by about 40% or more between measurements. In another aspect, viral replication is decreased by about 50% or more between measurements. In another aspect, viral replication is decreased by about 60% or more between measurements. In another aspect, viral replication is decreased by about 70% or more between measurements. In another aspect, viral replication is decreased by about 80% or more between measurements. In another aspect, viral replication is decreased by about 90% or more between measurements. In some embodiments, the viral replication in a host organism or a parasite provided with an effective amount of a trigger polynucleotide is decreased by at least about 10%, 20%, 30%, 40%, 50%, 60%, 70%, 80%, or 90% compared with the viral replication in a host organism or a parasite that is not provided with the trigger polynucleotide. In some embodiments, the viral replication is measured within 1 day, within 2 days, after 2 days, after 3 days, after 4 days, after 5 days, after 6 days, after 7 days, or after 1 week, after 2 weeks, after 3 weeks, or after a month of providing the trigger polynucleotide. In some embodiments, the viral replication is measured more than once. In some embodiments, the viral replication is measured every day, every 2 days, every 3 days, every 4 days, every 5 days, every 6 days, every 7 days, every week, every two weeks, every three weeks, once a month, twice a month, or three times a month. In one aspect, the host organism is a bee. In one aspect, the parasite is *Varroa destructor*.

In aspects according to the present disclosure, a reduction in viral load after a period of time results in a decrease in bee mortality. In an aspect, bee mortality is decreased by 10%, 20%, 30% or more between measurements. In another aspect, bee mortality is decreased by 40% or more between measurements. In another aspect, bee mortality is decreased by 50% or more between measurements. In another aspect, bee mortality is decreased by 60% or more between measurements. In another aspect, bee mortality is decreased by 70% or more between measurements. In another aspect, bee mortality is decreased by 80% or more between measurements. In another aspect, bee mortality is decreased by 90% or more between measurements. In some embodiments, bee mortality in a bee colony provided with an effective amount of a trigger polynucleotide is decreased by at least about 10%, 20%, 30%, 40%, 50%, 60%, 70%, 80%, or 90% compared with bee mortality in a bee colony that is not provided with the trigger polynucleotide. In some embodiments, bee mortality is measured within 1 day, within 2 days, after 2 days, after 3 days, after 4 days, after 5 days, after 6 days, after 7 days, or after 1 week, after 2 weeks, after 3 weeks, or after a month of providing the trigger polynucleotide. In some embodiments, bee mortality is measured more than once. In some embodiments, bee mortality is measured every day, every 2 days, every 3 days, every 4 days, every 5 days, every 6 days, every 7 days, every week, every two weeks, every three weeks, once a month, twice a month, or three times a month.

In aspects according to the present disclosure, an effective amount of trigger polynucleotide, for example dsRNA, can be provided periodically or continually. In an aspect, an effective amount of a trigger, for example dsRNA, composition can be provided once, twice or three times a day. In other aspects, an effective amount of a trigger, for example dsRNA, composition can be provided once a day. In another aspect, an effective amount of a trigger, for example dsRNA, composition can be provided one or more times every other day. In an aspect, an effective amount of a trigger, for example dsRNA, composition can be provided every two days, every three days, every four days, every five days, every six days, or once a week. In an aspect, an effective amount of a trigger, for example dsRNA, composition can be provided continuously to an organism in need, for example by providing a continuous source of food. In one aspect, an effective amount of a trigger, for example dsRNA, composition can be provided continuously as a bee-ingestible composition. In one aspect, an effective amount of a trigger, for example dsRNA, composition can be provided to a host organism. In another aspect, an effective amount of a trigger, for example dsRNA, composition can be provided directly to a parasitic organism. In aspects according to the present disclosure the parasite is *Varroa destructor* and the host is the honey bee, *Apis mellifera*.

The present disclosure provides for methods of reducing the viral load of a honey bee colony comprising providing a bee colony an effective amount of a trigger, for example dsRNA, composition. An effective amount of a trigger polynucleotide composition of the present disclosure results in a reduction of viral gene expression and viral replication over a period of time. In an aspect, a reduction of viral replication or viral expression is measured within one day or within two days of providing an effective amount of a trigger, for example dsRNA, composition. In an aspect, the reduction of viral replication or viral expression can be measured after two days. In an aspect, the reduction of viral replication or viral expression can be measured after 3 days. In other aspects, the reduction of viral replication or viral expression can be measured after 4 days, after 5 days, after 6 days, after 7 days, after 1 week, after two weeks, after three weeks, or after a month. In another aspect, the reduction of viral replication or viral expression can be measured more than one time, for example every day, every 2 days, every 3 days, every 4 days, every 5 days, every 6 days, every 7 days, every week, every two weeks, every three weeks, once a month, twice a month, or three times a month. In certain aspects, according to the present disclosure, a reduction of viral replication or viral expression can be measured and compared to an untreated control host organism, parasite, or colony.

In an aspect, the present disclosure provides for methods and compositions for reducing the susceptibility of bees to viral infection. In other aspects, the present disclosure provides for methods and compositions to prevent viral infection of colonies of bees. In another aspect, the present disclosure provides methods for reducing the viral infection of honeybees transmitted by the mite *Varroa destructor*.

The following Examples are presented for the purposes of illustration and should not be construed as limitations.

Example 1

To test the effect of dsRNA targeting bee viruses in *Varroa*, the mites were placed on diet plates supplemented with a mix of dsRNA triggers. A non-specific dsRNA having no sequence identity above 19 bp to *Varroa* genes was used as a non-specific control (SCRAM; SEQ ID NO:24). *Varroa* mites were collected, RNA extracted and DWV or IAPV expression analyzed using quantitative reverse transcription PCR (Q-PCR).

Experimental Process

First, an artificial diet was prepared as follows in Table 1:

TABLE 1

| Artificial Diet Components | | | |
|---|---|---|---|
| Reagent | control | Non specific control | dsRNA mix |
| Standard LB 1X | 1X | 1X | 1X |
| Antibiotic Antimycotic Solution (100x), Stabilized (SIGMA A5955) | | Diluted 1:100 to 1X | |
| Nystatin [5 mg/ml] | | Diluted 1:100 | |
| KAN [50 mg/ml] | | Diluted 1:20 | |
| 1XPB | | To 1 mL | |
| Scrambled Control dsRNA (SCRAM) [9 mg/ml] | | 200 µg/mL | |
| dsRNA mix | | | 200 µg/mL |

In one experiment, the dsRNA trigger mix contained a mixture of SEQ ID NOs: 1-10 from the following dsRNA sequences:

TABLE 2 dsRNA trigger sequences used in *Varroa* direct feeding assays

| SEQ ID NO: | Source Seq | Sense | Protein |
|---|---|---|---|
| 1 | IAPV Genome | GAUACAUUGAAAGAUGAGCGUCGACCCAUUGAAAAAGUU AAUCAAUUGAAAACACGAGUAUUCUCAAAUGGACCAAUG GAUUUCUCUAUAGCUUUUCGAAUGUAUUAUUUGGGCUUU AUAGCUCAUUUGAUGGAAAAUCGAAUUACUAAUGAGGUG UCCAUUGGAACGAAUGUGUAUUCUCAAGACUGGAGUAAA ACUGUUCGUAAGUUGACUAAAAUUUGGAAAUAAAGUUAU UGCAGGUGAUUUUUCAACUUUUGAUGGAUCACUGAAUGU AUGUAUUAUGGAAAAAUUUGC | RdRp (not IR) |
| 2 | IAPV Genome | GAAACUCCAAAUAGGAUCGAUACCCCCAUGGCUCAGGAU ACUUCAUCGGCUAGGAACAUGGAUGAUAC | VP2 |
| 3 | IAPV Genome | GACGGACCUUCACAUAUAACAUACCCCGUAAUCAAUCCU GUGCAUGAAGUAGAAGUUCCAUUCUAUUCUCAGUAUAGG AAAAUACCUAUCGCUUCAACAUCGGAUAAAGGUUAUGAU UCCUCUCUAAUGUAUUUUCAAAUACAGCAACAACUCAA AUUGUUGCCAGAGCAGGAAACGAUGACUUUACUUUGGU UGGAUGAUAGGUC | VP1 (CP) |
| 4 | IAPV Genome | GCCCCCUAGAUGUGCACUGGGAGACAGACAAAUCUCCCU AUGUAUGGCUAUAGUCUAAAUUUUUCACAAAAUUUCAGU UUAGACCGAAAACCGACAC | VP1 (CP) |
| 5 | DWV Genome | GAAGAAAUAUAUAGCUACGUGGUGUAGUAAGCGUCGUGA ACAUACUGCUGACUUUGAUCUU | Helicase to VPg |
| 6 | DWV Genome | GCUCCCAAUGCUGAAGCGGAGGAGGCAAGUGCUUGGGUA UCCAUUAUUUAUAAUGGUGUGUGUAAUAUGCUUAAUGU GGCUGCUCAAAAACCGAAACAAUUUAAAGAUUGGGUAAA AUUAGCUACUGUAGAUUUUAGUAAUAAUUGUAGAGGUA GUAAUCAGGUAUUUGUAUUUUUCAAGAAAUACAUUUGAA GUGUUGAAGAAAAUGUGGGGUUAUGUAUUUUGUCAGAG UAAUCCUGCAGCGCGUUUGUUGAAAGCUGUGAAUGACGA GCCUGAGAUUUUGAAAGC | Helicase |
| 7 | DWV Genome | GAAAGCUGUGAAUGACGAGCCUGAGAUUUUGAAAGCAUG GGUGAAGGAAUGUC | Helicase |
| 8 | DWV Genome | GGTACAGTTTACCATACCGTTTCGACAGTATTACTTAGACT TTATGGCATCCTATCGAGCTGCACGACTTAATGCTGAGCAT GGTATTGGTATTGATGTTAACAGCTTAGAGTGGACAAATTT GGCAAC | RdRp |
| 9 | DWV Genome | GAAUGGAUAACUCCUGUGUAUAUGGCUAACCGUCGUAAG GCGAAUGAAUCGUUUAAGAUGCGUGUAGAUGAAAUGCAA AUGUUACGUAUGGAUGAACCAUUGGAAGGUGAUAAUAU UCUCAAUAAGUAUGUUGAAGUUAAUCAGCGCUUAGUGGA GGAAAUGAAGGCAUUUAAGGAGCGUACACUAUGGUCAGA UUUACAUCGC | Helicase |

TABLE 2 -continued dsRNA trigger sequences used in *Varroa* direct feeding assays

| SEQ ID NO: | Source Seq | Sense | Protein |
|---|---|---|---|
| 10 | IAPV Genome | GAAACACAAAAUCACAACGCUUUAAUGAAAGGAUGUGGU GAGUUUAUUGUAAACUUGCGAACUCUUCUCAGAACCUUU AGAACAAUAACAGAUAAUUGGAUAUUACAAGC | VP1 (not CP) |

After plates cooled down, 15 *Varroa* mites were placed on each plate. Then the plates were sealed with absorbance paper, parafilm and incubated for 72 h in an incubator at 29° C. Following 72 h on LB agar containing treatment, dead/alive mites were counted. As shown in FIG. 2A, the bee viruses trigger mix was not observed to have an effect on *Varroa* mite mortality.

Both live and dead *Varroa* were collected for RNA extraction and bee virus levels and replication were analyzed by Q-PCR or QuantiGene® Plex 2.0 (RNA assay platform from Affymetrix). FIG. 2B shows decreased DWV levels in *Varroa* 72 h following treatment with the bee viruses trigger mix compared to control, as analyzed by Q-PCR.

Example 2

To test the effect of dsRNA targeting bee viruses on viral load (IAPV or DWV) in honeybees and *Varroa* mites in a minihive environment, the honeybees are placed on a diet supplemented with one or more dsRNA triggers (e.g., SEQ ID NOs: 1-10 and 21) targeting bee virus genes. A non-specific dsRNA having no sequence identity above 19 bp to *Varroa* genes is used as a non-specific control (SCRAM, e.g., SEQ ID NOs:22, 23, or 24). The blank control contains no dsRNA.

Bee hives with high viral load and *Varroa* load are identified. Minihives are then assembled with 400-600 bees (2 cups) from the identified high *Varroa* mite and high viral load hives, foundation frames, and queen in queen-cell with a few escort-bees. The queen cell is sealed with candy. While filling the hives, time zero samples of bees and *Varroa* are collected (1 cup of bees from each hive). The samples are frozen (−70° C.), *Varroa* mites are collected from frozen cups and samples of bees and *Varroa* are prepared for Q-PCR or QuantiGene® analysis. The viral loads in the honey bees and the *Varroa* mites are determined at the initial time point.

The Mini-hives are fed with 66% sucrose solution and protein-cakes and placed in a net house under dark cover for 24 hrs to improve queen habitation. Following queen habitation, the dark cover is removed and the bees are fed with a sugar solution containing a mix of dsRNA targeting multiple bee viruses (concentration of 1 μg/bee to 10 μg/bee).

Samples of bees are collected, 10 bees from each hive every 4-5 days. The collected bees are analyzed by QG (QuantiGene® Plex 2.0 RNA assay platform from Affymetrix) to determine viral load. Viral load is decreased in bees fed dsRNA targeting bee viruses compared to bees fed a diet supplemented with non-specific dsRNA.

*Varroa* are collected from each hive every 4-5 days by sugar shake: one cup of bees from each minihive and two spoons of sugar powder are placed into a container with a punched sealer. The cup is shaken and turned top to bottom—the *Varroa* mites fall through the holes in the sealer and bees stay in the cup. Bees are returned into the minihive and *Varroa* are analyzed by QG (QuantiGene® Plex 2.0 RNA assay platform from Affymetrix) to determine viral load. Viral load is decreased in *Varroa* collected from bees fed dsRNA targeting bee viruses compared to *Varroa* collected from bees fed a diet supplemented with non-specific dsRNA.

Quantigene®, a quantitative, non-amplification-based nucleic acid detection analysis, is performed on total lysate from frozen honey bees or *Varroa* mite samples to measure viral expression and viral replication. The oligonucleotide probes used for the QuantiGene® Plex 2.0 assay are designed and supplied by Affymetrix, using the sense strand of bee virus sequences as template or negative strand for replicating virus. Housekeeping gene probes are designed from sequences of *Apis mellifera* Actin, Ribosomal protein subunit 5 (RPS5) and Ribosomal protein 49 (RP49). The QuantiGene® assay is performed according to the manufacturer's instructions (Affymetrix, Inc., User Manual, 2010) with the addition of a heat denaturation step prior to hybridization of the sample with the oligonucleotide probes. Samples in a 20 μL volume are mixed with 5 μl of the supplied probe set in the well of a PCR microplate followed by heating for 5 minutes at 95° C. using a thermocycler. Heat-treated samples are maintained at 46° C. until use. The 25 μl samples are transferred to an Affymetrix hybridization plate for overnight hybridization. Before removing the plate from the thermocycler, 75 μl of the hybridization buffer containing the remaining components are added to each sample well. The PCR microplate is then removed from the thermocycler and the content of each well (~100 μl) is transferred to the corresponding well of a Hybridization Plate (Affymetrix) for overnight hybridization. After signal amplification, median fluorescence intensity (MFI) for each sample is captured on a Luminex 200 machine (Luminex Corporation).

Example 3

To test the effect of dsRNA targeting DWV or IAPV in honeybees and *Varroa* mites, honeybees were placed on a diet supplemented with a mixture of dsRNA triggers selected from SEQ ID NOs: 5-9 targeting DWV, and SEQ ID NOs: 1-4 and 10 targeting IAPV. A non-specific dsRNA having no sequence identity above 19 bp to *Varroa* genes was used as a control (SCRAM; SEQ ID NO:22 or 23).

Bee hives with high viral load and *Varroa* load were identified. FIG. 3 shows a sample quantification of *Varroa* load and DWV level. Minihives were then assembled with 400-600 bees (2 cups) from the identified high *Varroa* mite and high viral load hives, foundation frames, and queen in queen-cell with a few escort-bees. The queen cell was sealed with candy.

The Mini-hives were fed with 66% sucrose solution and protein-cakes and placed in a net house under dark cover for 24 hrs to improve queen habitation. After 2 days of acclimatization, bees were fed with a sugar solution only (CON), a sugar solution containing non-specific control dsRNA (SCR), or a sugar solution containing a mixture of dsRNAs targeting multiple bee viruses (SEQ ID NOs: 1-10; MIX) at concentration of 1 µg/bee to 10 µg/bee.

10 bees from each hive were collected every 4-5 days after hives were infected. The collected bees were analyzed by QuantiGene® as described in Example 2 to determine viral replication as median fluorescence intensity (MFI).

Figure 4:
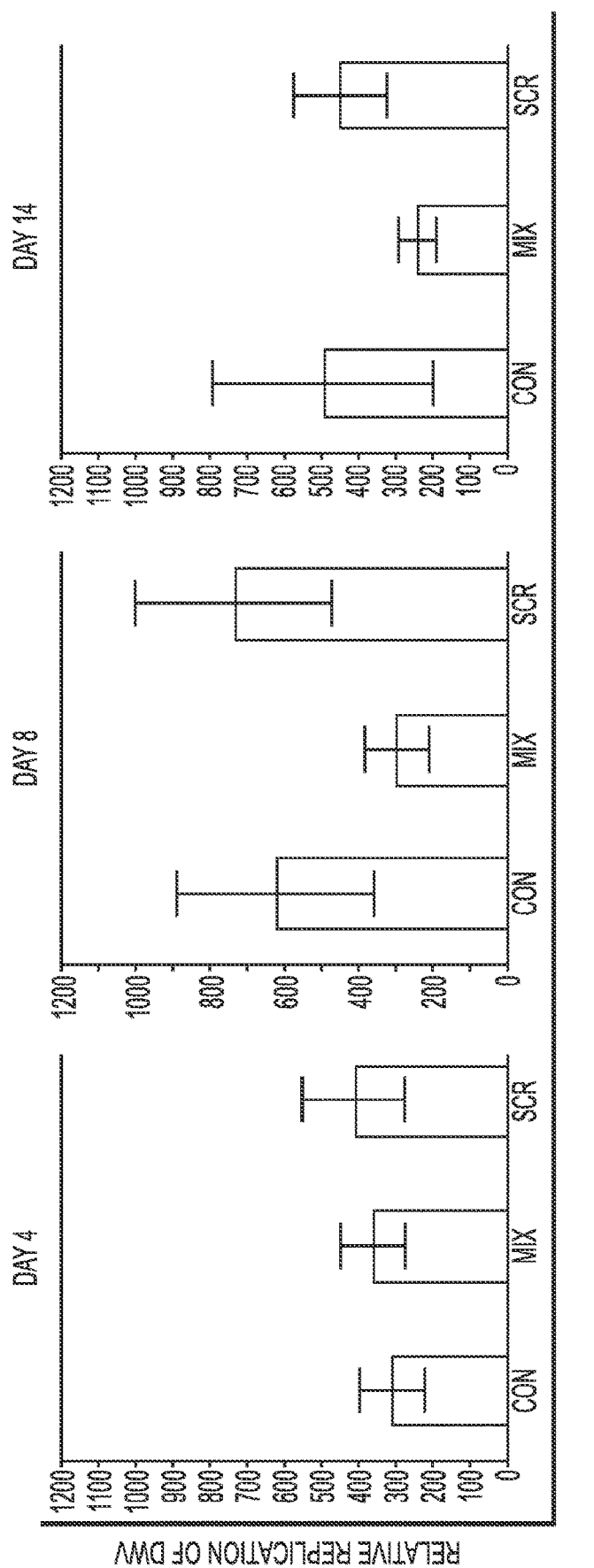
FIG. 4 depicts a graph showing DWV replication in bees 4 days, 8 days, and 14 days after the bees were fed with a mixture of dsRNA triggers (MIX), a non-specific dsRNA (SCR), or no dsRNA (CON).

FIG. 4 shows that DWV replication was decreased in all bees fed with a mixture of virus-targeting dsRNAs (MIX) compared to bees fed with sugar solution only (CON) or a diet supplemented with non-specific dsRNA (SCR). Replication of the DWV virus was measured using QuantiGene® analysis 4, 8, and 14 days following treatment in bees. The results show that from day 8, replication of DWV increased in the two controls (CON and SCR) but not in bees treated with the virus-targeting dsRNA mixture (MIX), indicating that the virus-targeting dsRNA mixture was effective in suppressing viral replication.

Example 4

This is another example of the *Varroa* direct feeding experiment as described in Example 1. To test the effect of dsRNA targeting bee viruses in *Varroa*, the mites were placed on diet plates supplemented with a mix of dsRNA triggers. A non-specific dsRNA having no sequence identity above 19 bp to *Varroa* genes was used as a non-specific control (SEQ ID NO: 22 or 23). The blank control contained no dsRNA. *Varroa* mites were collected, RNA extracted and DWV or IAPV expression analyzed using QuantiGene® analysis Plex 2.0 (RNA assay platform from Affymetrix).

Experimental Process

First, an artificial diet was prepared as follows in Table 3:

TABLE 3

Artificial Diet Components

| Reagent | control | Non specific control | dsRNA mix |
|---|---|---|---|
| Standard LB 1X | 1X | 1X | 1X |
| Antibiotic Antimycotic Solution (100x), Stabilized (SIGMA A5955) | | Diluted 1:100 to 1X | |
| Nystatin [5 mg/ml] | | Diluted 1:100 | |
| KAN [50 mg/ml] | | Diluted 1:20 | |
| 1XPB | | To 1 mL | |
| Non-specific dsRNA [10 mg/ml] | | 1000 µg/mL | |
| dsRNA mix | | | 1000 µg/mL |

The dsRNA trigger mix contained a mixture of SEQ ID NOs: 2-6 and 8-10 (125 µg/ml from each).

After plates cooled down, 15 *Varroa* mites were placed on each plate. Then the plates were sealed with absorbance paper, parafilm and incubated for 72 h in an incubator at 29° C. Live *Varroa* were collected for RNA extraction and bee viruses levels and replication were analyzed with QuantiGene® Plex 2.0 (RNA assay platform from Affymetrix).

Figure 5A:
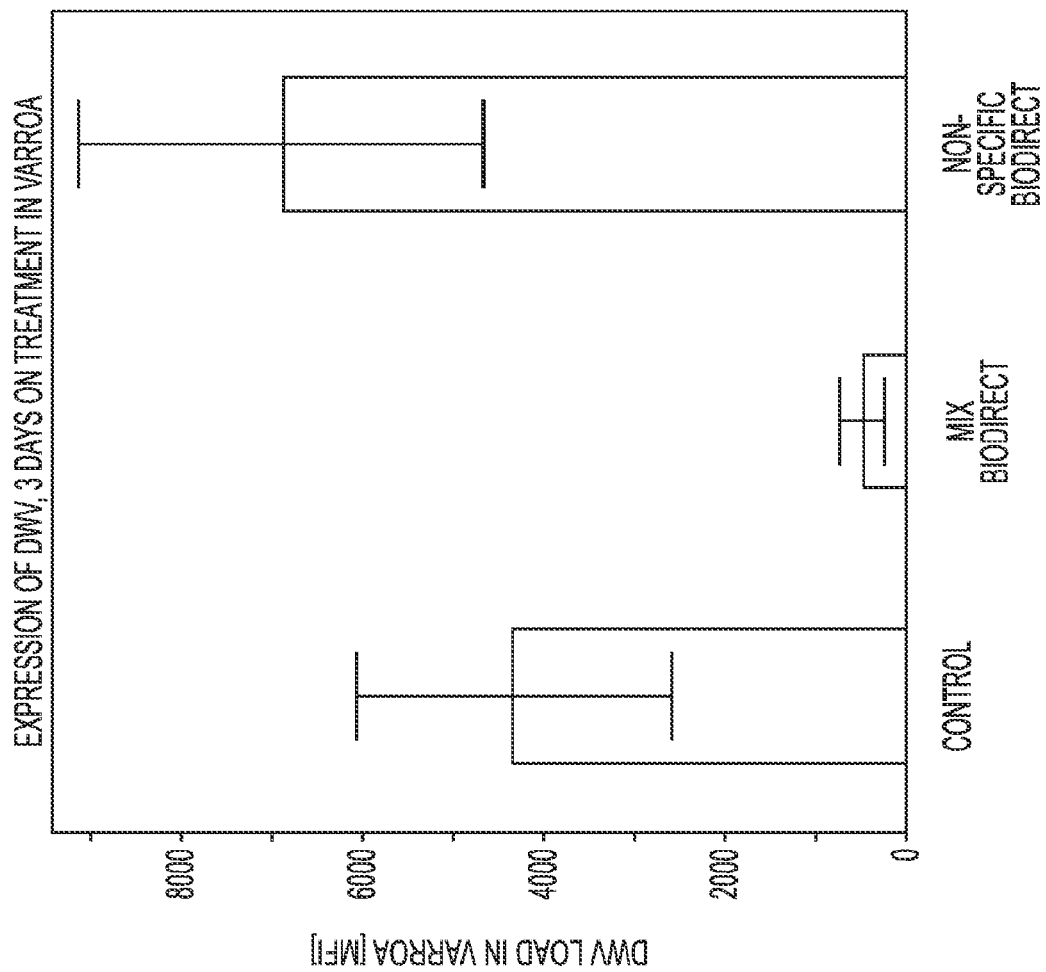
FIG. 5A depicts a graph showing DWV levels in *Varroa* 3 days following treatment in a *Varroa* direct feeding experiment, measured by QuantiGene®.

FIG. 5A shows decreased DWV levels in *Varroa* 72 h following treatment with the bee viruses trigger mix compared to both the blank control and the non-specific dsRNA. Similarly, FIG. 5B shows decreased IAPV levels in *Varroa* 72 h following treatment with the bee viruses trigger mix compared to both the blank control and the non-specific dsRNA.

Example 5

To test the effect of dsRNA targeting bee viruses on DWV viral load and replication in honeybees in a bee box environment (lab conditions), the honeybees were brought from commercial hives in the field and placed in bee boxes fed with 66% sugar syrup supplemented with either individual dsRNA triggers selected from SEQ ID NOs: 5, 6, 8, and 9 targeting DMV (T1=SEQ ID NO:5, T2=SEQ ID NO:6, T3=SEQ ID NO:8, and T4=SEQ ID NO:9) or a mixture of these dsRNA triggers. A non-specific dsRNA (SEQ ID NO:22 or 23) having no sequence identity above 19 bp to honeybee's genes was used as a non-specific control. The blank control contained no dsRNA.

Bee hives with high viral load were identified. Bee boxes were then assembled with 5 bees from the identified high viral load. While filling the boxes, time zero samples of bees were collected. The samples were frozen (-70° C.). The viral loads in the honey bees were determined at the initial time point.

The bee boxes were fed with 66% sucrose solution. Following 2 days of acclimatization, bees were fed with a sugar solution containing the individual or mixture of dsRNAs targeting DMV (concentration of 1 µg/bee to 10 µg/bee), containing the non-specific dsRNA control, or containing no dsRNA. After 3 more days, bees were fed again with the same sugar solutions.

24 bees from each group of treatment were collected after 4 and 10 days from the second treatment. The collected bees were analyzed by QuantiGene® Plex 2.0 to determine viral load and viral replication.

Figure 6A:
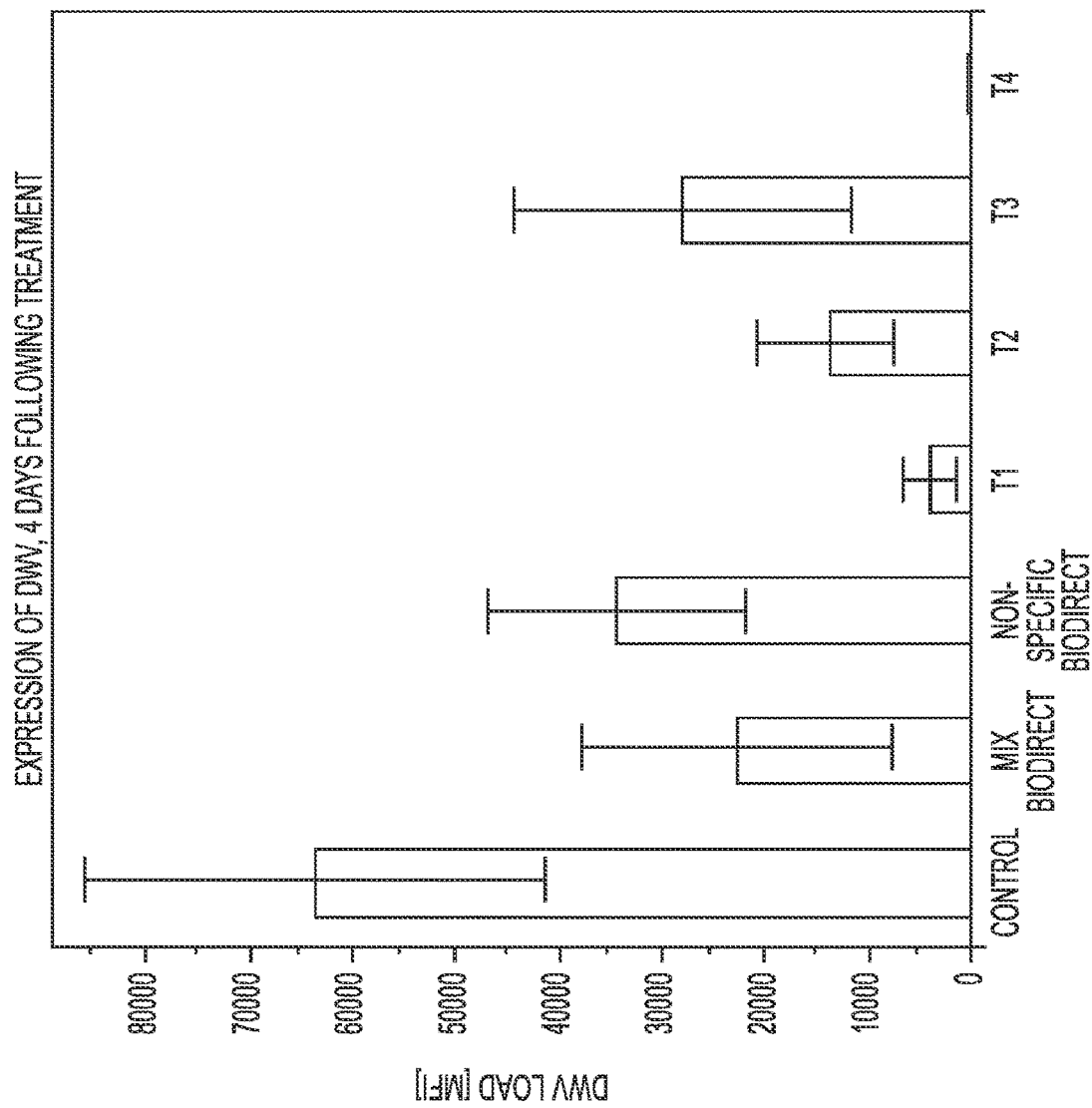
FIG. 6A depicts a graph showing DWV expression in honeybees 4 days following treatment of the bees, measured by QuantiGene®.
Figure 6B:
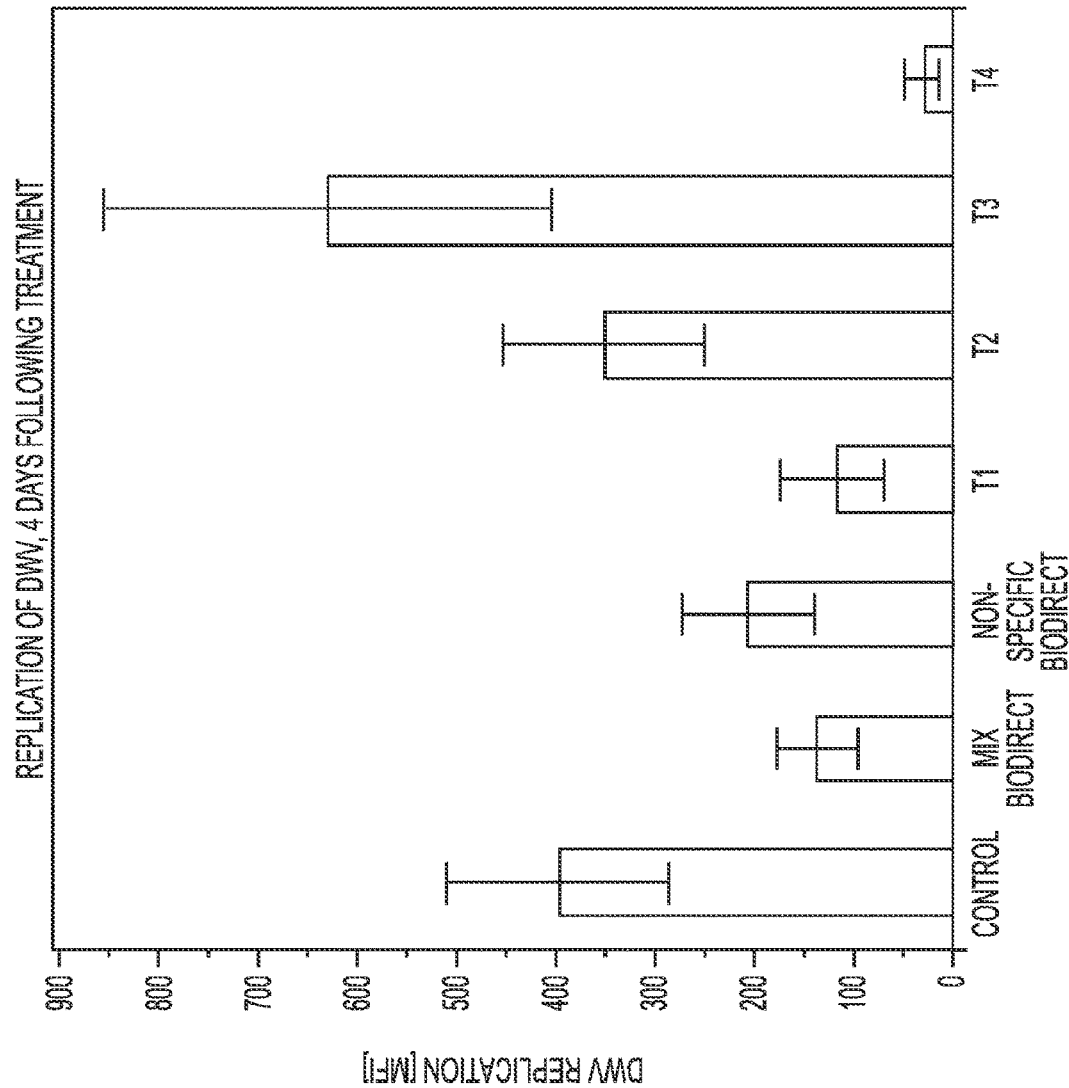
FIG. 6B depicts a graph showing DWV replication in honeybees 4 days following treatment of the bees, measured by QuantiGene®.

FIG. 6A shows that both the mixture of dsRNA triggers and the individual triggers were effective in suppressing DWV load in bees compared to the two controls, with T1 and T4 showing greater effect. FIG. 6B shows similar effects on DWV replication in bees, also with T1 and T4 showing greater effect.

Example 6

To test the effect of dsRNA targeting bee viruses on IAPV viral load and replication in honeybees in a bee box environment (lab conditions), the honeybees were brought from commercial hives in the field and placed in bee boxes fed with 66% sugar syrup supplemented with either individual dsRNA triggers selected from SEQ ID NOs: 2-4 and 10 targeting IAPV (T5=SEQ ID NO:2, T6=SEQ ID NO:3, T7=SEQ ID NO:4, and T8=SEQ ID NO:10) or a mixture of these dsRNA triggers. A non-specific dsRNA (SEQ ID NO:22 or 23) having no sequence identity above 19 bp to honeybee's genes was used as a non-specific control. The blank control contained no dsRNA.

Bee hives with high viral load were identified. Bee boxes were then assembled with 5 bees from the identified high viral load. While filling the boxes, time zero samples of bees were collected. The samples were frozen (-70° C.). The viral loads in the honey bees were determined at the initial time point.

The bee boxes were fed with 66% sucrose solution. Following 2 days of acclimatization, bees were fed with a sugar solution containing the individual or mixture of dsR- NAs targeting DMV (concentration of 1 μg/bee to 10 μg/bee), containing the non-specific dsRNA control, or containing no dsRNA. After 3 more days, bees were fed again with the same sugar solutions.

24 bees from each group of treatment were collected after 4 and 10 days from the second treatment. The collected bees were analyzed by QuantiGene® Plex 2.0 to determine viral load and viral replication.

Figure 7A:
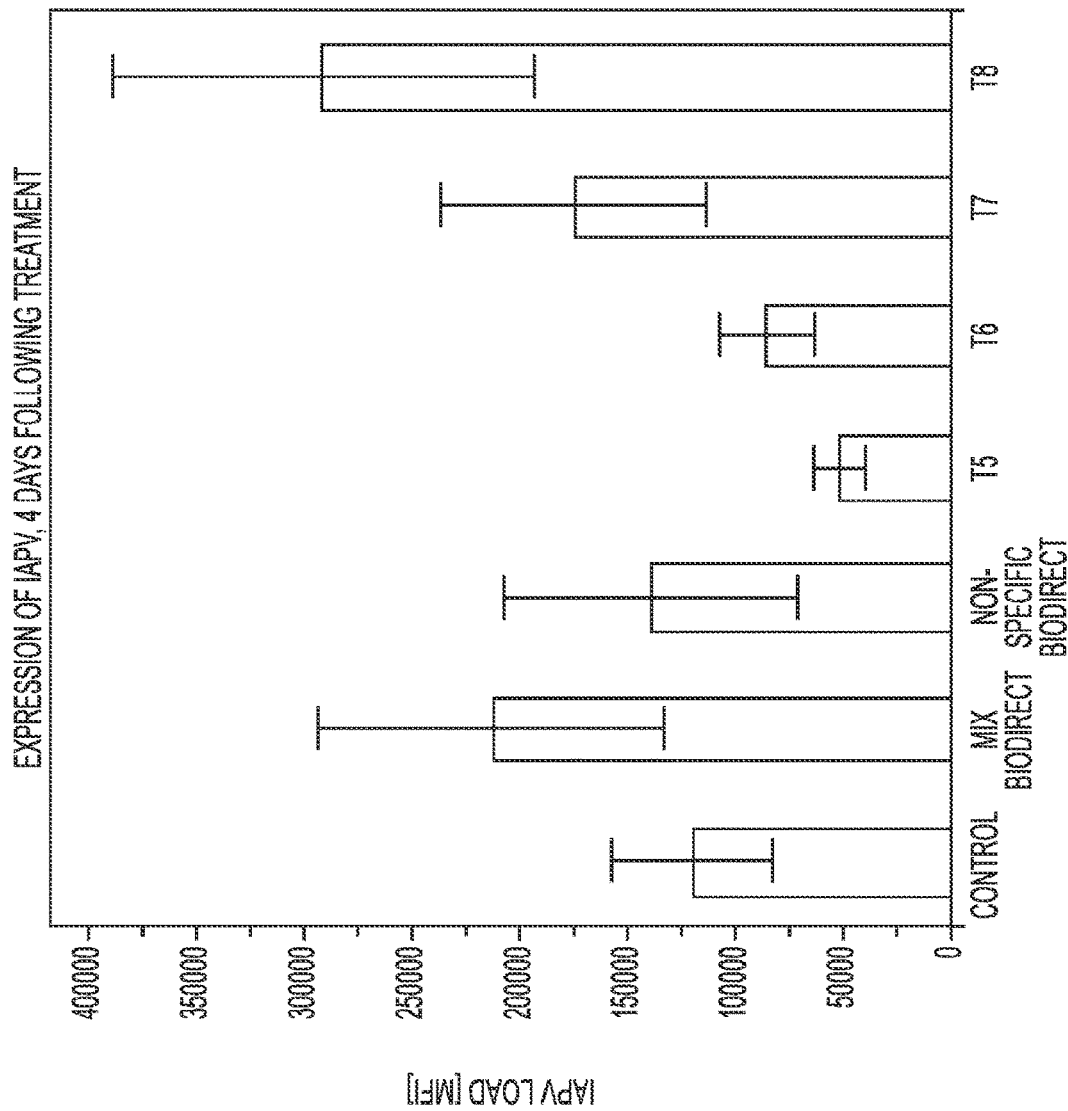
FIG. 7A depicts a graph showing IAPV expression in honeybees 4 days following treatment of the bees, measured by QuantiGene®.
Figure 7B:
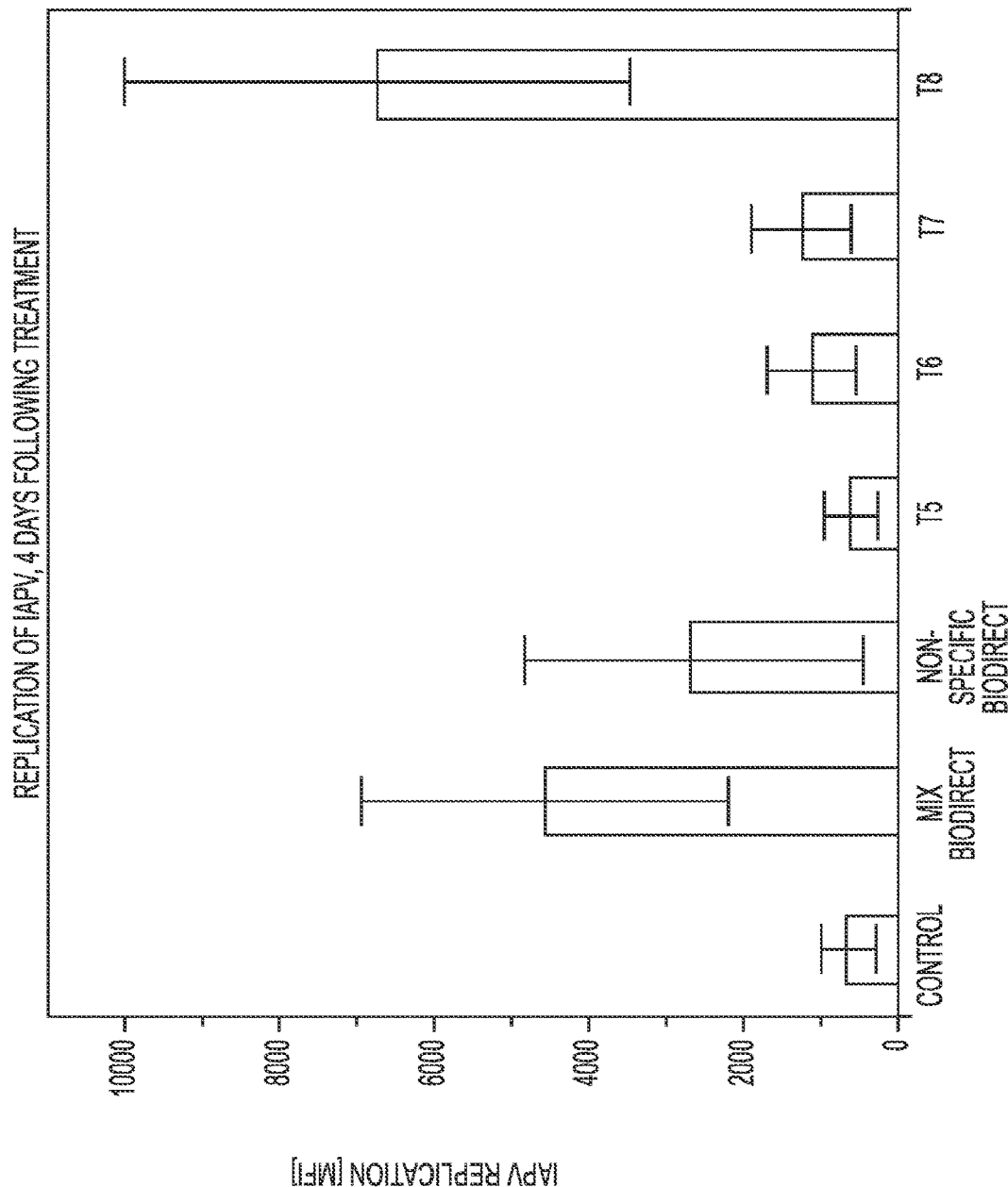
FIG. 7B depicts a graph showing IAPV replication in honeybees 4 days following treatment of the bees, measured by QuantiGene®.
Figure 8:
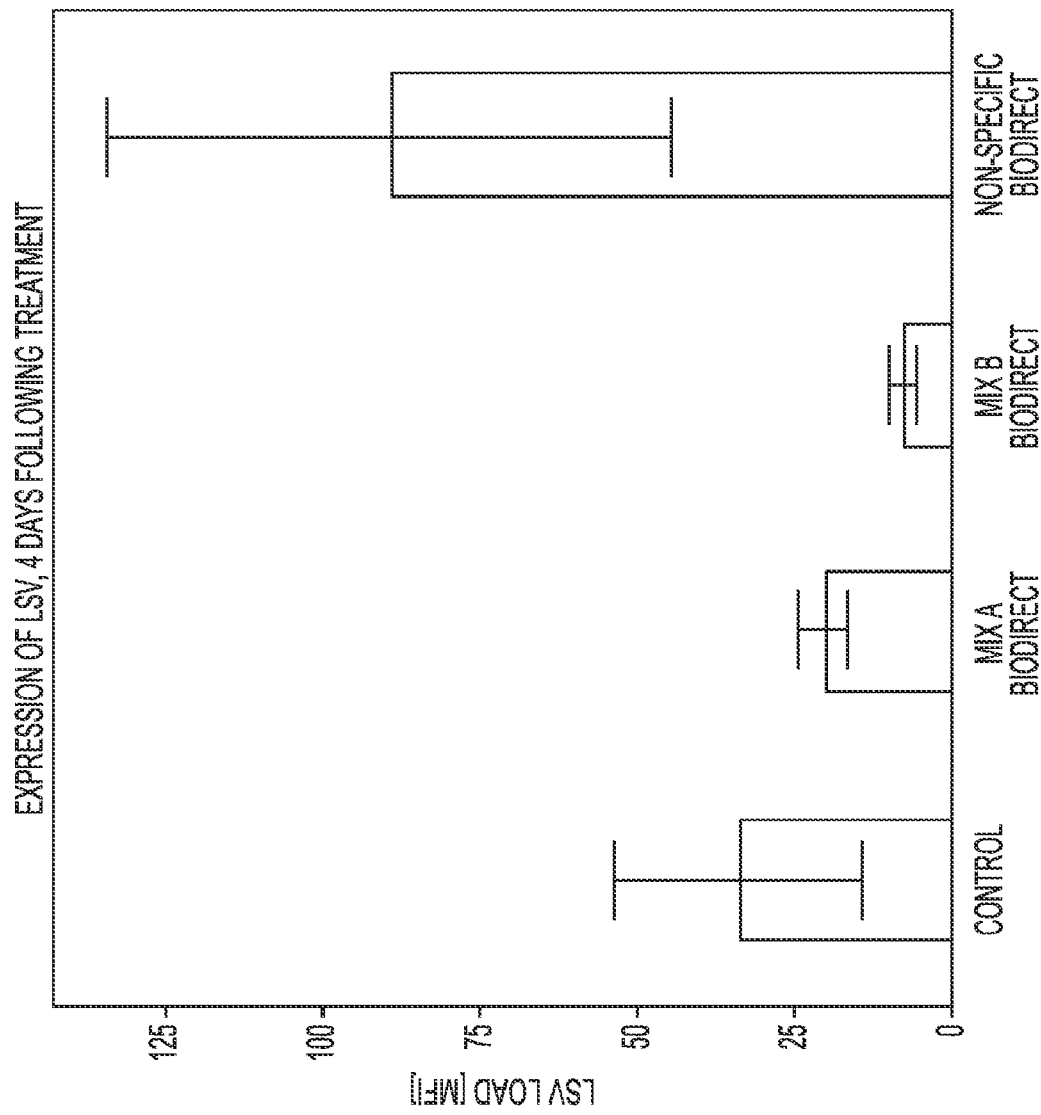
FIG. 8 depicts a graph showing LSV expression in honeybees 4 days following treatment of the bees, measured by QuantiGene®.

FIG. 7A shows that T5 and T6 were effective in suppressing IAPV load compared to the controls. FIG. 7B shows that with the exception of the mix and T8, viral replication was suppressed in all bees fed with dsRNA targeting IAPV sequences compared to bees fed with a diet supplemented with non-specific dsRNA.

Example 7

To test the effect of dsRNA targeting bee viruses on LSV viral load and replication in honeybees in a bee box environment (lab conditions), the honeybees were brought from commercial hives in the field and placed in bee boxes fed with 66% sugar syrup supplemented with a mixture of five dsRNA triggers selected from SEQ ID NOs: 11-20. Two dsRNA trigger mixes were tested. Mix A contained SEQ ID NOs:11, 13, 14, 17, and 18 and Mix B contained SEQ ID NOs:12, 15, 16, 19, and 20, having the following dsRNA sequences:

TABLE 4 dsRNA trigger sequences targeting LSV

| SEQ ID NO: | Source Seq | Sense | Protein |
|---|---|---|---|
| 11 | LSV1 genome | GCUUACAAUAACUUCGUUCACAGACACCGCGUUGCUGCCUAUGCUGCUGG CGUGCGUAUCCACCGUUACCGCACGCCGUGGUAUUGCGCCGCGUCACGGU CUGUUCCGGUCGUCCAUCCUCUUAACUGGUUGAUGACCCAGUACGAUCUU ACUACUGGCCAUGUUCGUGAAUUACUGGAUCGACUGGAGGUUGUCAAUG UUACCCUUCGUGAUGGCCUCCGCACUGUUGCUGACACUGCGUUUACAGCU UAUAUGUACUAUCAGAUAAUGUGGUGUC | RdRp + Capsid |
| 12 | LSV2 genome | GAGCAGUAUCUCCUCAAUUUAAAAUAUGUCCCCUCUACUUACCGCUAUCU CAAGCGCGAUCUCGACAUUGACGGUGUCCAUACCGCGUUGUUGGGUGAGU UUAGGUCUGUUCUUUACGCGUAAUUAAUAGAAAUUAUCACGAUGAAUCCA CCAACUACGACUACGACUACGACGCGCACCAUCCGCGCCCCAAAAGUUCA ACUGACGCCCAAUUCUGCUACUCGGCGUCGGCGUAAUCGUCGGCGCCGUC GAC | RdRp + Capsid |
| 13 | LSV1 genome | GCCUGACUAUUAUGAGAUUGAUUACUCCCGAUUCGACUUGUCUAUUAGU GCUGAAGUUAUUUCACAGUACGAGCAUGCCUGGGUCUCUCUUGUUUAUCC UCCUCUCAAUUACCCUGGCUUCUGGCAGACUCUCGUUUCGACACUCAUUA CCUCGGGCUUUAGUGAGUACGGUAUUACUUACUCUUUGCCUGGGUCACG UUGUAGCGGUGACCCACAUACGUCCGUUGGUAAUGGUUUGCUGAACGGG UUCUUAAC | RdRp |
| 14 | LSV1 genome | GCCUCGUGCGGACCUCAUUUCUUCAUGUCAGUGUGUGAGCAUGAUGAGU CAAUACCUACGGUGUUCCAUGCACACUCGGUGGGAGGUCAAGAUAUCACC CACGACAUUGAUUCAGGUUUGGGAGCAAUUAUAUCAAAACGCUUUAGUGC UUCGCAGCUACGCCUCCUUAGCUGGUCUAUCGACGGAAUACUCAACACUU UAUCUCGCGCCGCCACCUCAUCGUUUGUCGAAUCGUCGCUGUUGUCCUUG UUACGAUUUAUGC | RdRp |
| 15 | LSV2 genome | GAUUAUACCGGACUUGGGCUUCAUGCUCAAGAUCGAUCACUAUGAGCAUG UCGACGAUUGUUCGUUUUGCGGUAUGUACUUGCUGGAUGAUCGUGGAUC GCUCCGCAUGUACUCUGACCCGGUGCGCACACUGUCUAUGAUACAUGUGU GCUGCGCCGAUGGUCUACCCAACAAUUUGAUCGUGGCCAAGGCUCUGAGC CUUCUCAAUCUGAAUCCAUGUACCCCCAUCGUCACAGCCUUUUGUCGUCAC AUAUUGC | RdRp |
| 16 | LSV2 genome | GAGCAUAAUGCCGCUGGUUUACCCUUCUUAAUUAAGGGAUGUGACAUGGC GGCUCGUGCCGCCAAGAUGCGUGACCUCCUGGGGUUGGCCUCACUAUUACG AGAUCGACUACUCUCGUUUUGAUUUGUCGAUAAGUGCUGAGGUCAUAUC UCAGUUUGAGCAUGCUUGGAUCUCGUUGGUCUACGCCCCCGACAUGCACC CGCUGUUUCUGGCAGACGCUGGUCGCCACGUUGGUCACUUCAGGGUUUAG UGAGUAUGGC | RdRp |
| 17 | LSV1 genome | GAGCAGUAUCUGCUCUCAUUAUUGUUUGUUCCGUCGCGUUAUGCCUUAC UUAAACGAGACAUUGAGCUCGACGGCCUACAGACCACCCUUCUUGGCGACU UCAGGUCUGUUCUUUACGCGUGAACAUUAUAAAUUUACUAUCAUGAAUCA ACAACAAAUGAACCCCGCGCAGCGAUCGUUGCGCCCCCGCGCUCAAUCUAC UCCCUCUCGGUCCGCUCGACGACGACGCAAUCGUAGGCGCCGUAACC | RdRp |
| 18 | LSV1 genome | GCCUGGCUUCGGCAGUAUUUGAACCCUAUGGGCCCUUCUACAUCCAGUGU GAGUGGCUUUCCUGAUGGGUCUGCUGUUACCACAUGCAUUGCCGAUUACA CCAACACAUUCAAUAUCUCUUUCCCUCCUCGUGAGGCGAUUUAUUGUACC GGUUCUAAUUCUGAUGAGAAACCUGUUAUGCUGGACGCCGCCACCUAUGC UAAGAUCGACGCGUGGACUAAGUCGGAUAUCACCUUGUGCAUACUCGCCU UGCCC | RdRp |

TABLE 4 -continued dsRNA trigger sequences targeting LSV

| SEQ ID NO: | Source Seq | Sense | Protein |
|---|---|---|---|
| 19 | LSV2 genome | GUCCUAUGUUUACUUGCCGAACGUUGACAAGCACCUUUCUGCUGCCCGGG GAUACCGCUUACUGUCCCGCGGCAUCACUGGUAUCUUUAGUGCUCCUGCU CUUGAGACUCAGGGAUUCGUCACAGCUUGCCAGUAUUUGGCUGAGGGGU CUAUACAAUCUCAGUCCAUUAAGUCUGACGCUGUUCGAUCCGUCACUGUU AACAGUGAUGGUACUGUUAAGAACGUUGAGUCUAGCUCACAAACAGUUUC GUCUAUGC | Capsid |
| 20 | LSV2 genome | GAGGGCAUCUCACCUAAAUUUUCUCUCAAACUUAAGACUCGAACUGUAUU GCAAUAUAUUCCCACCUCCGGCUCUGUCUUGGCUAACUUCACCAGACACGA GCCUACUUACGAUCAGAUAGCGCUCGAUGCUGCUGAUCGUCUGCGUAACC UGAUGCCUCACGCUUACCCUGCCGCAUACAACGAUUGGGGAUGGCUUGGU GAUCUGCUCGAUUCUGCCAUCUCCAUGUUGCCGGGUGUAGGUACUGUGU AUAAC | Capsid |

A non-specific dsRNA (SEQ ID NO:22 or 23) having no sequence identity above 19 bp to honeybee's genes was used as a control. The blank control contained no dsRNA.

Bee hives with high viral load were identified. Bee boxes were then assembled with 5 bees from the identified high viral load. While filling the boxes, time zero samples of bees were collected. The samples were frozen (−70° C.). The viral loads in the honey bees were determined at the initial time point.

The bee boxes were fed with 66% sucrose solution. Following 2 days of acclimatization, bees were fed with a sugar solution containing the individual or mixture of dsRNAs targeting DMV (concentration of 1 μg/bee to 10 μg/bee), containing the non-specific dsRNA control, or containing no dsRNA. After 3 more days, bees were fed again with the same sugar solutions.

24 bees from each group of treatment were collected after 4 and 10 days from the second treatment. The collected bees were analyzed by QuantiGene® Plex 2.0 to determine viral load.

FIG. 8 shows that both Mix A and Mix B were effective in suppressing LSV load compared to the controls, with Mix B showing greater effect. LSV load was decreased in bee hives fed with a diet supplemented with dsRNA targeting LSV sequences compared to bee hives fed with a diet supplemented with non-specific dsRNA.

What is claimed is:

1. A method of reducing viral load or suppressing viral replication in a *Varroa destructor* mite infected by a virus, the method comprising providing to the *Varroa destructor* mite infected by a virus a composition comprising an effective amount of at least one double-stranded RNA (dsRNA) which comprises a nucleic acid sequence that is identical or complementary to a sequence of at least 21 contiguous nucleotides of a viral gene in said virus, wherein the dsRNA downregulates expression of said viral gene in the *Varroa destructor* mite, thereby reducing viral load or suppressing viral replication in the *Varroa destructor* mite.

2. The method of claim 1, wherein said composition comprises a mixture of 2, 3, 4, 5, 6, 7, 8, 9, or 10 different dsRNAs.

3. The method of claim 1, wherein said viral gene is from a virus selected from the group consisting of Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), and Kakugo Virus (KV).

4. The method of claim 1, wherein said at least one dsRNA comprises a nucleic acid sequence that is identical or complementary to at least 21 contiguous nucleotides of a sequence selected from the group consisting of SEQ ID NOs:1-21.

5. A method for reducing the susceptibility of a bee to a disease caused by a virus, the method comprising providing to a *Varroa destructor* mite infected by said virus a composition comprising an effective amount of a double-stranded RNA (dsRNA) comprising a nucleic acid sequence that is identical or complementary to a sequence of at least 21 contiguous nucleotides of a viral gene in said virus, thereby suppressing viral replication in the *Varroa destructor* mite and reducing the susceptibility of the bee to the disease caused by the virus.

6. The method of claim 5, wherein said bee is a honey bee.

7. The method of claim 5, wherein the double-stranded RNA (dsRNA) comprises a nucleic acid sequence that is identical or complementary to at least 21 contiguous nucleotides of a sequence selected from the group consisting of SEQ ID NOs:1-10 and 21.

8. The method of claim 5, wherein the virus is selected from the group consisting of Acute Bee Paralysis Virus (ABPV), Deformed Wing Virus (DWV), Kashmir Bee Virus (KBV), Black Queen Cell Virus (BQCV), Sacbrood Virus (SBV), Chronic Bee Paralysis Virus (CPV), Cloudy Wing Virus (CWV), Israeli Acute Paralysis Virus (IAPV), Invertebrate iridescent virus type 6 (IIV-6), *Varroa Destructor* Virus (VDV-1), and Kakugo Virus (KV).

* * * * *